US007186884B2

(12) United States Patent
Osbourn et al.

(10) Patent No.: US 7,186,884 B2
(45) Date of Patent: Mar. 6, 2007

(54) ISOLATED PLANT GENE ENCODING A β AMYRIN SYNTHASE

(75) Inventors: Anne Elisabeth Osbourn, Norwich (GB); Kosmas Haralampidis, Athens (GR); Gregory Thomas Bryan, Feilding (NZ)

(73) Assignee: Plant Bioscience Limited, Norwich (GB)

( * ) Notice: Subject to any disclaimer, the term of this patent is extended or adjusted under 35 U.S.C. 154(b) by 423 days.

(21) Appl. No.: 10/168,445

(22) PCT Filed: Dec. 20, 2000

(86) PCT No.: PCT/GB00/04908

§ 371 (c)(1),
(2), (4) Date: Oct. 30, 2002

(87) PCT Pub. No.: WO01/46391

PCT Pub. Date: Jun. 28, 2001

(65) Prior Publication Data

US 2003/0177518 A1   Sep. 18, 2003

(30) Foreign Application Priority Data

Dec. 22, 1999  (GB) ................................. 9930394.3
Aug. 16, 2000  (GB) ................................. 0020217.6

(51) Int. Cl.
*C12N 15/09* (2006.01)
*C12N 15/29* (2006.01)
*C12N 15/82* (2006.01)
*A01H 5/00* (2006.01)
*A01H 5/10* (2006.01)

(52) U.S. Cl. ....................... 800/278; 800/298; 800/295; 800/279; 800/286; 536/23.2; 536/23.6; 435/320.1; 435/468; 435/430.1; 435/69.1

(58) Field of Classification Search ................ 800/278, 800/279, 298, 295; 536/23.2, 23.6; 435/320.1, 435/468, 69.1, 430.1
See application file for complete search history.

(56) References Cited

FOREIGN PATENT DOCUMENTS

WO   WO 95/30009 A2   11/1995
WO   WO 01/46391 A2   6/2001

OTHER PUBLICATIONS

Shiraiwa, M. "Compositions and content of saponins in soybean seed according to variety"; Agric. Biol. Chem., 55(2): 323:331 (1991).
Okubo, K. "Componets responsible for the undesirable taste of soybean seeds"; Biosci. Biotech. Biochem., 56: 99-103 (1992).
Hayashi, H. Molecular cloning and characterization of CDNA for glycyrrhiza glabra cycloartenol synthase; Biol. Pharm. Bull, 23(2): 231-234 (2000).
Tsukamoto, C. Genetic and Chemical Polymorphisms of Saponins in Soybean Seed; Phytochemistry, 34:1351-1356 (1993).
Tsukamoto, C. "Factors affecting isoflavone content in soybeans seeds: changes in isoflavones, saponins, and compositions of . . . "; J. Agric. Food Chem., 43:1184-1192 (1995).
Yoshiki, Y. "Relationship between chemical structures and biological activities of triterpenoid saponins from soybean"; Biosci. Biotechnol Biochem., 62: 2291-2299 (1998).
Lucas, E. "Soy Protein Products; Processing and Use"; Journal of Nutrition, 125: 573S-580S (1995).
Bach, T. "Cloning of CDNAS or genes encoding enzymes of sterol biosynthesis from plants and other eukaryotes: heterologous . . . "; Progress in Lipid Research, 36:197-226 (1997).
You, S. Molecular Cloning and sequencing of an allium macrostemon cDNA probably encoding oxidosqualene cyclase; Plant Biotechnology, 16(4): 311-214 (1999).
Poralla, K. "A specific amino acid repeat in squalene and oxidosqualene cyclases"; Elsevier Sciences Ltd; 157-158; Apr. 1994.
Papadopoulou, K. "Comprised disease rsistancein saponin-deficient plants"; Eur. J. Bioche. PNAS, 22: 12923-012928 (Oct. 26, 1999).
Kushiro, T. "Cloning of oxidosqualene cyclase that catalyzes the formation of the most popular triterpense among higher plants"; Eur. J. Biochem 256:238-244 (1998).
Shibuya, M. "Two branches of the lupeol synthase gene in the molecular evolution of plant oxidosqualene cyclases"; Eur. J. Biochem. 266: 302-307 (1999).
EMBL Sequence Database, Accession No. 082140; Kushiro, T. (Nov. 1, 1998) Beta-amyrin synthase—clining of oxidosqualene cyclase that catalyzes the formation . . . XP-002170235.
EMBL Sequence Database, Accession No. AI900929; Shoemaker, R.; (Jul. 28, 1999) "Public Soybean EST Project"; XP-002170236.
EMBL Sequence Database, Accesion No. Q9SSZ2; You. S.; (May 1, 2000) "Molecular cloning and sequencing of an allium macrostemon cDNA probably encoding . . . "; XP-002170238.
EMBL Sequence Database, Accession No. AF169966; Darr, L.B.; (Oct. 21, 1999) "A rice cDNA similar to cycloartenol synthase"; XP-002170239.
Natl. Center for Biotechnology Information GI No. 3721856: Kushiro, T., (Oct. 9, 1998) Molecular cloning of oxidosqualene cyclase cDNA from panax ginseng: the isogene.. . .

(Continued)

*Primary Examiner*—Medina A. Ibrahim
(74) *Attorney, Agent, or Firm*—Kathleen D. Rigaut; Dann Dorfman Herrell and Skillman

(57) ABSTRACT

Disclosed are isolated β-amyrin synthase-encoding cDNA and genomic nucleic acids, which are involved in saponin synthesis. Also provided are complementary sequences, vectors, transformed host cells, transformed plants, and methods for influencing or affecting triterpene synthesis, and hence resistance to a fungal pathogen of a plant using β-amyrin synthase encoding nucleic acids.

23 Claims, No Drawings

OTHER PUBLICATIONS

Natl. Center for Biotechnology Information GI No. 3688600; Kushiro, T., (Oct. 3, 1998); Beta-amyrin synthase—clining of oxidosqualene cyclase that catalyzes the formation.. . .

Natl. Center for Biotechnology Information GI No. 3779033; Rounsley, S.D., (Oct. 22, 1998) "Arabidopsis thaliana chromosome II BAC T4E14 genomic sequence".

Accession No. AB009030; Kushiro, T.; (Oct. 3, 1998) Beta-amyrin synthase—cloning of oxidosqualene cyclase that catalyzes the formation of he most popular triterpene among.. . .

Tsukamoto, C. "Genetic improvement of saponi components in soybean"; American Chemical Society; 31: 372-379 (1994).

Wu, T-K.; "Conversion of a plant oxidosqualene-cycloartenol synthase to an oxidosqualene-lanosterol cyclase by random mutagenesis"; Biochemistry; 41: 8238-8244 (2002).

Abe, I.; "Active site mapping of affiity-labeled rat oxidosqualene cyclase" Journal of Biological Chem.; 269(2): 802-804 (Jan. 14, 1994).

Kikuchi, A. "Inheritance and Characterization of a Null Allele for Group A Acetyl Saponins found in a Mutant Soybean" Breeding Science; 49: 167-171 (1999).

US 7,186,884 B2

SEQUENCE LISTING

<160> NUMBER OF SEQ ID NOS: 219

<210> SEQ ID NO 1
<211> LENGTH: 18
<212> TYPE: DNA
<213> ORGANISM: Artificial
<220> FEATURE:
<223> OTHER INFORMATION: Primer

<400> SEQUENCE: 1
gcattggcct ggtgatta                                              18

<210> SEQ ID NO 2
<211> LENGTH: 18
<212> TYPE: DNA
<213> ORGANISM: Artificial
<220> FEATURE:
<223> OTHER INFORMATION: Primer

<400> SEQUENCE: 2
gcccatgagg tggtcaca                                              18

<210> SEQ ID NO 3
<211> LENGTH: 18
<212> TYPE: DNA
<213> ORGANISM: Artificial
<220> FEATURE:
<223> OTHER INFORMATION: Primer

<400> SEQUENCE: 3
ggcgcgtgat tattgtgc                                              18

<210> SEQ ID NO 4
<211> LENGTH: 18
<212> TYPE: DNA
<213> ORGANISM: Artificial
<220> FEATURE:
<223> OTHER INFORMATION: Primer

<400> SEQUENCE: 4
catgaactcg tgcgcctt                                              18

<210> SEQ ID NO 5
<211> LENGTH: 28
<212> TYPE: DNA
<213> ORGANISM: Artificial
<220> FEATURE:
<223> OTHER INFORMATION: Primer

<400> SEQUENCE: 5
ccatgtggag gctaacaata ggtgaggg                                   28

<210> SEQ ID NO 6
<211> LENGTH: 32
<212> TYPE: DNA
<213> ORGANISM: Artificial
<220> FEATURE:
<223> OTHER INFORMATION: Primer

<400> SEQUENCE: 6
tatttctcaa agaaaataac gcatgaatgc tc                              32

<210> SEQ ID NO 7
<211> LENGTH: 44

```
<212> TYPE: DNA
<213> ORGANISM: Artificial
<220> FEATURE:
<223> OTHER INFORMATION: Primer

<400> SEQUENCE: 7
tgcgagtaag gatcctcacg caaggaattc cgaccagaca ggcc        44

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
tgcgagtaag gatcctcacg caag                              24

<210> SEQ ID NO 9
<211> LENGTH: 29
<212> TYPE: DNA
<213> ORGANISM: Artificial
<220> FEATURE:
<223> OTHER INFORMATION: Primer

<400> SEQUENCE: 9
tcagccacgg accgccgccc tcacctatt                         29

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
cacgcaagga attccgacca gaca                              24

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11
ttagcctcca catggtgcgc accaacaacg                        30

<210> SEQ ID NO 12
<211> LENGTH: 31
<212> TYPE: DNA
<213> ORGANISM: Artificial
<220> FEATURE:
<223> OTHER INFORMATION: Primer

<400> SEQUENCE: 12
ggacatcgag gtggttgcat tttagtggat c                      31

<210> SEQ ID NO 13
<211> LENGTH: 32
<212> TYPE: DNA
<213> ORGANISM: Artificial
<220> FEATURE:
<223> OTHER INFORMATION: Primer

<400> SEQUENCE: 13
```

```
ggtgctcttg cttgttctat ggcctcgtct tt                          32

<210> SEQ ID NO 14
<211> LENGTH: 2457
<212> TYPE: DNA
<213> ORGANISM: Artificial
<220> FEATURE:
<223> OTHER INFORMATION: Avena strigosa cDNA

<400> SEQUENCE: 14
attgcttgtt ttcctcgcat acactgcccg ttgttggtgc gcaccatgtg gaggctaaca      60
ataggtgagg gcggcggtcc gtggctgaag tcgaacaatg gcttccttgg ccgccaagtg     120
tgggagtacg acgccgatgc cggcacgccg gaagagcgtg ccgaggttga gagggtgcgt     180
gcggaattca caaagaacag gttccagagg aaggagtcac aggaccttct tctacgcttg     240
cagtacgcaa aagacaaccc tcttccggcg aatattccga cagaagccaa gcttgaaaag     300
agtacagagg tcactcacga gactatctac gaatcattga tgcgagcttt acatcaatat     360
tcctctctac aagcagacga tgggcattgg cctggtgatt acagtgggat tctcttcatt     420
atgcctatca ttatattctc tttatatgtt actagatcac ttgacacctt tttatctccg     480
gaacatcgtc atgagatatg tcgctacatt tacaatcaac agaatgaaga tggtggttgg     540
ggaaaaatgg ttcttggccc aagtaccatg tttggatcgt gtatgaatta tgcaaccta     600 atgattcttg gcgagaagcg aaatggtgat cataaggatg cattggaaaa agggcgttct     660
tggattttat ctcatggaac tgcaactgca ataccacagt ggggaaaaat atggttgtcg     720
ataattggcg tttacgaatg gtcaggaaac aatcctatta tacctgaatt gtggttggtt     780
ccacattttc ttccgattca cccaggtcgt ttttggtgtt ttacccggtt gatatacatg     840
tcaatggcat atctctatgg taagaaattt gttgggccta ttagtcctac aatattagct     900
ctgcgacaag acctctatag tataccttac tgcaacatta ttgggacaa ggcgcgtgat     960 tattgtgcaa aggaggacct tcattaccca cgctcacggg cacaagatct tatatctggt    1020
tgcctaacga aaattgtgga gccaattttg aattggtggc cagcaaacaa gctaagagat    1080
agagctttaa ctaacctcat ggagcatatc cattatgacg acgaatcaac caaatatgtg    1140
ggcatttgcc ctattaacaa ggcattgaac atgatttgtt gttgggtaga aaacccaaat    1200
tcgcctgaat tccaacaaca tcttccacga ttccatgact atttgtggat ggcggaggat    1260
ggaatgaagg cacaggtata tgatggatgt catagctggg aactagcgtt cataattcat    1320
gcctattgtt ccacggatct tactagcgag tttatcccga ctctaaaaaa ggcgcacgag    1380
ttcatgaaga actcacaggt tcttttcaac cacccaaatc atgaaagcta ttatcgccac    1440
agatcaaaag gctcatggac ccttttcaagt gtagataatg gttggtctgt atctgattgt    1500
actgcggaag ctgttaaggc attgctacta ttatcaaaga tatccgctga ccttgttggc    1560
gatccaataa aacaagacag gttgtatgat gccattgatt gcatcctatc tttcatgaat    1620
acagatggaa catttttctac ctacgaatgc aaacggacat tcgcttggtt agaggttctc    1680
aacccttctg agagttttcg gaacattgtc gtggactatc catctgttga atgcacatca    1740
tctgtggttg atgctctcat attatttaaa gagacgaatc cacgatatcg aagagcagag    1800
atagataaat gcattgaaga agctgttgta tttattgaga acagtcaaaa taaggatggt    1860
tcatggtatg gctcatgggg tatatgtttc gcatatggat gcatgtttgc agtaagggcg    1920
ttggttgcta caggaaaaac ctacgacaat tgtgcttcta tcaggaaatc atgcaaattt    1980
gtcttatcaa agcaacaaac aacaggtgga tggggtgaag actatctttc tagtgacaat    2040
```

-continued

```
ggggaatata ttgatagcgg taggcctaat gctgtgacca cctcatgggc aatgttggct   2100
ttaatttatg ctggacaggt tgaacgtgac ccagtaccac tgtataatgc tgcaagacag   2160
ctaatgaata tgcagctaga acaggtgact tcccccaac aggaacacat gggttgcttc    2220
aactcctcct tgaacttcaa ctacgccaac taccgcaatc tatacccgat tatggctctt   2280
ggggaacttc gccgtcgact tcttgcgatt aagagctgat atggaaacaa acatggatgt   2340
ctaggctgcg aggaataaga acattgctcc cacgagcatt catgcgttat tttctttgag   2400
aaataagttc tcttcctacc gatgtcatca tgtaactttt cggaatattt tatgtgt     2457
```

<210> SEQ ID NO 15
<211> LENGTH: 757
<212> TYPE: PRT
<213> ORGANISM: Avena strigosa

<400> SEQUENCE: 15

```
Met Trp Arg Leu Thr Ile Gly Glu Gly Gly Pro Trp Leu Lys Ser
  1               5                  10                  15

Asn Asn Gly Phe Leu Gly Arg Gln Val Trp Glu Tyr Asp Ala Asp Ala
             20                  25                  30

Gly Thr Pro Glu Glu Arg Ala Glu Val Glu Arg Val Arg Ala Glu Phe
         35                  40                  45

Thr Lys Asn Arg Phe Gln Arg Lys Glu Ser Gln Asp Leu Leu Leu Arg
     50                  55                  60

Leu Gln Tyr Ala Lys Asp Asn Pro Leu Pro Ala Asn Ile Pro Thr Glu
 65                  70                  75                  80

Ala Lys Leu Glu Lys Ser Thr Glu Val Thr His Glu Thr Ile Tyr Glu
                 85                  90                  95

Ser Leu Met Arg Ala Leu His Gln Tyr Ser Ser Leu Gln Ala Asp Asp
            100                 105                 110

Gly His Trp Pro Gly Asp Tyr Ser Gly Ile Leu Phe Ile Met Pro Ile
        115                 120                 125

Asn Ile Phe Ser Leu Tyr Val Thr Arg Ser Leu Asp Thr Phe Leu Ser
    130                 135                 140

Pro Glu His Arg His Glu Ile Cys Arg Tyr Ile Tyr Asn Gln Gln Asn
145                 150                 155                 160

Glu Asp Gly Gly Trp Gly Lys Met Val Leu Gly Pro Ser Thr Met Phe
                165                 170                 175

Gly Ser Cys Met Asn Tyr Ala Thr Leu Met Ile Leu Gly Glu Lys Arg
            180                 185                 190

Asn Gly Asp His Lys Asp Ala Leu Glu Lys Gly Arg Ser Trp Ile Leu
        195                 200                 205

Ser His Gly Thr Ala Thr Ala Ile Pro Gln Trp Gly Lys Ile Trp Leu
    210                 215                 220

Ser Ile Ile Gly Val Tyr Glu Trp Ser Gly Asn Asn Pro Ile Ile Pro
225                 230                 235                 240

Glu Leu Trp Leu Val Pro His Phe Leu Pro Ile His Pro Gly Arg Phe
                245                 250                 255

Trp Cys Phe Thr Arg Leu Ile Tyr Met Ser Met Ala Tyr Leu Tyr Gly
            260                 265                 270

Lys Lys Phe Val Gly Pro Ile Ser Pro Thr Ile Leu Ala Leu Arg Gln
        275                 280                 285

Asp Leu Tyr Ser Ile Pro Tyr Cys Asn Ile Asn Trp Asp Lys Ala Arg
    290                 295                 300
```

-continued

```
Asp Tyr Cys Ala Lys Glu Asp Leu His Tyr Pro Arg Ser Arg Ala Gln
305                 310                 315                 320

Asp Leu Ile Ser Gly Cys Leu Thr Lys Ile Val Glu Pro Ile Leu Asn
            325                 330                 335

Trp Trp Pro Ala Asn Lys Leu Arg Asp Arg Ala Leu Thr Asn Leu Met
            340                 345                 350

Glu His Ile His Tyr Asp Asp Glu Ser Thr Lys Tyr Val Gly Ile Cys
        355                 360                 365

Pro Ile Asn Lys Ala Leu Asn Met Ile Cys Cys Trp Val Glu Asn Pro
    370                 375                 380

Asn Ser Pro Glu Phe Gln Gln His Leu Pro Arg Phe His Asp Tyr Leu
385                 390                 395                 400

Trp Met Ala Glu Asp Gly Met Lys Ala Gln Val Tyr Asp Gly Cys His
            405                 410                 415

Ser Trp Glu Leu Ala Phe Ile Ile His Ala Tyr Cys Ser Thr Asp Leu
            420                 425                 430

Thr Ser Glu Phe Ile Pro Thr Leu Lys Lys Ala His Glu Phe Met Lys
        435                 440                 445

Asn Ser Gln Val Leu Phe Asn His Pro Asn His Glu Ser Tyr Tyr Arg
    450                 455                 460

His Arg Ser Lys Gly Ser Trp Thr Leu Ser Ser Val Asp Asn Gly Trp
465                 470                 475                 480

Ser Val Ser Asp Cys Thr Ala Glu Ala Val Lys Ala Leu Leu Leu Leu
            485                 490                 495

Ser Lys Ile Ser Ala Asp Leu Val Gly Asp Pro Ile Lys Gln Asp Arg
        500                 505                 510

Leu Tyr Asp Ala Ile Asp Cys Ile Leu Ser Phe Met Asn Thr Asp Gly
    515                 520                 525

Thr Phe Ser Thr Tyr Glu Cys Lys Arg Thr Phe Ala Trp Leu Glu Val
        530                 535                 540

Leu Asn Pro Ser Glu Ser Phe Arg Asn Ile Val Val Asp Tyr Pro Ser
545                 550                 555                 560

Val Glu Cys Thr Ser Ser Val Val Asp Ala Leu Ile Leu Phe Lys Glu
            565                 570                 575

Thr Asn Pro Arg Tyr Arg Arg Ala Glu Ile Asp Lys Cys Ile Glu Glu
            580                 585                 590

Ala Val Val Phe Ile Glu Asn Ser Gln Asn Lys Asp Gly Ser Trp Tyr
        595                 600                 605

Gly Ser Trp Gly Ile Cys Phe Ala Tyr Gly Cys Met Phe Ala Val Arg
    610                 615                 620

Ala Leu Val Ala Thr Gly Lys Thr Tyr Asp Asn Cys Ala Ser Ile Arg
625                 630                 635                 640

Lys Ser Cys Lys Phe Val Leu Ser Lys Gln Gln Thr Thr Gly Gly Trp
            645                 650                 655

Gly Glu Asp Tyr Leu Ser Ser Asp Asn Gly Glu Tyr Ile Asp Ser Gly
            660                 665                 670

Arg Pro Asn Ala Val Thr Thr Ser Trp Ala Met Leu Ala Leu Ile Tyr
        675                 680                 685

Ala Gly Gln Val Glu Arg Asp Pro Val Pro Leu Tyr Asn Ala Ala Arg
    690                 695                 700

Gln Leu Met Asn Met Gln Leu Glu Thr Gly Asp Phe Pro Gln Gln Glu
705                 710                 715                 720
```

```
His Met Gly Cys Phe Asn Ser Ser Leu Asn Phe Asn Tyr Ala Asn Tyr
                725                 730                 735

Arg Asn Leu Tyr Pro Ile Met Ala Leu Gly Glu Leu Arg Arg Leu
            740                 745                 750

Leu Ala Ile Lys Ser
        755

<210> SEQ ID NO 16
<211> LENGTH: 262
<212> TYPE: DNA
<213> ORGANISM: Avena strigosa

<400> SEQUENCE: 16
acagaggtca ctcacgagac tatctacgaa tcattgatgc gagctttaca tcaatattcc      60
tctctacaag cagacgatgg gcattggcct ggtgattaca gtgggattct cttcattatg    120
cctatcatta tattctcttt atatgttact agatcacttg cacctttttt atctccggaa    180
catcgtcatg agatatgtcg ctacatttac aaccaacaga atgaagatgg tggttgggga    240
aaaatggttc ttggcccaac gt                                              262

<210> SEQ ID NO 17
<211> LENGTH: 388
<212> TYPE: DNA
<213> ORGANISM: Avena strigosa
<220> FEATURE:
<221> NAME/KEY: misc_feature
<222> LOCATION: (240)..()
<223> OTHER INFORMATION: n is a or c or g or t

<400> SEQUENCE: 17
accatgtgga ggctaacaat aggtgagggc ggcggtccgt ggctgaagtc gaacaatggc     60
ttccttggcc gccaagtgtg ggagtacgac gccgatgccg gcacgccgga agagcgtgcc   120
gaggttgaga gggtgcgtgc ggaattcaca aagaacaggt tccagaggaa ggagtcacag   180
gaccttcttc tacgcttgca gtacgcaaaa gacaaccctc ttccggcgaa tattccgacn   240
gaagccaagc ttgaaaagag tacagaggtc actcacgaga ctatctacga atcattgatg   300
cgagctctac atcaatattc ctctttacaa gcagacgatg ggcattggcc tggtgattac   360
agtgggattc tcttcattat gcctatca                                      388

<210> SEQ ID NO 18
<211> LENGTH: 388
<212> TYPE: DNA
<213> ORGANISM: Avena strigosa
<220> FEATURE:
<221> NAME/KEY: misc_feature
<222> LOCATION: 97, 340
<223> OTHER INFORMATION: n is a or c or g or t

<400> SEQUENCE: 18
accatgtgga ggctaacaat aggtgagggc ggcggtccgt ggctgaagtc gaacaatggc     60
ttccttggcc gccaagtgtg ggagtacgac gccgatnccg gcacgccgga agagcgtgcc   120
gaggttgaga gggtgcgtgc ggaattcaca aagaacaggt tccagaggaa ggagtcacag   180
gaccttcttc tacgcttgca gtacgcaaaa gacaaccctc ttccggcgaa tattccgaca   240
gaagccaagc ttgaaaagag tacagaggtc actcacgaga ctatctacga atcattgatg   300
cgagctctac atcaatattc ctctttacaa gcagacgatn ggcattggcc tggtgattac   360
agtgggattc tcttcattat gcctatca                                      388
```

<210> SEQ ID NO 19
<211> LENGTH: 388
<212> TYPE: DNA
<213> ORGANISM: Avena strigosa
<220> FEATURE:
<221> NAME/KEY: misc_feature
<222> LOCATION: 169, 313
<223> OTHER INFORMATION: n is a or c or g or t

<400> SEQUENCE: 19

| | |
|---|---|
| accatgtgga ggctaacaat aggtgagggc ggcggtccgt ggctgaagtc gaacaatggc | 60 |
| ttccttggcc gccaagtgtg ggagtacgac gccgatgccg gcacgccgga agagcgtgcc | 120 |
| gaggttgaga gggtgcgtgc ggaattcaca aagaacaggt tccagaggna ggagtcacag | 180 |
| gaccttcttc tacgcttgca gtacgcaaaa gacaaccctc ttccggcgaa tattccgaca | 240 |
| gaagccaagc ttgaaaagag tacagaggtc actcacgaga ctatctacga atcattgatg | 300 |
| cgagctctac atnaatattc ctctttacaa gcagacgatg ggcattggcc tggtgattac | 360 |
| agtgggattc tcttcattat gcctatca | 388 |

<210> SEQ ID NO 20
<211> LENGTH: 388
<212> TYPE: DNA
<213> ORGANISM: Avena strigosa
<220> FEATURE:
<221> NAME/KEY: misc_feature
<222> LOCATION: (190)..(190)
<223> OTHER INFORMATION: n is a or c or g or t

<400> SEQUENCE: 20

| | |
|---|---|
| accatgtgga ggctaacaat aggtgagggc ggcggtccgt ggctgaagtc gaacaatggc | 60 |
| ttccttggcc gccaagtgtg ggagtacgac gccgatgccg gcacgccgga agagcgtgcc | 120 |
| gaggttgaga gggtgcgtgc ggaattcaca aagaacaggt tccagaggaa ggagtcacag | 180 |
| gaccttcttn tacgcttgca gtacgcaaaa gacaaccctc ttccggcgaa tattccgaca | 240 |
| gaagccaagc ttgaaaagag tacagaggtc actcacgaga ctatctacga atcattgatg | 300 |
| cgagctctac atcaatattc ctctttacaa gcagacgatg ggcattggcc tggtgattac | 360 |
| agtgggattc tcttcattat gcctatca | 388 |

<210> SEQ ID NO 21
<211> LENGTH: 388
<212> TYPE: DNA
<213> ORGANISM: Avena strigosa
<220> FEATURE:
<221> NAME/KEY: misc_feature
<222> LOCATION: 29, 312
<223> OTHER INFORMATION: n is a or c or g or t

<400> SEQUENCE: 21

| | |
|---|---|
| accatgtgga ggctaacaat aggtgaggnc ggcggtccgt ggctgaagtc gaacaatggc | 60 |
| ttccttggcc gccaagtgtg ggagtacgac gccgatgccg gcacgccgga agagcgtgcc | 120 |
| gaggttgaga gggtgcgtgc ggaattcaca aagaacaggt tccagaggaa ggagtcacag | 180 |
| gaccttcttc tacgcttgca gtacgcaaaa gacaaccctc ttccggcgaa tattccgacg | 240 |
| gaccttcttc tacgcttgca gtacgcaaaa gacaaccctc ttccggcgaa tattccgacg | 300 |
| cgagctctac ancaatattc ctctttacaa gcagacgatg ggcattggcc tggtgattac | 360 |
| agtgggattc tcttcattat gcctatca | 388 |

<210> SEQ ID NO 22
<211> LENGTH: 389
<212> TYPE: DNA
<213> ORGANISM: Avena strigosa
<220> FEATURE:
<221> NAME/KEY: misc_feature
<222> LOCATION: (164)..(164)
<223> OTHER INFORMATION: n is a or c or g or t

<400> SEQUENCE: 22

| | | | | | |
|---|---|---|---|---|---|
| accatgtgga | ggctaacaat | aggtgagggc | ggcggtccgt | ggctgaagtc | gaacaatggc | 60 |
| ttccttggcc | gccaagtgtg | ggagtacgac | gccgatgccg | gcacgccgga | agagcgtgcc | 120 |
| gaggttgaga | gggtgcgtgc | ggaattcaca | agaacaggt | tccnagagga | aggagtcaca | 180 |
| ggaccttctt | ctacgcttgc | agtacgcaaa | agacaaccct | cttccggcga | atattccgac | 240 |
| agaagccaag | cttgaaaaga | gtacagaggt | cactcacgag | actatctacg | aatcattgat | 300 |
| gcgagctcta | catcaatatt | cctctttaca | agcagacgat | gggcattggc | ctggtgatta | 360 |
| cagtgggatt | ctcttcatta | tgcctatca | | | | 389 |

<210> SEQ ID NO 23
<211> LENGTH: 328
<212> TYPE: DNA
<213> ORGANISM: Avena strigosa
<220> FEATURE:
<221> NAME/KEY: misc_feature
<222> LOCATION: (157)..(157)
<223> OTHER INFORMATION: n is a or c or g or t
<220> FEATURE:
<221> NAME/KEY: misc_feature
<222> LOCATION: (178)..(178)
<223> OTHER INFORMATION: n is a or c or g or t

<400> SEQUENCE: 23

| | | | | | |
|---|---|---|---|---|---|
| cataaaatat | tccgaaaagt | tacatgatga | catcggtagg | aagagaactt | atttctcaaa | 60 |
| gaaaataacg | catgaatgct | cgtgggagca | atgttcttat | tcctcgcagc | ctagacatcc | 120 |
| atgtttgttt | ccatatcagc | tcttaatcgc | aagaagncga | cggcgaagtt | ccccaagngc | 180 |
| cataatcggg | tatagattgc | ggtagttggc | gtagttgaag | ttcaaggagg | agttgaagca | 240 |
| acccatgtgt | tcctgttggg | ggaagtcacc | tgtttctagc | tgcatattca | ttagctgtct | 300 |
| tgcagcatta | tacaggggta | ctgggtca | | | | 328 |

<210> SEQ ID NO 24
<211> LENGTH: 328
<212> TYPE: DNA
<213> ORGANISM: Avena strigosa
<220> FEATURE:
<221> NAME/KEY: misc_feature
<222> LOCATION: (157)..(157)
<223> OTHER INFORMATION: n is a or c or g or t

<400> SEQUENCE: 24

| | | | | | |
|---|---|---|---|---|---|
| cataaaatat | tccgaaaagt | tacatgatga | catcggtagg | aagagaactt | atttctcaaa | 60 |
| gaaaataacg | catgaatgct | cgtgggagca | atgttcttat | tcctcgcagc | ctagacatcc | 120 |
| atgtttgttt | ccatatcagc | tcttaatcgc | aagaagncga | cggcgaagtt | ccccaagagc | 180 |
| cataatcggg | tatagattgc | ggtagttggc | gtagttgaag | ttcaaggagg | agttgaagca | 240 |
| acccatgtgt | tcctgttggg | ggaagtcacc | tgtttctagc | tgcatattca | ttagctgtct | 300 |
| tgcagcatta | tacaggggta | ctgggtca | | | | 328 |

<210> SEQ ID NO 25

```
<211> LENGTH: 330
<212> TYPE: DNA
<213> ORGANISM: Avena strigosa
<220> FEATURE:
<221> NAME/KEY: misc_feature
<222> LOCATION: (185)..(185)
<223> OTHER INFORMATION: n is a or c or g or t
<220> FEATURE:
<221> NAME/KEY: misc_feature
<222> LOCATION: (253)..(253)
<223> OTHER INFORMATION: n is a or c or g or t

<400> SEQUENCE: 25
cataaaatat tccgaaaagt tacatgatga catcggtagg aagagaactt atttctcaaa      60
gaaaataacg catgaatgct cgtgggagca atgttcttat tcctcgcagc ctagacatcc    120
atgtttgttt ccatatcagc tcttaatcgc aagaagtcga cggcgaagtt ccccaagagc    180
catanatcgg gtatagattg cggtagttgg cgtagttgaa gttcaaggag gagttgaagc    240
aacccatgtg ttncctgttg ggggaagtca cctgtttcta gctgcatatt cattagctgt    300
cttgcagcat tatacagggg tactgggtca                                     330

<210> SEQ ID NO 26
<211> LENGTH: 328
<212> TYPE: DNA
<213> ORGANISM: Avena strigosa
<220> FEATURE:
<221> NAME/KEY: misc_feature
<222> LOCATION: (36)..(36)
<223> OTHER INFORMATION: n is a or c or g or t
<220> FEATURE:
<221> NAME/KEY: misc_feature
<222> LOCATION: (249)..(249)
<223> OTHER INFORMATION: n is a or c or g or t

<400> SEQUENCE: 26
cataaaatat tccgaaaagt tacatgatga catcgntagg aagagaactt atttctcaaa      60
gaaaataacg catgaatgct cgtgggagca atgttcttat tcctcgcagc ctagacatcc    120
atgtttgttt ccatatcagc tcttaatcgc aagaagtcga cggcgaagtt ccccaagagc    180
cataatcggg tatagattgc ggtagttggc gtagttgaag ttcaaggagg agttgaagca    240
acccatgtnt tcctgttggg ggaagtcacc tgtttctagc tgcatattca ttagctgtct    300
tgcagcatta tacaggggta ctgggtca                                      328

<210> SEQ ID NO 27
<211> LENGTH: 328
<212> TYPE: DNA
<213> ORGANISM: Avena strigosa
<220> FEATURE:
<221> NAME/KEY: misc_feature
<222> LOCATION: (173)..(173)
<223> OTHER INFORMATION: n is a or c or g or t

<400> SEQUENCE: 27
cataaaatat tccgaaaagt tacatgatga catcggtagg aagagaactt atttctcaaa      60
gaaaataacg catgaatgct cgtgggagca atgttcttat tcctcgcagc ctagacatcc    120
atgtttgttt ccatatcagc tcttaatcgc aagaagtcga cggcgaagtt ccncaagagc    180
cataatcggg tatagattgc ggtagttggc gtagttgaag ttcaaggagg agttgaagca    240
acccatgtgt tcctgttggg ggaagtcacc tgtttctagc tgcatattca ttagctgtct    300
tgcagcatta tacaggggta ctgggtca                                      328
```

<210> SEQ ID NO 28
<211> LENGTH: 329
<212> TYPE: DNA
<213> ORGANISM: Avena strigosa
<220> FEATURE:
<221> NAME/KEY: misc_feature
<222> LOCATION: (184)..(184)
<223> OTHER INFORMATION: n is a or c or g or t
<220> FEATURE:
<221> NAME/KEY: misc_feature
<222> LOCATION: (229)..(229)
<223> OTHER INFORMATION: n is a or c or g or t

<400> SEQUENCE: 28

```
cataaaatat tccgaaaagt tacatgatga catcggtagg aagagaactt atttctcaaa      60
gaaaataacg catgaatgct cgtgggagca atgttcttat tcctcgcagc ctagacatcc     120
atgtttgttt ccatatcagc tcttaatcgc aagaagtcga cggcgaagtt ccccaagagc     180
catnatcggg tatagattgc ggtagttggc gtagttgaag ttcaaggang gagttgaagc     240
aacccatgtg ttcctgttgg gggaagtcac ctgtttctag ctgcatattc attagctgtc     300
ttgcagcatt atacaggggt actgggtca                                       329
```

<210> SEQ ID NO 29
<211> LENGTH: 30
<212> TYPE: PRT
<213> ORGANISM: Rattus sp.

<400> SEQUENCE: 29

His Lys Gly Gly Phe Pro Phe Ser Thr Leu Asp Gly Gly Trp Ile Val
1               5                   10                  15

Ala Asp Asp Thr Ala Glu Ala Leu Lys Ala Val Leu Leu Leu
            20                  25                  30

<210> SEQ ID NO 30
<211> LENGTH: 30
<212> TYPE: PRT
<213> ORGANISM: Unknown
<220> FEATURE:
<223> OTHER INFORMATION: Yeast

<400> SEQUENCE: 30

Arg Lys Gly Ala Trp Gly Phe Ser Thr Lys Thr Gln Gly Tyr Thr Val
1               5                   10                  15

Ala Asp Cys Thr Ala Glu Ala Ile Lys Ala Ile Ile Met Val
            20                  25                  30

<210> SEQ ID NO 31
<211> LENGTH: 30
<212> TYPE: PRT
<213> ORGANISM: Avena strigosa

<400> SEQUENCE: 31

Ser Lys Gly Ala Trp Pro Phe Ser Thr Ala Asp His Gly Trp Pro Ile
1               5                   10                  15

Ser Asp Cys Thr Ala Glu Gly Leu Lys Ala Ala Leu Leu Leu
            20                  25                  30

<210> SEQ ID NO 32
<211> LENGTH: 30
<212> TYPE: PRT
<213> ORGANISM: Panax ginseng

<400> SEQUENCE: 32

```
Ser Lys Gly Ala Trp Pro Phe Ser Thr Ala Asp His Gly Trp Pro Ile
1               5                   10                  15

Ser Asp Cys Thr Ala Glu Gly Phe Lys Ala Val Leu Gln Leu
                20                  25                  30

<210> SEQ ID NO 33
<211> LENGTH: 30
<212> TYPE: PRT
<213> ORGANISM: Avena strigosa

<400> SEQUENCE: 33

Ser Lys Gly Ser Trp Thr Leu Ser Ser Val Asp Asn Gly Trp Ser Val
1               5                   10                  15

Ser Asp Cys Thr Ala Glu Ala Val Lys Ala Leu Leu Leu Leu
                20                  25                  30

<210> SEQ ID NO 34
<211> LENGTH: 30
<212> TYPE: PRT
<213> ORGANISM: Panax ginseng

<400> SEQUENCE: 34

Ser Lys Gly Ser Trp Thr Phe Ser Asp Gln Asp His Gly Trp Gln Val
1               5                   10                  15

Ser Asp Cys Thr Ala Glu Gly Leu Lys Cys Cys Leu Ile Phe
                20                  25                  30

<210> SEQ ID NO 35
<211> LENGTH: 759
<212> TYPE: PRT
<213> ORGANISM: Avena strigosa

<400> SEQUENCE: 35

Met Trp Arg Leu Lys Ile Ala Glu Gly Gly Asp Pro Trp Leu Arg
1               5                   10                  15

Thr Lys Asn Ala His Val Gly Arg Gln Val Trp Glu Phe Asp Pro Glu
                20                  25                  30

Ala Gly Asp Pro Glu Ala Leu Ala Val Glu Ala Ala Arg Arg Asp
            35                  40                  45

Phe Ala Ala Gly Arg His Arg Leu Lys His Ser Ser Asp Arg Leu Met
    50                  55                  60

Arg Ile Gln Phe Glu Lys Glu Asn Pro Leu Lys Leu Asp Leu Pro Ala
65                  70                  75                  80

Ile Lys Leu Glu Glu Asn Glu Asp Val Thr Glu Ala Val Ser Thr
                85                  90                  95

Ser Leu Lys Arg Ala Ile Ser Arg Phe Ser Thr Leu Gln Ala His Asp
                100                 105                 110

Gly His Trp Pro Gly Asp Tyr Gly Gly Pro Met Phe Leu Met Pro Gly
            115                 120                 125

Leu Leu Ile Thr Leu Tyr Val Thr Gly Ser Leu Asn Thr Val Leu Ser
    130                 135                 140

Pro Glu His Gln Lys Glu Ile Arg Arg Tyr Leu Tyr Asn His Gln Asn
145                 150                 155                 160

Glu Asp Gly Gly Trp Gly Leu His Ile Glu Gly Pro Ser Thr Met Phe
                165                 170                 175

Gly Ser Ala Leu Thr Tyr Val Ser Leu Arg Leu Leu Gly Glu Gly Pro
            180                 185                 190

Glu Ser Gly Asp Gly Ala Met Glu Lys Gly Arg Asn Trp Ile Leu Asp
```

-continued

```
            195                 200                 205
His Gly Gly Ala Thr Tyr Ile Thr Ser Trp Gly Lys Phe Trp Leu Ala
        210                 215                 220
Val Leu Gly Val Phe Asp Trp Ser Gly Asn Asn Pro Leu Pro Pro Glu
225                 230                 235                 240
Ile Trp Met Leu Pro Tyr Arg Leu Pro Ile His Pro Gly Arg Met Trp
                245                 250                 255
Cys His Cys Arg Met Val Tyr Leu Pro Met Cys Tyr Val Tyr Gly Lys
                260                 265                 270
Arg Phe Val Gly Lys Ile Thr Pro Leu Ile Leu Glu Leu Arg Asn Glu
            275                 280                 285
Leu Tyr Lys Thr Pro Tyr Ser Lys Ile Asp Trp Asp Ser Ala Arg Asn
        290                 295                 300
Leu Cys Ala Lys Glu Asp Leu Tyr Tyr Pro His Pro Leu Ile Gln Asp
305                 310                 315                 320
Ile Leu Trp Ala Thr Leu His Lys Phe Val Glu Pro Val Met Met His
                325                 330                 335
Trp Pro Gly Asn Lys Leu Arg Glu Lys Ala Leu Asn His Val Met Gln
                340                 345                 350
His Val His Tyr Glu Asp Glu Asn Thr Arg Tyr Ile Cys Ile Gly Pro
            355                 360                 365
Val Asn Lys Val Leu Asn Met Leu Thr Cys Trp Ile Glu Asp Pro Asn
        370                 375                 380
Ser Glu Ala Phe Lys Leu His Ile Pro Arg Val His Asp Tyr Leu Trp
385                 390                 395                 400
Val Ala Glu Asp Gly Met Lys Met Gln Gly Tyr Asn Gly Ser Gln Leu
                405                 410                 415
Trp Asp Thr Ala Phe Ala Val Gln Ala Ile Thr Ala Thr Gly Leu Ile
                420                 425                 430
Asp Glu Phe Ala Pro Thr Leu Lys Leu Ala His Asn Phe Ile Lys Asn
            435                 440                 445
Ser Gln Val Leu Asp Asp Cys Pro Gly Asp Leu Ser Tyr Trp Tyr Arg
        450                 455                 460
His Ile Ser Lys Gly Ala Trp Pro Phe Ser Thr Ala Asp His Gly Trp
465                 470                 475                 480
Pro Ile Ser Asp Cys Thr Ala Glu Gly Leu Lys Ala Ala Leu Leu Leu
                485                 490                 495
Ser Lys Ile Ser Pro Glu Ile Val Gly Glu Pro Val Glu Val Asn Arg
                500                 505                 510
Leu Tyr Asp Ala Val Asn Cys Leu Met Ser Trp Met Asn Asn Asn Gly
            515                 520                 525
Gly Phe Ala Thr Tyr Glu Leu Thr Arg Ser Tyr Ala Trp Leu Glu Leu
        530                 535                 540
Ile Asn Pro Ala Glu Thr Phe Gly Asp Ile Val Ile Asp Tyr Pro Tyr
545                 550                 555                 560
Val Glu Cys Thr Ser Ala Ala Ile Gln Ala Leu Thr Ser Phe Lys Lys
                565                 570                 575
Leu Tyr Pro Gly His Arg Arg Lys Asp Val Asp Asn Cys Ile Asn Lys
                580                 585                 590
Ala Ala Asn Phe Ile Glu Ser Ile Gln Arg Ser Asp Gly Ser Trp Tyr
            595                 600                 605
Gly Ser Trp Ala Val Cys Phe Thr Tyr Gly Thr Trp Phe Gly Val Lys
        610                 615                 620
```

-continued

```
Ala Leu Val Ala Ala Gly Arg Thr Phe Lys Ser Ser Pro Ala Ile Arg
625                 630                 635                 640

Lys Ala Cys Glu Phe Leu Met Ser Lys Glu Leu Pro Phe Gly Gly Trp
            645                 650                 655

Gly Lys Ser Tyr Leu Ser Cys Gln Asp Gln Val Tyr Thr Asn Leu Glu
        660                 665                 670

Gly Lys His Ala His Ala Val Asn Thr Gly Trp Ala Met Leu Thr Leu
    675                 680                 685

Ile Asp Ala Gly Gln Ala Glu Arg Asp Pro Thr Pro Leu His Arg Ala
690                 695                 700

Ala Lys Val Leu Ile Asn Leu Gln Ser Glu Asp Gly Glu Phe Pro Gln
705                 710                 715                 720

Gln Glu Ile Met Gly Val Phe Asn Lys Asn Cys Met Ile Ser Tyr Ser
                725                 730                 735

Gln Tyr Arg Asp Ile Phe Pro Val Trp Ala Leu Gly Glu Tyr Arg Cys
            740                 745                 750

Arg Val Leu Ala Ala Gly Lys
        755
```

<210> SEQ ID NO 36
<211> LENGTH: 7340
<212> TYPE: DNA
<213> ORGANISM: Avena strigosa

<400> SEQUENCE: 36

```
atgtggaggc taacaatagg tgagggcggc ggtccgtggc tgaagtcgaa caatggcttc      60
cttggccgcc aagtgtggga gtacgacgcc gatgccggca cgccggaaga gcgtgccgag     120
gttgagaggg tgcgtgcgga attcacaaag aacaggttcc agaggaagga gtcacaggac     180
cttcttctac gcttgcaggt acatgcgtct tctttcccct acttccatat acacccagta     240
gtatatgttg ccactgccgt tagctctagc tttaggactg agaaaagggc tctcagataa     300
tccatatctc tctttagatg gagggtttgc ttttatttat tattacatat tgttcaatcc     360
ttgctgtgta tatcatcaac tgcagtacgc aaaagacaac cctcttccgg cgaatattcc     420
gacagaagcc aagcttgaaa agagtacaga ggtcactcac gagactatct acgaatcatt     480
gatgcgagct ttacatcaat attcctctct acaagcagac gatgggcatt ggcctggtga     540
ttacagtggg attctcttca ttatgcctat cattgtaagt attttactat tattttatga     600
tacagcaatt tggcaattaa tatatgcata cgaggtttct tatttcgtaa atactcaaga     660
caatatagca tgtggaatct tataatttct ataatgaata tgtaccgtct tgtgtgcgca     720
atacgtatac tatattattc cgctatgcat atagtattac ataccaatat tgatagatgt     780
tcaaaccaat tatgaagagt ttaactacaa gatttaatat agtagtttct gttattctag     840
cagcaagtta cctccattag gttccggaag ttctactctt accacctata tatatgtatt     900
attgcttata ctaccttcgt ctcaaagttt aagacttttt tttaaagtca atttatggaa     960
agtttgaact aacttttata aaactatcaa gaactatgat attatatttg ccatgtgaaa    1020
atatgtttta ttatgtatca aagggtatgg atttcgtacc gtaaatataa tattgttgtc    1080
taaaatcttg gttgaacttt acttagtttg acttttggaa agtatataag ccttaaactt    1140
taaaatagac gtagtaattc agatgcactt cactgatatc ccgacaaaag tacaaaatac    1200
atttatggaa tgtcaaattt atttgaaaac aacacatttg gttagcttc aatatttcgg     1260
aaaagaaaat atgaggagtg atttaaataa gttcttaagg ttttcatgaa aaacaaatct    1320
```

```
gttatgggga ctttatgcaa agagaacaag attggctctt agaaatttct ttagatatga    1380
ttaaattaaa atacagtgtt tgcactaaaa ccacatttgg tttgatttga atatttgaaa    1440
gagatagaaa atcttgaaca tttatttta gggaatatag gctttattac taccatccta    1500
tgtatcatcg atggtggctc atcacattga tcacaactct gaaaactaag aagtctccaa    1560
catttagaca atgatattgg tttttcaaat ttcagtaaca cttacaagaa ttccgttgat    1620
tttattctcc atccgagaac tcatttctcc tctcctaata atgatgcaca tatatgatgg    1680
gatcttttct ttatgttgca gatattctct ttatatgtta ctagatcact tgacaccttt    1740
ttatctccgg aacatcgtca tgagatatgt cgctacattt acaatcaaca ggcatgggat    1800
taaacctaac acatatttcc atatttgttt tctatatgtt tgtgattttg tgaccaaaat    1860
aaaaacagta cttaatgcaa catatattga gcagaatgaa gatggtggtt ggggaaaaat    1920
ggttcttggc ccaagtacca tgtttggatc gtgtatgaat tatgcaacct taatgattct    1980
tggcgagaag cgaaatggtg atcataagga tgcattggaa aaaggggcgtt cttggatttt    2040
atctcatgga actgcaactg caataccaca gtggggaaaa atatggttgt cggtatgtta    2100
aataacacaa gatatcaatg ctcatatatg ttctcttctg aactaacgtt aaatcaacct    2160
actatttgat aacatcatag ataattggcg tttacgaatg gtcaggaaac aatcctatta    2220
tacctgaatt gtggttggtt ccacattttc ttccgattca cccaggtatt tctatctagc    2280
ttgcatatat aacaaaattg ttgtagaacg catgcttaga ccatcattct gtggaattat    2340
tctgtgcaat ttgttgcttg tggaagcaat ttaaccatat atcaaacaag gaatattgag    2400
gcatggtacc tgaaatagtt ttttgaaaaa tacatgccga aaggaaatc aatgtttcaa    2460
ttaggcatgt ttgcacgtag attccacaag attctcttgt atatgttttg atcttggaga    2520
tacatgtata tatttatgta tctttcatat tatctcaaaa aaataacatg ttactacccc    2580
ctctatccat aataagtgtc ggtcacttag tacaaacttt tactagcttt agtacaaaat    2640
ggacgactct tattatggat tgcagggagt actaaatatt atgaagttga accttatcat    2700
tcacaagtaa tttattggaa aataatcctt catatgtagg tcgttttggg tgttttaccc    2760
ggttgatata catgtcaatg gcatatctct atggtaagaa atttgttggg cctattagtc    2820
ctacaatatt agctctgcga caagacctct atagtatacc ttactgcaac attaattggg    2880
acaaggcgcg tgattattgt gcaaaggtta gttagttaat caatcactat atatatgtat    2940
tcagtttgtt agaatatatt aatttagccc atgtcactac ataatatttt catggattca    3000
agattaagaa catcacgtag aataatgaag tacatcattt cagtacttgg tatctcagaa    3060
aaaatataga ctaagaaagc tagtgttctt caaaaatttt atgttgtttc aggaggacct    3120
tcattaccca cgctcacggg cacaagatct tatatctggt tgcctaacga aaattgtgga    3180
gccaattttg aattggtggc cagcaaacaa gctaagagat agagctttaa ctaacctcat    3240
ggagcatatc cattatgacg acgaatcaac caaatatgtg ggcatttgcc ctattaacaa    3300
ggtgaaatta ttttcaaatt gatttgcacc ttttacttta ataatgacgg atgttattcc    3360
attctaatgt tttaacatgt ttattgtaat taggcattga acatgatttg ttgttgggta    3420
gaaaacccaa attcgcctga attccaacaa catcttccac gattccatga ctatttgtgg    3480
atggcggagg atggaatgaa ggcacaggtt ggtatagagc tcttgtcaga tattttgcca    3540
atttaactac gtgccaattc ttcacaacca ttaccttttt tcatgaatat atatttcctc    3600
aaacaaaatg tgagaatctt ttgggttaca aggatttttt attttcatct atatctaggt    3660
```

```
tgcattcaat aagcatgttt gtgcatgtcc gagttctcct gaaccaaact aaaatgcata    3720
ttctctttag ctgcacatag tgtatatgaa ataaaattat ggtaataata tttttacttt    3780
agttaattct aatgacgaaa tagttgatat gcctatatcg tttcgaatat ataaatcaga    3840
ggtagttaga aaaattattg gacttacatc aaatgcaaac tgtgaatgta aagtaatat    3900 gtatacaatc gcaggtatat gatggatgtc atagctggga actagcgttc ataattcatg    3960
cctattgttc cacggatctt actagcgagt ttatcccgac tctaaaaaag gcgcacgagt    4020
tcatgaagaa ctcacaggtt tgttgttctc catattatat tattgctcaa attctgaaaa    4080
gatctaacat taattgtcta cccttgaagg ttcttttcaa ccacccaaat catgaaagct    4140
attatcgcca cagatcaaaa ggctcatgga cccttttcaag tgtagataat ggttggtctg    4200
tatctgattg tactgcggaa gctgttaagg ttaacataag aaccatgtct tccaattgta    4260
catatataag tacatatgtg aatacatgac gggttaccct gtataagttg aaatgaacta    4320
ttcatgaata tattgaatct acattaatat tcattatttt ttcaggcatt gctactatta    4380
tcaaagatat ccgctgacct tgttggcgat ccaataaaac aagacaggtt gtatgatgcc    4440
attgattgca tcctatcttt catggtatga aatctaaat tggatcaatt aacaaacgta    4500
cattactaaa caagggaaac tatgcagacc cattactaaa gaaatgtgag cccacctagc    4560
tagataattt tatctaaaag tattaaatta tattttgcac aacatacaaa agttaaattt    4620
gttgtacaat gcatattatt ttctaaaaaa aatgcaaaaa taatttggag aaattttata    4680
aggtagtcca cggtaatta atccatttct ataatgcaaa tagagtctca ctaatagcag    4740
gtctcctttt ctcgttttga agaatacaga tggaacattt tctacctacg aatgcaaacg    4800
gacattcgct tggttagagg ttagtgtatat tcctttaaag ttttataaca tggtacaatt    4860
aagatgaaat atcatttttg tattgtatga cttgtccatg agaacaaggt attgggattg    4920
aataagaagt caaagaaaa ccaaatacaa caatgatata ttaattgtaa ttcttatggt    4980
cattttgcat ttctctttca tacccaagaa attttttctc ctgaacaata agtttggata    5040
accctatccc ctttaacaaa atatctcttc tacgagctag gttctcaacc cttctgagag    5100
ttttcggaac attgtcgtgg actatccgta agacaaaaaa cacctacttc ataaattatc    5160
tttacttcta tattcaaata ttcattttcg cgaactgact tgatatacat aataatggtc    5220
agatctgttg aatgcacatc atctgtggtt gatgctctca tattatttaa agagacgaat    5280
ccacgatatc gaagagcaga gatagataaa tgcattgaag aagctgttgt atttattgag    5340
aacagtcaaa ataaggatgg ttcatggtaa gtgacatgat ataaattatg cgttacaata    5400
acttttactt ttgattaaat ttgaaaattt attacttctt gtatctcata ggtatggctc    5460
atggggtata tgtttcgcat atggatgcat gtttgcagta agggcgttgg ttgctacagg    5520
aaaaacctac gacaattgtg cttctatcag gaaatcatgc aaatttgtct tatcaaagca    5580
acaaacaaca ggtggatggg gtgaagacta tcttctagt gacaatgggg taatataaca    5640 aactactta cccctataac atttttactaa tggtaaatca atccatcat gattattcat    5700 agatttaagt catacatgat atagtaaaca tagaaattga tactagttga gagttttgtt    5760
gttctataaa tatactagtt gagagttcag tagttctata agccatgcat ggaattacga    5820
aacattataa actcaacgca agatgatata gttgacaaat tttaaaaata tcatatgtct    5880
tgttaaaaaa aagatcctag ttatattttg agcatgaata tcttcaaata ttgtgtatat    5940
gtgagaaagg tgatgtttaa ttgcacaagg tacactaaat aaaatggtta atttgtgtat    6000
gcccaaaaaa gagagatata gaaagagcta aagtaaactt ttaattgaca catcttgttc    6060
```

```
ttaacattta tttttttatga aagtctcagt acattcacga tacctagcaa tatgaaaatt      6120
cattgattag acagaagata aaattgccat tccacaatta ttaaatcata tatgttaatt      6180 tttgccttt  tgcttatttt tgtcatgata atggatgcat aacaccatgt tttccaatgg      6240
tctcatctac taatctcaga tatcttaata cagcttggtc tacaactgtt acaccccagt      6300
tttgatgacc gtgtccacaa atacattata aactactact aatgacctaa cacaaaaaaa      6360
tgacgacaaa gacaaatatc caatagaagg atcttttgta ctgaacaaat gaagaaaatt      6420
gtacatatat attgtgtaat atttaatttg ttttcctttta gtgtactcca tccatgaaaa      6480
tgatattaaa tcaatatttg caatcatgcg gtcaaatctg ttcttctaga tgcgtaagct      6540
aaagtcatta tatgtatata tatattttca agaacacata ggcatgttgt gttttctaat      6600
cacgttttgt acaggaatat attgatagcg gtaggcctaa tgctgtgacc acctcatggg      6660
caatgttggc tttaatttat gctggacagg tttgtcaaat attttttcctt gtttgtctag      6720 aatatgaatt ttttattaaa aaggaaaagt tctcactatt cttgaatagt cgagttatct      6780
aacagaataa tttatatttt gtttttttaa taaggttgaa cgtgacccag taccactgta      6840
taatgctgca agacagctaa tgaatatgca gctagaaaca ggtgacttcc cccaacaggt      6900
aatatgtttc cgtcctacat gttttcaaac aaaaatgcaa agtaatctta agtttaattg      6960
aaactgatct tttgttaatg aaactcaatg tagaccttaa gggaacaacc agtagaaata      7020
aaatacttgt gaattgataa ctctggaaag tgtatgcatt aatgttggtg tgaatgtggt      7080
aaatgttggc attgcgtcat aatttttgca tcggtactta caaagtttaa ttaacactaa      7140
tctcttgtca gattcaatga tcattaaaaa ttaagatata acctccatct agcttcttac      7200
ttacagtttc accttggtaa taggaacaca tgggttgctt caactcctcc ttgaacttca      7260
actacgccaa ctaccgcaat ctataccga  ttatggctct  tggggaactt cgccgtcgac      7320
ttcttgcgat taagagctga                                                   7340

<210> SEQ ID NO 37
<211> LENGTH: 1944
<212> TYPE: DNA
<213> ORGANISM: Avena strigosa

<400> SEQUENCE: 37
ttcaaataaa aattacctga tctgacatga tcactggcta cgccgagatt ctacaaatat       60
ttctataagt agtttgtgga ttccaatata tatacgatt  ccgtaaagct ctcttaccga      120
tggtatgact ttagtagtaa caaaatcata ggcttcgagt gaagattggc taccaactgt      180
aatgtaagat tgttgtccaa gataagatac tcaagttaca gatgcactac tctaatacta      240
agagttattg atctatatta cggctcccgt accgtagaga tattgattct acgttcacct      300
tcttaaaagg agattcttgt acaatcaaaa caaatgggtc tagctacctt ggtcaatatg      360
tatttctatc ggtatttagt tataaaggag aggaatacag ataattttt  ttaactccat      420 agtacctcta ttgctttcag tataaagagt ttgatgcacg gttctctgta ctaataaatg      480
ttctattgtt gattgattct taaccgcatc ctatgcaatt ttaacctcaa aaaagtttca      540
cggtacaccg acttgcctta ctagccctac tgttttcttg agaaggatgt tcaaactttg      600
ggcttttgca tctaaaataa gacacacatc attttttggtt tattattcaa caatgtgtgg      660
gaaaagcata caacaatcaa ctcgatatac caccttcgcg gagggcctcc tctttaaatg      720
tctgggagta ctacacatat gtaaagatga tgcccactta caaagaacga ggacaccact      780
```

```
taaaccgggt gtacaaagta ctacacatat gtaaagacga ggccatagaa caagcaagag    840
caccaagata tttagatcca ctaaaatgca accacctcga tgtccataaa aaatgatggt    900
gacgcacaac actcaacaaa tatcgataaa aatgatagtg tcctagttgc acatcttcta    960
acatgttggt gtctattatg cacaagtggg catggaagca agtaaatatt gtgtactata   1020
gctactggtg actcgagtgt atctccaaga ctcgatagca acccgaagc ctcttcagct    1080 tgtccacata tcattgtgga atgttcacta cgactcgcca cgccaagcat aacctggata   1140
agccacgtgg gatatgagat ttcccgcagc ttccctctga gtgaggaggc agaactatac   1200
gcctcaacac gacgagccac ccctaaggc tagtcatagt gggagtaact tgggtagtaa    1260
catattccta catatattgc gaactaagca tttagatgac atgacatgca attaaatgat   1320
gagagagagt cttatgataa ctagctatgt taccataaca tcacacattt ctaaaaaaat   1380
aaatctatat tataataaat aaggttttgc atgataccac atctatgtta ttttgcacta   1440
tgaagatagt aacttagact agtaacatat acatgttact actctaagtt actccccaca   1500
atgaccagcc taacaccttt tgtactgttt tgcacatttg cagtttactt tttcttaggt   1560
gaagagaaaa cacaagacat aatttttaata tttcaacttc attacgtgct ggtgcaaata   1620 attttttacgg tgcaattttc gacatgattt attgtatatt tacagaaatt tatgctccaa   1680
atttgtttgg taccttcagt attagtttct ggacattgta catattatgt tgccgtataa   1740
gctgagctag aaggatcatt agtgtaattc catatatatc taaatgtacc tgtggaatca   1800
catttgagga agttccaatg atgccctttt tgccctgcac acgcatatat aagaacccctt  1860 tgcccgcagc atagagctag tactagctag tatcccattg cttgttttcc tcgcatacac   1920
tgcccgttgt tggtgcgcac catg                                          1944

<210> SEQ ID NO 38
<211> LENGTH: 14
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..(3)
<223> OTHER INFORMATION: n is a or c or g or t
<220> FEATURE:
<221> NAME/KEY: misc_feature
<222> LOCATION: (12)..(14)
<223> OTHER INFORMATION: n is a or c or g or t

<400> SEQUENCE: 38
nnncaattat tnnn                                                       14

<210> SEQ ID NO 39
<211> LENGTH: 11
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (2)..(3)
<223> OTHER INFORMATION: n is a or c or g or t
<220> FEATURE:
<221> NAME/KEY: misc_feature
<222> LOCATION: (9)..(11)
<223> OTHER INFORMATION: n is a or c or g or t

<400> SEQUENCE: 39
annwaaagnn n                                                          11
```

```
<210> SEQ ID NO 40
<211> LENGTH: 12
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..(3)
<223> OTHER INFORMATION: n is a or c or g or t
<220> FEATURE:
<221> NAME/KEY: misc_feature
<222> LOCATION: (10)..()
<223> OTHER INFORMATION: n is a or c or g or t

<400> SEQUENCE: 40
nnnsacgtgn cm                                                              12

<210> SEQ ID NO 41
<211> LENGTH: 11
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..()
<223> OTHER INFORMATION: n is a or c or g or t
<220> FEATURE:
<221> NAME/KEY: misc_feature
<222> LOCATION: (3)..()
<223> OTHER INFORMATION: n is a or c or g or t
<220> FEATURE:
<221> NAME/KEY: misc_feature
<222> LOCATION: (9)..()
<223> OTHER INFORMATION: n is a or c or g or t
<220> FEATURE:
<221> NAME/KEY: misc_feature
<222> LOCATION: (11)..()
<223> OTHER INFORMATION: n is a or c or g or t

<400> SEQUENCE: 41
nwnwaaagng n                                                               11

<210> SEQ ID NO 42
<211> LENGTH: 14
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (5)..()
<223> OTHER INFORMATION: n is a or c or g or t
<220> FEATURE:
<221> NAME/KEY: misc_feature
<222> LOCATION: (14)..()
<223> OTHER INFORMATION: n is a or c or g or t

<400> SEQUENCE: 42
kwrtngttaa wwwn                                                            14

<210> SEQ ID NO 43
<211> LENGTH: 11
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..()
```

<223> OTHER INFORMATION: n is a or c or g or t
<220> FEATURE:
<221> NAME/KEY: misc_feature
<222> LOCATION: (3)..()
<223> OTHER INFORMATION: n is a or c or g or t
<220> FEATURE:
<221> NAME/KEY: misc_feature
<222> LOCATION: (9)..()
<223> OTHER INFORMATION: n is a or c or g or t
<220> FEATURE:
<221> NAME/KEY: misc_feature
<222> LOCATION: (11)..()
<223> OTHER INFORMATION: n is a or c or g or t

<400> SEQUENCE: 43
ncnctttwnw n                                                11

<210> SEQ ID NO 44
<211> LENGTH: 11
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..(3)
<223> OTHER INFORMATION: n is a or c or g or t
<220> FEATURE:
<221> NAME/KEY: misc_feature
<222> LOCATION: (9)..(10)
<223> OTHER INFORMATION: n is a or c or g or t

<400> SEQUENCE: 44
nnnctttwnn t                                                11

<210> SEQ ID NO 45
<211> LENGTH: 13
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..(2)
<223> OTHER INFORMATION: n is a or c or g or t
<220> FEATURE:
<221> NAME/KEY: misc_feature
<222> LOCATION: (11)..(13)
<223> OTHER INFORMATION: n is a or c or g or t

<400> SEQUENCE: 45
nnaataattg nnn                                              13

<210> SEQ ID NO 46
<211> LENGTH: 14
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..()
<223> OTHER INFORMATION: n is a or c or g or t
<220> FEATURE:
<221> NAME/KEY: misc_feature
<222> LOCATION: (10)..()
<223> OTHER INFORMATION: n is a or c or g or t

<400> SEQUENCE: 46
nwwwttaacn aywm                                             14

```
<210> SEQ ID NO 47
<211> LENGTH: 13
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..()
<223> OTHER INFORMATION: n is a or c or g or t
<220> FEATURE:
<221> NAME/KEY: misc_feature
<222> LOCATION: (12)..(13)
<223> OTHER INFORMATION: n is a or c or g or t

<400> SEQUENCE: 47
ntaacsgttt tnn                                                          13

<210> SEQ ID NO 48
<211> LENGTH: 12
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (3)..(3)
<223> OTHER INFORMATION: n is a or c or g or t
<220> FEATURE:
<221> NAME/KEY: misc_feature
<222> LOCATION: (10)..(12)
<223> OTHER INFORMATION: n is a or c or g or t

<400> SEQUENCE: 48
kgncacgtsn nn                                                           12

<210> SEQ ID NO 49
<211> LENGTH: 14
<212> TYPE: DNA
<213> ORGANISM: Artificial
<220> FEATURE:
<223> OTHER INFORMATION: Putative transcription factor binding site
<220> FEATURE:
<221> NAME/KEY: misc_feature
<222> LOCATION: (1)..(3)
<223> OTHER INFORMATION: n is a or c or g or t
<220> FEATURE:
<221> NAME/KEY: misc_feature
<222> LOCATION: (12)..(14)
<223> OTHER INFORMATION: n is a or c or g or t

<400> SEQUENCE: 49
nnnaataatt gnnn                                                         14

<210> SEQ ID NO 50
<211> LENGTH: 7
<212> TYPE: PRT
<213> ORGANISM: Avena strigosa

<400> SEQUENCE: 50

Lys Ser Asn Asn Gly Phe Leu
1               5

<210> SEQ ID NO 51
<211> LENGTH: 10
<212> TYPE: PRT
<213> ORGANISM: Avena strigosa

<400> SEQUENCE: 51

Val Trp Glu Tyr Asp Ala Asp Ala Gly Thr
```

<210> SEQ ID NO 52
<211> LENGTH: 8
<212> TYPE: PRT
<213> ORGANISM: Avena strigosa

<400> SEQUENCE: 52

Arg Val Arg Ala Glu Phe Thr Lys
1               5

<210> SEQ ID NO 53
<211> LENGTH: 8
<212> TYPE: PRT
<213> ORGANISM: Avena strigosa

<400> SEQUENCE: 53

Pro Ala Asn Ile Pro Thr Glu Ala
1               5

<210> SEQ ID NO 54
<211> LENGTH: 13
<212> TYPE: PRT
<213> ORGANISM: Avena strigosa

<400> SEQUENCE: 54

Lys Ser Thr Glu Val Thr His Glu Thr Ile Tyr Glu Ser
1               5                   10

<210> SEQ ID NO 55
<211> LENGTH: 8
<212> TYPE: PRT
<213> ORGANISM: Avena strigosa

<400> SEQUENCE: 55

Ile Met Pro Ile Asn Ile Phe Ser
1               5

<210> SEQ ID NO 56
<211> LENGTH: 8
<212> TYPE: PRT
<213> ORGANISM: Avena strigosa

<400> SEQUENCE: 56

Arg Ser Leu Asp Thr Phe Leu Ser
1               5

<210> SEQ ID NO 57
<211> LENGTH: 16
<212> TYPE: PRT
<213> ORGANISM: Avena strigosa

<400> SEQUENCE: 57

Asn Gln Gln Asn Glu Asp Gly Gly Trp Gly Lys Met Val Leu Gly Pro
1               5                   10                  15

<210> SEQ ID NO 58
<211> LENGTH: 10
<212> TYPE: PRT
<213> ORGANISM: Avena strigosa

<400> SEQUENCE: 58

Gly Ser Cys Met Asn Tyr Ala Thr Leu Met
1               5                   10

<210> SEQ ID NO 59
<211> LENGTH: 12
<212> TYPE: PRT
<213> ORGANISM: Avena strigosa

<400> SEQUENCE: 59

Lys Arg Asn Gly Asp His Lys Asp Ala Leu Glu Lys
1               5                   10

<210> SEQ ID NO 60
<211> LENGTH: 10
<212> TYPE: PRT
<213> ORGANISM: Avena strigosa

<400> SEQUENCE: 60

Ser His Gly Thr Ala Thr Ala Ile Pro Gln
1               5                   10

<210> SEQ ID NO 61
<211> LENGTH: 10
<212> TYPE: PRT
<213> ORGANISM: Avena strigosa

<400> SEQUENCE: 61

Ile Ile Pro Glu Leu Trp Leu Val Pro His
1               5                   10

<210> SEQ ID NO 62
<211> LENGTH: 14
<212> TYPE: PRT
<213> ORGANISM: Avena strigosa

<400> SEQUENCE: 62

Arg Phe Trp Cys Phe Thr Arg Leu Ile Tyr Met Ser Met Ala
1               5                   10

<210> SEQ ID NO 63
<211> LENGTH: 13
<212> TYPE: PRT
<213> ORGANISM: Avena strigosa

<400> SEQUENCE: 63

Ala Leu Arg Gln Asp Leu Tyr Ser Ile Pro Tyr Cys Asn
1               5                   10

<210> SEQ ID NO 64
<211> LENGTH: 8
<212> TYPE: PRT
<213> ORGANISM: Avena strigosa

<400> SEQUENCE: 64

Trp Asp Lys Ala Arg Asp Tyr Cys
1               5

<210> SEQ ID NO 65
<211> LENGTH: 14
<212> TYPE: PRT
<213> ORGANISM: Avena strigosa

<400> SEQUENCE: 65

Arg Ser Arg Ala Gln Asp Leu Ile Ser Gly Cys Leu Thr Lys
1               5                   10

<210> SEQ ID NO 66

```
<211> LENGTH: 11
<212> TYPE: PRT
<213> ORGANISM: Avena strigosa

<400> SEQUENCE: 66

Ile Leu Asn Trp Trp Pro Ala Asn Lys Leu Arg
1               5                   10

<210> SEQ ID NO 67
<211> LENGTH: 10
<212> TYPE: PRT
<213> ORGANISM: Avena strigosa

<400> SEQUENCE: 67

Asp Arg Ala Leu Thr Asn Leu Met Glu His
1               5                   10

<210> SEQ ID NO 68
<211> LENGTH: 10
<212> TYPE: PRT
<213> ORGANISM: Avena strigosa

<400> SEQUENCE: 68

Ser Thr Lys Tyr Val Gly Ile Cys Pro Ile
1               5                   10

<210> SEQ ID NO 69
<211> LENGTH: 12
<212> TYPE: PRT
<213> ORGANISM: Avena strigosa

<400> SEQUENCE: 69

Ile Cys Cys Trp Val Glu Asn Pro Asn Ser Pro Glu
1               5                   10

<210> SEQ ID NO 70
<211> LENGTH: 9
<212> TYPE: PRT
<213> ORGANISM: Avena strigosa

<400> SEQUENCE: 70

Ala Gln Val Tyr Asp Gly Cys His Ser
1               5

<210> SEQ ID NO 71
<211> LENGTH: 10
<212> TYPE: PRT
<213> ORGANISM: Avena strigosa

<400> SEQUENCE: 71

Glu Leu Ala Phe Ile Ile His Ala Tyr Cys
1               5                   10

<210> SEQ ID NO 72
<211> LENGTH: 9
<212> TYPE: PRT
<213> ORGANISM: Avena strigosa

<400> SEQUENCE: 72

Ser Thr Asp Leu Thr Ser Glu Phe Ile
1               5

<210> SEQ ID NO 73
<211> LENGTH: 10
<212> TYPE: PRT
```

<210> SEQ ID NO 73 (implied continuation)

<213> ORGANISM: Avena strigosa

<400> SEQUENCE: 73

Leu Phe Asn His Pro Asn His Glu Ser Tyr
1               5                   10

<210> SEQ ID NO 74
<211> LENGTH: 9
<212> TYPE: PRT
<213> ORGANISM: Avena strigosa

<400> SEQUENCE: 74

Leu Ser Ser Val Asp Asn Gly Trp Ser
1               5

<210> SEQ ID NO 75
<211> LENGTH: 14
<212> TYPE: PRT
<213> ORGANISM: Avena strigosa

<400> SEQUENCE: 75

Lys Ile Ser Ala Asp Leu Val Gly Asp Pro Ile Lys Gln Asp
1               5                   10

<210> SEQ ID NO 76
<211> LENGTH: 11
<212> TYPE: PRT
<213> ORGANISM: Avena strigosa

<400> SEQUENCE: 76

Ile Asp Cys Ile Leu Ser Phe Met Asn Thr Asp
1               5                   10

<210> SEQ ID NO 77
<211> LENGTH: 12
<212> TYPE: PRT
<213> ORGANISM: Avena strigosa

<400> SEQUENCE: 77

Thr Phe Ser Thr Tyr Glu Cys Lys Arg Thr Phe Ala
1               5                   10

<210> SEQ ID NO 78
<211> LENGTH: 8
<212> TYPE: PRT
<213> ORGANISM: Avena strigosa

<400> SEQUENCE: 78

Asn Pro Ser Glu Ser Phe Arg Asn
1               5

<210> SEQ ID NO 79
<211> LENGTH: 7
<212> TYPE: PRT
<213> ORGANISM: Avena strigosa

<400> SEQUENCE: 79

Val Val Asp Ala Leu Ile Leu
1               5

<210> SEQ ID NO 80
<211> LENGTH: 9
<212> TYPE: PRT
<213> ORGANISM: Avena strigosa

<400> SEQUENCE: 80

Glu Thr Asn Pro Arg Tyr Arg Arg Ala
1               5

<210> SEQ ID NO 81
<211> LENGTH: 10
<212> TYPE: PRT
<213> ORGANISM: Avena strigosa

<400> SEQUENCE: 81

Asp Lys Cys Ile Glu Glu Ala Val Val Phe
1               5                   10

<210> SEQ ID NO 82
<211> LENGTH: 11
<212> TYPE: PRT
<213> ORGANISM: Avena strigosa

<400> SEQUENCE: 82

Cys Met Phe Ala Val Arg Ala Leu Val Ala Thr
1               5                   10

<210> SEQ ID NO 83
<211> LENGTH: 11
<212> TYPE: PRT
<213> ORGANISM: Avena strigosa

<400> SEQUENCE: 83

Asp Asn Cys Ala Ser Ile Arg Lys Ser Cys Lys
1               5                   10

<210> SEQ ID NO 84
<211> LENGTH: 8
<212> TYPE: PRT
<213> ORGANISM: Avena strigosa

<400> SEQUENCE: 84

Val Leu Ser Lys Gln Gln Thr Thr
1               5

<210> SEQ ID NO 85
<211> LENGTH: 26
<212> TYPE: PRT
<213> ORGANISM: Avena strigosa

<400> SEQUENCE: 85

Asp Tyr Leu Ser Ser Asp Asn Gly Glu Tyr Ile Asp Ser Asp Tyr Leu
1               5                   10                  15

Ser Ser Asp Asn Gly Glu Tyr Ile Asp Ser
            20                  25

<210> SEQ ID NO 86
<211> LENGTH: 9
<212> TYPE: PRT
<213> ORGANISM: Avena strigosa

<400> SEQUENCE: 86

Gly Arg Pro Asn Ala Val Thr Thr Ser
1               5

<210> SEQ ID NO 87
<211> LENGTH: 10
<212> TYPE: PRT
<213> ORGANISM: Avena strigosa

```
<400> SEQUENCE: 87

Tyr Ala Gly Gln Val Glu Arg Asp Pro Val
1               5                   10

<210> SEQ ID NO 88
<211> LENGTH: 14
<212> TYPE: PRT
<213> ORGANISM: Avena strigosa

<400> SEQUENCE: 88

Tyr Asn Ala Ala Arg Gln Leu Met Asn Met Gln Leu Glu Thr
1               5                   10

<210> SEQ ID NO 89
<211> LENGTH: 13
<212> TYPE: PRT
<213> ORGANISM: Avena strigosa

<400> SEQUENCE: 89

Cys Phe Asn Ser Ser Leu Asn Phe Asn Tyr Ala Asn Tyr
1               5                   10

<210> SEQ ID NO 90
<211> LENGTH: 16
<212> TYPE: PRT
<213> ORGANISM: Avena strigosa

<400> SEQUENCE: 90

Ile Met Ala Leu Gly Glu Leu Arg Arg Arg Leu Leu Ala Ile Lys Ser
1               5                   10                  15

<210> SEQ ID NO 91
<211> LENGTH: 21
<212> TYPE: DNA
<213> ORGANISM: Artificial
<220> FEATURE:
<223> OTHER INFORMATION: Primer

<400> SEQUENCE: 91
aagtcgaaca atggcttcct t                                              21

<210> SEQ ID NO 92
<211> LENGTH: 28
<212> TYPE: DNA
<213> ORGANISM: Artificial
<220> FEATURE:
<223> OTHER INFORMATION: Primer

<400> SEQUENCE: 92
gtgggagtac gacgccgatg ccggcacg                                       28

<210> SEQ ID NO 93
<211> LENGTH: 24
<212> TYPE: DNA
<213> ORGANISM: Artificial
<220> FEATURE:
<223> OTHER INFORMATION: Primer

<400> SEQUENCE: 93
agggtgcgtg cggaattcac aaag                                           24

<210> SEQ ID NO 94
<211> LENGTH: 24
<212> TYPE: DNA
```

<213> ORGANISM: Artificial
<220> FEATURE:
<223> OTHER INFORMATION: Primer

<400> SEQUENCE: 94
ccggcgaata ttccgacaga agcc                                    24

<210> SEQ ID NO 95
<211> LENGTH: 39
<212> TYPE: DNA
<213> ORGANISM: Artificial
<220> FEATURE:
<223> OTHER INFORMATION: Primer

<400> SEQUENCE: 95
aagagtacag aggtcactca cgagactatc tacgaatca                    39

<210> SEQ ID NO 96
<211> LENGTH: 24
<212> TYPE: DNA
<213> ORGANISM: Artificial
<220> FEATURE:
<223> OTHER INFORMATION: Primer

<400> SEQUENCE: 96
attatgccta tcaatatatt ctct                                    24

<210> SEQ ID NO 97
<211> LENGTH: 24
<212> TYPE: DNA
<213> ORGANISM: Artificial
<220> FEATURE:
<223> OTHER INFORMATION: Primer

<400> SEQUENCE: 97
agagaatata ttgataggca taat                                    24

<210> SEQ ID NO 98
<211> LENGTH: 48
<212> TYPE: DNA
<213> ORGANISM: Artificial
<220> FEATURE:
<223> OTHER INFORMATION: Primer

<400> SEQUENCE: 98
aatcaacaga atgaagatgg tggttgggga aaaatggttc ttggccca          48

<210> SEQ ID NO 99
<211> LENGTH: 30
<212> TYPE: DNA
<213> ORGANISM: Artificial
<220> FEATURE:
<223> OTHER INFORMATION: Primer

<400> SEQUENCE: 99
ggatcgtgta tgaattatgc aaccttaatg                              30

<210> SEQ ID NO 100
<211> LENGTH: 36
<212> TYPE: DNA
<213> ORGANISM: Artificial
<220> FEATURE:
<223> OTHER INFORMATION: Primer

<400> SEQUENCE: 100
aagcgaaatg gtgatcataa ggatgcattg gaaaaa                       36

```
<210> SEQ ID NO 101
<211> LENGTH: 30
<212> TYPE: DNA
<213> ORGANISM: Artificial
<220> FEATURE:
<223> OTHER INFORMATION: Primer

<400> SEQUENCE: 101
tctcatggaa ctgcaactgc aataccacag                                    30

<210> SEQ ID NO 102
<211> LENGTH: 30
<212> TYPE: DNA
<213> ORGANISM: Artificial
<220> FEATURE:
<223> OTHER INFORMATION: Primer

<400> SEQUENCE: 102
attatacctg aattgtggtt ggttccacat                                    30

<210> SEQ ID NO 103
<211> LENGTH: 42
<212> TYPE: DNA
<213> ORGANISM: Artificial
<220> FEATURE:
<223> OTHER INFORMATION: Primer

<400> SEQUENCE: 103 cgttttggt gttttacccg gttgatatac atgtcaatgg ca                       42

<210> SEQ ID NO 104
<211> LENGTH: 39
<212> TYPE: DNA
<213> ORGANISM: Artificial
<220> FEATURE:
<223> OTHER INFORMATION: Primer

<400> SEQUENCE: 104
gctctgcgac aagacctcta tagtatacct tactgcaac                          39

<210> SEQ ID NO 105
<211> LENGTH: 24
<212> TYPE: DNA
<213> ORGANISM: Artificial
<220> FEATURE:
<223> OTHER INFORMATION: Primer

<400> SEQUENCE: 105
tgggacaagg cgcgtgatta ttgt                                          24

<210> SEQ ID NO 106
<211> LENGTH: 42
<212> TYPE: DNA
<213> ORGANISM: Artificial
<220> FEATURE:
<223> OTHER INFORMATION: Primer

<400> SEQUENCE: 106
cgctcacggg cacaagatct tatatctggt tgcctaacga aa                      42

<210> SEQ ID NO 107
<211> LENGTH: 33
<212> TYPE: DNA
<213> ORGANISM: Artificial
<220> FEATURE:
```

```
<223> OTHER INFORMATION: Primer

<400> SEQUENCE: 107
attttgaatt ggtggccagc aaacaagcta aga                                    33

<210> SEQ ID NO 108
<211> LENGTH: 30
<212> TYPE: DNA
<213> ORGANISM: Artificial
<220> FEATURE:
<223> OTHER INFORMATION: Primer

<400> SEQUENCE: 108
gatagagctt taactaacct catggagcat                                        30

<210> SEQ ID NO 109
<211> LENGTH: 30
<212> TYPE: DNA
<213> ORGANISM: Artificial
<220> FEATURE:
<223> OTHER INFORMATION: Primer

<400> SEQUENCE: 109
tcaaccaaat atgtgggcat ttgccctatt                                        30

<210> SEQ ID NO 110
<211> LENGTH: 36
<212> TYPE: DNA
<213> ORGANISM: Artificial
<220> FEATURE:
<223> OTHER INFORMATION: Primer

<400> SEQUENCE: 110
atttgttgtt gggtagaaaa cccaaattcg cctgaa                                 36

<210> SEQ ID NO 111
<211> LENGTH: 27
<212> TYPE: DNA
<213> ORGANISM: Artificial
<220> FEATURE:
<223> OTHER INFORMATION: Primer

<400> SEQUENCE: 111
gcacaggtat atgatggatg tcatagc                                           27

<210> SEQ ID NO 112
<211> LENGTH: 30
<212> TYPE: DNA
<213> ORGANISM: Artificial
<220> FEATURE:
<223> OTHER INFORMATION: Primer

<400> SEQUENCE: 112
gaactagcgt tcataattca tgcctattgt                                        30

<210> SEQ ID NO 113
<211> LENGTH: 27
<212> TYPE: DNA
<213> ORGANISM: Artificial
<220> FEATURE:
<223> OTHER INFORMATION: Primer

<400> SEQUENCE: 113
tccacggatc ttactagcga gtttatc                                           27
```

<210> SEQ ID NO 114
<211> LENGTH: 30
<212> TYPE: DNA
<213> ORGANISM: Artificial
<220> FEATURE:
<223> OTHER INFORMATION: Primer

<400> SEQUENCE: 114
cttttcaacc acccaaatca tgaaagctat                               30

<210> SEQ ID NO 115
<211> LENGTH: 27
<212> TYPE: DNA
<213> ORGANISM: Artificial
<220> FEATURE:
<223> OTHER INFORMATION: Primer

<400> SEQUENCE: 115
ctttcaagtg tagataatgg ttggtct                                  27

<210> SEQ ID NO 116
<211> LENGTH: 42
<212> TYPE: DNA
<213> ORGANISM: Artificial
<220> FEATURE:
<223> OTHER INFORMATION: Primer

<400> SEQUENCE: 116
aagatatccg ctgaccttgt tggcgatcca ataaaacaag ac                 42

<210> SEQ ID NO 117
<211> LENGTH: 33
<212> TYPE: DNA
<213> ORGANISM: Artificial
<220> FEATURE:
<223> OTHER INFORMATION: Primer

<400> SEQUENCE: 117
attgattgca tcctatcttt catgaataca gat                           33

<210> SEQ ID NO 118
<211> LENGTH: 36
<212> TYPE: DNA
<213> ORGANISM: Artificial
<220> FEATURE:
<223> OTHER INFORMATION: Primer

<400> SEQUENCE: 118
acattttcta cctacgaatg caaacggaca ttcgct                        36

<210> SEQ ID NO 119
<211> LENGTH: 24
<212> TYPE: DNA
<213> ORGANISM: Artificial
<220> FEATURE:
<223> OTHER INFORMATION: Primer

<400> SEQUENCE: 119
aacccttctg agagttttcg gaac                                     24

<210> SEQ ID NO 120
<211> LENGTH: 21
<212> TYPE: DNA
<213> ORGANISM: Artificial
<220> FEATURE:
<223> OTHER INFORMATION: Primer

```
<400> SEQUENCE: 120
gtggttgatg ctctcatatt a                                              21

<210> SEQ ID NO 121
<211> LENGTH: 27
<212> TYPE: DNA
<213> ORGANISM: Artificial
<220> FEATURE:
<223> OTHER INFORMATION: Primer

<400> SEQUENCE: 121
gagacgaatc cacgatatcg aagagca                                        27

<210> SEQ ID NO 122
<211> LENGTH: 30
<212> TYPE: DNA
<213> ORGANISM: Artificial
<220> FEATURE:
<223> OTHER INFORMATION: Primer

<400> SEQUENCE: 122
gataaatgca ttgaagaagc tgttgtattt                                     30

<210> SEQ ID NO 123
<211> LENGTH: 33
<212> TYPE: DNA
<213> ORGANISM: Artificial
<220> FEATURE:
<223> OTHER INFORMATION: Primer

<400> SEQUENCE: 123
tgcatgtttg cagtaagggc gttggttgct aca                                 33

<210> SEQ ID NO 124
<211> LENGTH: 33
<212> TYPE: DNA
<213> ORGANISM: Artificial
<220> FEATURE:
<223> OTHER INFORMATION: Primer

<400> SEQUENCE: 124
gacaattgtg cttctatcag gaaatcatgc aaa                                 33

<210> SEQ ID NO 125
<211> LENGTH: 24
<212> TYPE: DNA
<213> ORGANISM: Artificial
<220> FEATURE:
<223> OTHER INFORMATION: Primer

<400> SEQUENCE: 125
gtcttatcaa agcaacaaac aaca                                           24

<210> SEQ ID NO 126
<211> LENGTH: 39
<212> TYPE: DNA
<213> ORGANISM: Artificial
<220> FEATURE:
<223> OTHER INFORMATION: Primer

<400> SEQUENCE: 126
gactatcttt ctagtgacaa tgggaatat attgatagc                            39

<210> SEQ ID NO 127
<211> LENGTH: 27
```

<212> TYPE: DNA
<213> ORGANISM: Artificial
<220> FEATURE:
<223> OTHER INFORMATION: Primer

<400> SEQUENCE: 127
ggtaggccta atgctgtgac cacctca                                    27

<210> SEQ ID NO 128
<211> LENGTH: 30
<212> TYPE: DNA
<213> ORGANISM: Artificial
<220> FEATURE:
<223> OTHER INFORMATION: Primer

<400> SEQUENCE: 128
tatgctggac aggttgaacg tgacccagta                                 30

<210> SEQ ID NO 129
<211> LENGTH: 42
<212> TYPE: DNA
<213> ORGANISM: Artificial
<220> FEATURE:
<223> OTHER INFORMATION: Primer

<400> SEQUENCE: 129
tataatgctg caagacagct aatgaatatg cagctagaaa ca                   42

<210> SEQ ID NO 130
<211> LENGTH: 39
<212> TYPE: DNA
<213> ORGANISM: Artificial
<220> FEATURE:
<223> OTHER INFORMATION: Primer

<400> SEQUENCE: 130
tgcttcaact cctccttgaa cttcaactac gccaactac                       39

<210> SEQ ID NO 131
<211> LENGTH: 51
<212> TYPE: DNA
<213> ORGANISM: Artificial
<220> FEATURE:
<223> OTHER INFORMATION: Primer

<400> SEQUENCE: 131
attatggctc ttggggaact tcgccgtcga cttcttgcga ttaagagctg a         51

<210> SEQ ID NO 132
<211> LENGTH: 21
<212> TYPE: DNA
<213> ORGANISM: Artificial
<220> FEATURE:
<223> OTHER INFORMATION: Primer

<400> SEQUENCE: 132
aaggaagcca ttgttcgact t                                          21

<210> SEQ ID NO 133
<211> LENGTH: 28
<212> TYPE: DNA
<213> ORGANISM: Artificial
<220> FEATURE:
<223> OTHER INFORMATION: Primer

<400> SEQUENCE: 133

-continued

| cgtgccggca tcggcgtcgt actcccac | 28 |

<210> SEQ ID NO 134
<211> LENGTH: 24
<212> TYPE: DNA
<213> ORGANISM: Artificial
<220> FEATURE:
<223> OTHER INFORMATION: Primer

<400> SEQUENCE: 134

| ctttgtgaat tccgcacgca ccct | 24 |

<210> SEQ ID NO 135
<211> LENGTH: 24
<212> TYPE: DNA
<213> ORGANISM: Artificial
<220> FEATURE:
<223> OTHER INFORMATION: Primer

<400> SEQUENCE: 135

| ggcttctgtc ggaatattcg ccgg | 24 |

<210> SEQ ID NO 136
<211> LENGTH: 39
<212> TYPE: DNA
<213> ORGANISM: Artificial
<220> FEATURE:
<223> OTHER INFORMATION: Primer

<400> SEQUENCE: 136

| tgattcgtag atagtctcgt gagtgacctc tgtactctt | 39 |

<210> SEQ ID NO 137
<211> LENGTH: 24
<212> TYPE: DNA
<213> ORGANISM: Artificial
<220> FEATURE:
<223> OTHER INFORMATION: Primer

<400> SEQUENCE: 137

| agagaatata ttgataggca taat | 24 |

<210> SEQ ID NO 138
<211> LENGTH: 24
<212> TYPE: DNA
<213> ORGANISM: Artificial
<220> FEATURE:
<223> OTHER INFORMATION: Primer

<400> SEQUENCE: 138

| attatgccta tcaatatatt ctct | 24 |

<210> SEQ ID NO 139
<211> LENGTH: 48
<212> TYPE: DNA
<213> ORGANISM: Artificial
<220> FEATURE:
<223> OTHER INFORMATION: Primer

<400> SEQUENCE: 139

| tgggccaaga accattttc cccaaccacc atcttcattc tgttgatt | 48 |

<210> SEQ ID NO 140
<211> LENGTH: 30
<212> TYPE: DNA
<213> ORGANISM: Artificial

```
<220> FEATURE:
<223> OTHER INFORMATION: Primer

<400> SEQUENCE: 140
cattaaggtt gcataattca tacacgatcc                                    30

<210> SEQ ID NO 141
<211> LENGTH: 36
<212> TYPE: DNA
<213> ORGANISM: Artificial
<220> FEATURE:
<223> OTHER INFORMATION: Primer

<400> SEQUENCE: 141
tttttccaat gcatccttat gatcaccatt tcgctt                             36

<210> SEQ ID NO 142
<211> LENGTH: 30
<212> TYPE: DNA
<213> ORGANISM: Artificial
<220> FEATURE:
<223> OTHER INFORMATION: Primer

<400> SEQUENCE: 142
ctgtggtatt gcagttgcag ttccatgaga                                    30

<210> SEQ ID NO 143
<211> LENGTH: 30
<212> TYPE: DNA
<213> ORGANISM: Artificial
<220> FEATURE:
<223> OTHER INFORMATION: Primer

<400> SEQUENCE: 143
atgtggaacc aaccacaatt caggtataat                                    30

<210> SEQ ID NO 144
<211> LENGTH: 42
<212> TYPE: DNA
<213> ORGANISM: Artificial
<220> FEATURE:
<223> OTHER INFORMATION: Primer

<400> SEQUENCE: 144
tgccattgac atgtatatca accgggtaaa acaccaaaaa cg                      42

<210> SEQ ID NO 145
<211> LENGTH: 39
<212> TYPE: DNA
<213> ORGANISM: Artificial
<220> FEATURE:
<223> OTHER INFORMATION: Primer

<400> SEQUENCE: 145
gttgcagtaa ggtatactat agaggtcttg tcgcagagc                          39

<210> SEQ ID NO 146
<211> LENGTH: 24
<212> TYPE: DNA
<213> ORGANISM: Artificial
<220> FEATURE:
<223> OTHER INFORMATION: Primer

<400> SEQUENCE: 146
acaataatca cgcgccttgt ccca                                          24
```

-continued

<210> SEQ ID NO 147
<211> LENGTH: 42
<212> TYPE: DNA
<213> ORGANISM: Artificial
<220> FEATURE:
<223> OTHER INFORMATION: Primer

<400> SEQUENCE: 147
tttcgttagg caaccagata taagatcttg tgcccgtgag cg                           42

<210> SEQ ID NO 148
<211> LENGTH: 33
<212> TYPE: DNA
<213> ORGANISM: Artificial
<220> FEATURE:
<223> OTHER INFORMATION: Primer

<400> SEQUENCE: 148
tcttagcttg tttgctggcc accaattcaa aat                                    33

<210> SEQ ID NO 149
<211> LENGTH: 30
<212> TYPE: DNA
<213> ORGANISM: Artificial
<220> FEATURE:
<223> OTHER INFORMATION: Primer

<400> SEQUENCE: 149
atgctccatg aggttagtta aagctctatc                                        30

<210> SEQ ID NO 150
<211> LENGTH: 30
<212> TYPE: DNA
<213> ORGANISM: Artificial
<220> FEATURE:
<223> OTHER INFORMATION: Primer

<400> SEQUENCE: 150
aatagggcaa atgcccacat atttggttga                                        30

<210> SEQ ID NO 151
<211> LENGTH: 36
<212> TYPE: DNA
<213> ORGANISM: Artificial
<220> FEATURE:
<223> OTHER INFORMATION: Primer

<400> SEQUENCE: 151
ttcaggcgaa tttgggtttt ctacccaaca acaaat                                 36

<210> SEQ ID NO 152
<211> LENGTH: 27
<212> TYPE: DNA
<213> ORGANISM: Artificial
<220> FEATURE:
<223> OTHER INFORMATION: Primer

<400> SEQUENCE: 152
gctatgacat ccatcatata cctgtgc                                           27

<210> SEQ ID NO 153
<211> LENGTH: 30
<212> TYPE: DNA
<213> ORGANISM: Artificial
<220> FEATURE:
<223> OTHER INFORMATION: Primer

```
<400> SEQUENCE: 153
acaataggca tgaattatga acgctagttc                                    30

<210> SEQ ID NO 154
<211> LENGTH: 27
<212> TYPE: DNA
<213> ORGANISM: Artificial
<220> FEATURE:
<223> OTHER INFORMATION: Primer

<400> SEQUENCE: 154
gataaactcg ctagtaagat ccgtgga                                       27

<210> SEQ ID NO 155
<211> LENGTH: 30
<212> TYPE: DNA
<213> ORGANISM: Artificial
<220> FEATURE:
<223> OTHER INFORMATION: Primer

<400> SEQUENCE: 155
atagctttca tgatttgggt ggttgaaaag                                    30

<210> SEQ ID NO 156
<211> LENGTH: 27
<212> TYPE: DNA
<213> ORGANISM: Artificial
<220> FEATURE:
<223> OTHER INFORMATION: Primer

<400> SEQUENCE: 156
agaccaacca ttatctacac ttgaaag                                       27

<210> SEQ ID NO 157
<211> LENGTH: 42
<212> TYPE: DNA
<213> ORGANISM: Artificial
<220> FEATURE:
<223> OTHER INFORMATION: Primer

<400> SEQUENCE: 157
gtcttgtttt attggatcgc caacaaggtc agcggatatc tt                      42

<210> SEQ ID NO 158
<211> LENGTH: 33
<212> TYPE: DNA
<213> ORGANISM: Artificial
<220> FEATURE:
<223> OTHER INFORMATION: Primer

<400> SEQUENCE: 158
atctgtattc atgaaagata ggatgcaatc aat                                33

<210> SEQ ID NO 159
<211> LENGTH: 36
<212> TYPE: DNA
<213> ORGANISM: Artificial
<220> FEATURE:
<223> OTHER INFORMATION: Primer

<400> SEQUENCE: 159
agcgaatgtc cgtttgcatt cgtaggtaga aaatgt                             36

<210> SEQ ID NO 160
```

```
<211> LENGTH: 24
<212> TYPE: DNA
<213> ORGANISM: Artificial
<220> FEATURE:
<223> OTHER INFORMATION: Primer

<400> SEQUENCE: 160
gttccgaaaa ctctcagaag ggtt                                              24

<210> SEQ ID NO 161
<211> LENGTH: 21
<212> TYPE: DNA
<213> ORGANISM: Artificial
<220> FEATURE:
<223> OTHER INFORMATION: Primer

<400> SEQUENCE: 161
taatatgaga gcatcaacca c                                                 21

<210> SEQ ID NO 162
<211> LENGTH: 27
<212> TYPE: DNA
<213> ORGANISM: Artificial
<220> FEATURE:
<223> OTHER INFORMATION: Primer

<400> SEQUENCE: 162
tgctcttcga tatcgtggat tcgtctc                                           27

<210> SEQ ID NO 163
<211> LENGTH: 30
<212> TYPE: DNA
<213> ORGANISM: Artificial
<220> FEATURE:
<223> OTHER INFORMATION: Primer

<400> SEQUENCE: 163
aaatacaaca gcttcttcaa tgcatttatc                                        30

<210> SEQ ID NO 164
<211> LENGTH: 33
<212> TYPE: DNA
<213> ORGANISM: Artificial
<220> FEATURE:
<223> OTHER INFORMATION: Primer

<400> SEQUENCE: 164
tgtagcaacc aacgccctta ctgcaaacat gca                                    33

<210> SEQ ID NO 165
<211> LENGTH: 33
<212> TYPE: DNA
<213> ORGANISM: Artificial
<220> FEATURE:
<223> OTHER INFORMATION: Primer

<400> SEQUENCE: 165
tttgcatgat ttcctgatag aagcacaatt gtc                                    33

<210> SEQ ID NO 166
<211> LENGTH: 24
<212> TYPE: DNA
<213> ORGANISM: Artificial
<220> FEATURE:
<223> OTHER INFORMATION: Primer

<400> SEQUENCE: 166
```

```
tgttgtttgt tgctttgata agac                                          24

<210> SEQ ID NO 167
<211> LENGTH: 39
<212> TYPE: DNA
<213> ORGANISM: Artificial
<220> FEATURE:
<223> OTHER INFORMATION: Primer

<400> SEQUENCE: 167
gctatcaata tattccccat tgtcactaga aagatagtc                          39

<210> SEQ ID NO 168
<211> LENGTH: 27
<212> TYPE: DNA
<213> ORGANISM: Artificial
<220> FEATURE:
<223> OTHER INFORMATION: Primer

<400> SEQUENCE: 168
tgaggtggtc acagcattag gcctacc                                       27

<210> SEQ ID NO 169
<211> LENGTH: 30
<212> TYPE: DNA
<213> ORGANISM: Artificial
<220> FEATURE:
<223> OTHER INFORMATION: Primer

<400> SEQUENCE: 169
tactgggtca cgttcaacct gtccagcata                                    30

<210> SEQ ID NO 170
<211> LENGTH: 42
<212> TYPE: DNA
<213> ORGANISM: Artificial
<220> FEATURE:
<223> OTHER INFORMATION: Primer

<400> SEQUENCE: 170
tgtttctagc tgcatattca ttagctgtct tgcagcatta ta                      42

<210> SEQ ID NO 171
<211> LENGTH: 39
<212> TYPE: DNA
<213> ORGANISM: Artificial
<220> FEATURE:
<223> OTHER INFORMATION: Primer

<400> SEQUENCE: 171
gtagttggcg tagttgaagt tcaaggagga gttgaagca                          39

<210> SEQ ID NO 172
<211> LENGTH: 51
<212> TYPE: DNA
<213> ORGANISM: Artificial
<220> FEATURE:
<223> OTHER INFORMATION: Primer

<400> SEQUENCE: 172
tcagctctta atcgcaagaa gtcgacggcg aagttcccca agagccataa t             51

<210> SEQ ID NO 173
<211> LENGTH: 20
<212> TYPE: DNA
```

```
<213> ORGANISM: Artificial
<220> FEATURE:
<223> OTHER INFORMATION: Primer

<400> SEQUENCE: 173
aswskammaa trryttyvtw                                               20

<210> SEQ ID NO 174
<211> LENGTH: 18
<212> TYPE: DNA
<213> ORGANISM: Artificial
<220> FEATURE:
<223> OTHER INFORMATION: Primer

<400> SEQUENCE: 174
wsrrakaacm ggtwycag                                                 18

<210> SEQ ID NO 175
<211> LENGTH: 19
<212> TYPE: DNA
<213> ORGANISM: Artificial
<220> FEATURE:
<223> OTHER INFORMATION: Primer

<400> SEQUENCE: 175
kytmttywty mtkccdmyc                                                19

<210> SEQ ID NO 176
<211> LENGTH: 18
<212> TYPE: DNA
<213> ORGANISM: Artificial
<220> FEATURE:
<223> OTHER INFORMATION: Primer

<400> SEQUENCE: 176
kwcgctacat wtacwrtc                                                 18

<210> SEQ ID NO 177
<211> LENGTH: 20
<212> TYPE: DNA
<213> ORGANISM: Artificial
<220> FEATURE:
<223> OTHER INFORMATION: Primer

<400> SEQUENCE: 177
tggtgrtsww aasratgcmt                                               20

<210> SEQ ID NO 178
<211> LENGTH: 22
<212> TYPE: DNA
<213> ORGANISM: Artificial
<220> FEATURE:
<223> OTHER INFORMATION: Primer

<400> SEQUENCE: 178
kgatcthayt vrygarwttv kh                                            22

<210> SEQ ID NO 179
<211> LENGTH: 19
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (9)..()
<223> OTHER INFORMATION: n is a or c or g or t
```

```
<400> SEQUENCE: 179
aaarsyatny atcgycaca                                              19

<210> SEQ ID NO 180
<211> LENGTH: 18
<212> TYPE: DNA
<213> ORGANISM: Artificial
<220> FEATURE:
<223> OTHER INFORMATION: Primer

<400> SEQUENCE: 180
gartgcacwt catcdgyr                                               18

<210> SEQ ID NO 181
<211> LENGTH: 19
<212> TYPE: DNA
<213> ORGANISM: Artificial
<220> FEATURE:
<223> OTHER INFORMATION: Primer

<400> SEQUENCE: 181
ggaaaracmt acdacaayt                                              19

<210> SEQ ID NO 182
<211> LENGTH: 19
<212> TYPE: DNA
<213> ORGANISM: Artificial
<220> FEATURE:
<223> OTHER INFORMATION: Primer

<400> SEQUENCE: 182 yttycccaa caggaamwm                                               19

<210> SEQ ID NO 183
<211> LENGTH: 20
<212> TYPE: DNA
<213> ORGANISM: Artificial
<220> FEATURE:
<223> OTHER INFORMATION: Primer

<400> SEQUENCE: 183
taccgsaatm tatacccrwt                                             20

<210> SEQ ID NO 184
<211> LENGTH: 20
<212> TYPE: DNA
<213> ORGANISM: Artificial
<220> FEATURE:
<223> OTHER INFORMATION: Primer

<400> SEQUENCE: 184
wabraaryya ttkktmswst                                             20

<210> SEQ ID NO 185
<211> LENGTH: 18
<212> TYPE: DNA
<213> ORGANISM: Artificial
<220> FEATURE:
<223> OTHER INFORMATION: Primer

<400> SEQUENCE: 185
ctgrwacckg ttmtyysw                                               18

<210> SEQ ID NO 186
```

```
<211> LENGTH: 19
<212> TYPE: DNA
<213> ORGANISM: Artificial
<220> FEATURE:
<223> OTHER INFORMATION: Primer

<400> SEQUENCE: 186
grkhggmakr awraakarm                                               19

<210> SEQ ID NO 187
<211> LENGTH: 18
<212> TYPE: DNA
<213> ORGANISM: Artificial
<220> FEATURE:
<223> OTHER INFORMATION: Primer

<400> SEQUENCE: 187
gaywgtawat gtagcgwm                                                18

<210> SEQ ID NO 188
<211> LENGTH: 20
<212> TYPE: DNA
<213> ORGANISM: Artificial
<220> FEATURE:
<223> OTHER INFORMATION: Primer

<400> SEQUENCE: 188
akgcatystt wwsaycacca                                              20

<210> SEQ ID NO 189
<211> LENGTH: 22
<212> TYPE: DNA
<213> ORGANISM: Artificial
<220> FEATURE:
<223> OTHER INFORMATION: Primer

<400> SEQUENCE: 189
dmbaawytcr ybartdagat cm                                           22

<210> SEQ ID NO 190
<211> LENGTH: 19
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..()
<223> OTHER INFORMATION: n is a or c or g or t

<400> SEQUENCE: 190
tgtgrcgatr natrsyttt                                               19

<210> SEQ ID NO 191
<211> LENGTH: 18
<212> TYPE: DNA
<213> ORGANISM: Artificial
<220> FEATURE:
<223> OTHER INFORMATION: Primer

<400> SEQUENCE: 191
yrchgatgaw gtgcaytc                                                18

<210> SEQ ID NO 192
<211> LENGTH: 19
<212> TYPE: DNA
<213> ORGANISM: Artificial
```

```
<220> FEATURE:
<223> OTHER INFORMATION: Primer

<400> SEQUENCE: 192
arttgthgta kgtytttcc                                                19

<210> SEQ ID NO 193
<211> LENGTH: 19
<212> TYPE: DNA
<213> ORGANISM: Artificial
<220> FEATURE:
<223> OTHER INFORMATION: Primer

<400> SEQUENCE: 193
kwkttcctgt tggggraar                                                19

<210> SEQ ID NO 194
<211> LENGTH: 20
<212> TYPE: DNA
<213> ORGANISM: Artificial
<220> FEATURE:
<223> OTHER INFORMATION: Primer

<400> SEQUENCE: 194
awygggtata kattscggta                                               20

<210> SEQ ID NO 195
<211> LENGTH: 26
<212> TYPE: DNA
<213> ORGANISM: Artificial
<220> FEATURE:
<223> OTHER INFORMATION: Primer

<400> SEQUENCE: 195
tttcctcgca tacactgccc gttgtt                                        26

<210> SEQ ID NO 196
<211> LENGTH: 18
<212> TYPE: DNA
<213> ORGANISM: Artificial
<220> FEATURE:
<223> OTHER INFORMATION: Primer

<400> SEQUENCE: 196
tattccgaca gaagccaa                                                 18

<210> SEQ ID NO 197
<211> LENGTH: 18
<212> TYPE: DNA
<213> ORGANISM: Artificial
<220> FEATURE:
<223> OTHER INFORMATION: Primer

<400> SEQUENCE: 197
tctttgtgaa ttccgcac                                                 18

<210> SEQ ID NO 198
<211> LENGTH: 18
<212> TYPE: DNA
<213> ORGANISM: Artificial
<220> FEATURE:
<223> OTHER INFORMATION: Primer

<400> SEQUENCE: 198
gttggggaaa aatggttc                                                 18
```

```
<210> SEQ ID NO 199
<211> LENGTH: 18
<212> TYPE: DNA
<213> ORGANISM: Artificial
<220> FEATURE:
<223> OTHER INFORMATION: Primer

<400> SEQUENCE: 199
ttttcttccg attcaccc                                                    18

<210> SEQ ID NO 200
<211> LENGTH: 18
<212> TYPE: DNA
<213> ORGANISM: Artificial
<220> FEATURE:
<223> OTHER INFORMATION: Primer

<400> SEQUENCE: 200
attgtggagc caattttg                                                    18

<210> SEQ ID NO 201
<211> LENGTH: 18
<212> TYPE: DNA
<213> ORGANISM: Artificial
<220> FEATURE:
<223> OTHER INFORMATION: Primer

<400> SEQUENCE: 201
tggatgtcat agctggga                                                    18

<210> SEQ ID NO 202
<211> LENGTH: 18
<212> TYPE: DNA
<213> ORGANISM: Artificial
<220> FEATURE:
<223> OTHER INFORMATION: Primer

<400> SEQUENCE: 202
tatccgctga ccttgttg                                                    18

<210> SEQ ID NO 203
<211> LENGTH: 18
<212> TYPE: DNA
<213> ORGANISM: Artificial
<220> FEATURE:
<223> OTHER INFORMATION: Primer

<400> SEQUENCE: 203
cgaatccacg atatcgaa                                                    18

<210> SEQ ID NO 204
<211> LENGTH: 18
<212> TYPE: DNA
<213> ORGANISM: Artificial
<220> FEATURE:
<223> OTHER INFORMATION: Primer

<400> SEQUENCE: 204
gtggatgggg tgaagact                                                    18

<210> SEQ ID NO 205
<211> LENGTH: 18
<212> TYPE: DNA
<213> ORGANISM: Artificial
<220> FEATURE:
<223> OTHER INFORMATION: Primer
```

<400> SEQUENCE: 205
tatggctctt ggggaact                                                              18

<210> SEQ ID NO 206
<211> LENGTH: 22
<212> TYPE: DNA
<213> ORGANISM: Artificial
<220> FEATURE:
<223> OTHER INFORMATION: Primer

<400> SEQUENCE: 206
gtatggattt cgtaccgtaa at                                                         22

<210> SEQ ID NO 207
<211> LENGTH: 20
<212> TYPE: DNA
<213> ORGANISM: Artificial
<220> FEATURE:
<223> OTHER INFORMATION: Primer

<400> SEQUENCE: 207
cctgcgacaa gacctctata                                                            20

<210> SEQ ID NO 208
<211> LENGTH: 21
<212> TYPE: DNA
<213> ORGANISM: Artificial
<220> FEATURE:
<223> OTHER INFORMATION: Primer

<400> SEQUENCE: 208
ctcaaccctt ctgagagttt t                                                          21

<210> SEQ ID NO 209
<211> LENGTH: 22
<212> TYPE: DNA
<213> ORGANISM: Artificial
<220> FEATURE:
<223> OTHER INFORMATION: Primer

<400> SEQUENCE: 209
cagcttggtc tacaactgtt ac                                                         22

<210> SEQ ID NO 210
<211> LENGTH: 28
<212> TYPE: DNA
<213> ORGANISM: Artificial
<220> FEATURE:
<223> OTHER INFORMATION: Primer

<400> SEQUENCE: 210
cagaggtagt tagaaaaatt attggact                                                   28

<210> SEQ ID NO 211
<211> LENGTH: 22
<212> TYPE: DNA
<213> ORGANISM: Artificial
<220> FEATURE:
<223> OTHER INFORMATION: Primer

<400> SEQUENCE: 211
ggcggaggat ggaatgaagg ca                                                         22

<210> SEQ ID NO 212

```
<211> LENGTH: 23
<212> TYPE: DNA
<213> ORGANISM: Artificial
<220> FEATURE:
<223> OTHER INFORMATION: Primer

<400> SEQUENCE: 212
cagtgggatt ctcttcatta tgc                                          23

<210> SEQ ID NO 213
<211> LENGTH: 22
<212> TYPE: DNA
<213> ORGANISM: Artificial
<220> FEATURE:
<223> OTHER INFORMATION: Primer

<400> SEQUENCE: 213
agccttttga tctgtggcga ta                                           22

<210> SEQ ID NO 214
<211> LENGTH: 22
<212> TYPE: DNA
<213> ORGANISM: Artificial
<220> FEATURE:
<223> OTHER INFORMATION: Primer

<400> SEQUENCE: 214
gtggctcatc acattgatca ca                                           22

<210> SEQ ID NO 215
<211> LENGTH: 22
<212> TYPE: DNA
<213> ORGANISM: Artificial
<220> FEATURE:
<223> OTHER INFORMATION: Primer

<400> SEQUENCE: 215
tgggcaatgt tggctttaat tt                                           22

<210> SEQ ID NO 216
<211> LENGTH: 30
<212> TYPE: DNA
<213> ORGANISM: Artificial
<220> FEATURE:
<223> OTHER INFORMATION: Primer

<400> SEQUENCE: 216
gcctagacat ccatgtttgt ttccatatca                                   30

<210> SEQ ID NO 217
<211> LENGTH: 15
<212> TYPE: PRT
<213> ORGANISM: Artificial
<220> FEATURE:
<223> OTHER INFORMATION: Consensus stucture
<220> FEATURE:
<221> NAME/KEY: SITE
<222> LOCATION: (1)..(1)
<223> OTHER INFORMATION: Xaa is Lys/Arg
<220> FEATURE:
<221> NAME/KEY: SITE
<222> LOCATION: (2)..(2)
<223> OTHER INFORMATION: Xaa is Gly/Ala
<220> FEATURE:
<221> NAME/KEY: SITE
<222> LOCATION: (3)..(4)
<223> OTHER INFORMATION: Xaa is uncertain
<220> FEATURE:
<221> NAME/KEY: SITE
```

```
<222> LOCATION: (5)..(5)
<223> OTHER INFORMATION: Xaa is Phe/Tyr/Trp
<220> FEATURE:
<221> NAME/KEY: SITE
<222> LOCATION: (6)..(6)
<223> OTHER INFORMATION: Xaa is Leu/Ile/Val
<220> FEATURE:
<221> NAME/KEY: VARIANT
<222> LOCATION: (3)..(4)
<220> FEATURE:
<221> NAME/KEY: VARIANT
<222> LOCATION: (11)..(12)

<400> SEQUENCE: 217

Xaa Xaa Xaa Xaa Xaa Xaa Xaa Xaa Xaa Gln Xaa Xaa Gly Xaa Trp
1               5                   10                  15

<210> SEQ ID NO 218
<211> LENGTH: 5
<212> TYPE: PRT
<213> ORGANISM: Artificial
<220> FEATURE:
<223> OTHER INFORMATION: Consensus sequence

<400> SEQUENCE: 218

Asp Cys Thr Ala Glu
1               5

<210> SEQ ID NO 219
<211> LENGTH: 43
<212> TYPE: DNA
<213> ORGANISM: Artificial
<220> FEATURE:
<223> OTHER INFORMATION: Primer

<400> SEQUENCE: 219
gcgagtaagg atcctcacgc aaggaattcc gaccagacag gcc                    43
```

ISOLATED PLANT GENE ENCODING A β AMYRIN SYNTHASE

This application is a 35 U.S.C. §371 application which claims priority to PCT/GB00/04908 filed Dec. 20, 2000, the disclosure of which is incorporated herein by reference.

The present invention relates to methods and materials, particularly nucleic acids, for manipulating the levels of terpenoids in plants. It further relates to plants which have been modified using such methods and materials.

PRIOR ART

Triterpenoids are of relevance to a variety of plant characteristics, including palatability to animals, and resistance to pathogens and predators. Triterpenes are mostly stored in plant roots as their glycosides, saponins (see Price et al, 1987 CRC Crit Rev Food Sci Nutr 26, 27–133). Thus, for example, mutants of the diploid oat species, *Avena strigosa* which lack the major oat root saponin, avenacin A-1 (so called saponin-deficient or 'sad' mutants) have been shown to have compromised disease resistance (Papadopoulou et al, 1999 Proc Natl Acad Sci 96, 12923–12928). These mutants have increased susceptibility to a number of different root-infecting fungi, including *Gaeumannomyces graminis* var. *tritici*, which is normally non-pathogenic to oats. Genetic analysis suggests that increased disease susceptibility and reduced avenacin content are causally related. Furthermore, a sad mutant which produces reduced avenacin levels (around 15% of that of the wild type) gives only limited disease symptoms when inoculated with *G. graminis* var. *tritici* in comparison to other mutants which lack avenacins completely, providing a further link between avenacin content and disease resistance.

β-amyrin is the most popular type of triterpene found in higher plants. Two of the *Avena strigosa* mutants, designated 610 and 109, represent different mutant alleles at the Sad1 locus.

These mutants both lack detectable levels of 2,3-oxidosqualene β-amyrin cyclase (termed hereinafter β-amyrin synthase) which is an oxidosqualene cyclase and is the first committed enzyme in the triterpenoid pathway (see Advances in Lipid Research, 458–461, J. Sanchez, E Cerda-Oledo and E Martinez-Force (eds), 1998). Root preparations of these two mutants also accumulate $^{14}$C-2,3-oxidosqualene and do not produce detectable levels of $^{14}$C-β-amyrin when fed with the radioactive precursor R-[2-$^{14}$C] mevalonic acid, again indicating that the step involving the cyclization of 2,3-oxidosqualene to β-amyrin is blocked. It therefore appears that β-amyrin synthase can play a significant role in modifying traits such as disease resistance in plants.

β-amyrin synthase has been cloned from the hairy root of *Panax ginseng* by Kushiro et al (1998) Eur J Biochem 256: 238–244. These workers used degenerate oligonucleotide primers based on known oxidosqualene synthases. The plant was selected because it is a source of crude drug preparations.

A soybean EST (GenBank Accession AI900929) has also been identified which shares homology with the *ginseng* sequence.

DISCLOSURE OF THE INVENTION

The present inventors have succeeded in isolating and characterising a cDNA encoding an oxidosqualene cyclase from oat (*A. strigosa*). This has the characteristics of β-amyrin synthase and has been designated as such herein. An initial attempt to clone the oat gene using primers based on the *ginseng* sequence was not successful, yielding instead the gene encoding the highly homologous, but functionally distinct, cycloartenol synthase. The cloning of β-amyrin synthase was eventually achieved using a more complicated subtractive cDNA library approach, based on the differential expression of the gene in different parts of the root.

Thus in a first aspect of the present invention there is disclosed a nucleic acid molecule encoding oxidosqualene cyclase from oat which has the characteristics of β-amyrin synthase.

Nucleic acid molecules according to the present invention may be provided isolated and/or purified from their natural environment, in substantially pure or homogeneous form, or free or substantially free of other nucleic acids of the species of origin. Where used herein, the term "isolated" encompasses all of these possibilities.

The nucleic acid molecules may be wholly or partially synthetic. In particular they may be recombinant in that nucleic acid sequences which are not found together in nature (do not run contiguously) have been ligated or otherwise combined artificially. Alternatively they may have been synthesised directly e.g. using an automated synthesiser. They may consist essentially of the gene in question.

Nucleic acid according to the present invention may include cDNA, RNA, genomic DNA and modified nucleic acids or nucleic acid analogs. Where a DNA sequence is specified, e.g. with reference to a figure, unless context requires otherwise the RNA equivalent, with U substituted for T where it occurs, is encompassed. Where a nucleic acid of the invention is referred to herein, the complement of that nucleic acid will also be embraced by the invention. Where genomic nucleic acid sequences of the invention are disclosed, nucleic acids comprising any one or more introns or exons from any of those sequences are also embraced.

Where a nucleic acid (or nucleotide sequence) of the invention is referred to herein, the complement of that nucleic acid (or nucleotide sequence) will also be embraced by the invention. The 'complement' in each case is the same length as the reference, but is 100% complementary thereto whereby by each nucleotide is capable of base pairing with its counterpart i.e. G to C, and A to T or U.

The 'characteristics of β-amyrin synthase' means that the encoded polypeptide has β-amyrin synthase activity i.e. the ability to catalyse the conversion of 2,3-oxidosqualene into β-amyrin (see discussion in Kushiro et al, 1998, supra, particularly FIG. 1 therein). β-amyrin synthase function may be assessed as set out in the Examples below e.g. using expression in yeast followed by TLC of biosynthetic products, or by complementation in sad mutants.

Nucleic acids of the first aspect may be advantageously utilised in plants to improve resistance against pathogens. For instance, referring to Papadopoulou et al (1999) supra, enzymes which modify levels of saponins such as β-amyrin appear to play a role in resistance against fungi, typically those ascomycetes which have sterol molecules in their membranes.

Target pathogens for such resistance will not be oomycetes, but may include *Gaeumannomyces graminis* vars *tritici* and *avenae; Fusarium culmorum; Fusarium avanaceum; Stagonospora nodorum; Stagonospora avenae*. Other Examples may be those which are set out in "The plant Pathologists Pocket Book" 2$^{nd}$ Ed. compiled by Commonwealth Mycological Institute, Kew, Surrey and published by Commonwealth Agricultural Bureaux, England ISBN 0851985173, particularly on pages 102–103 (affecting barley, broad bean, sugar beet, Brassicas); pages 110–113 (affecting lettuce, maize and oat); pages 116–121 (affecting potato, rice, rye, sorghum, soybean, spruce, strawberry, sugarcane; sunflower; tomato; wheat).

Plants over expressing the enzyme may also be useful sources of oleanane type triterpene saponins for the chemical or pharmaceutical industries e.g. for use in the preparation of antimicrobial phytoprotectants, or drugs. Plants having modified levels of saponins will may also have a modified taste and/or nutritional value.

Plants in which it may be desirable in principle be desirable to express, or over express, nucleic acids of the present invention may include any of those discussed above. Particularly preferred may be barley, bean (phaseolus), pea, sugar beet, maize; oat; solanum (e.g. potato); allium (e.g. garlic, onion and leek); asparagus; tea; peanut; spinach; cucurbitaceae; yam; rice; rye; sorghum; soyabean; spruce; strawberry; sugarcane; sunflower; tomato; wheat (see also Price et al, supra).

Most preferably the invention is employed using rice, wheat, maize or barley.

Thus in one embodiment of this aspect of the invention, there is disclosed a nucleic acid comprising the OAT β-amyrin synthase nucleotide sequence shown in Annex (I) or a sequence being degeneratively equivalent thereto.

This embodiment embraces any isolated nucleic acid encoding the OAT β-amyrin synthase amino acid sequence shown in Annex (II). Clearly such a nucleic acid may comprise the encoding sequence in Annex (I), or Annex (VIII).

In a further aspect of the present invention there are disclosed nucleic acids which are variants of the sequences of the first aspect.

A variant nucleic acid molecule shares homology with, or is identical to, all or part of the coding sequence discussed above. Generally, variants may encode, or be used to isolate or amplify nucleic acids which encode, polypeptides which are capable of modifying terpenoid, (particularly triterpenoid, more particularly saponin) synthesis in a plant, and hence alter the pathogen resistance of that plant, and/or which will specifically bind to an antibody raised against the polypeptide of Annex (II). The triterpenoid synthetic function, particularly β-amyrin synthase,function, may be assessed as set out in the Examples below.

Variants of the present invention can be artificial nucleic acids (i.e. containing sequences which have not originated naturally) which can be prepared by the skilled person in the light of the present disclosure. Alternatively they may be novel, naturally occurring, nucleic acids, which may be isolatable using the sequences of the present invention.

Thus a variant may be a distinctive part or fragment (however produced) corresponding to a portion of the sequence provided. The fragments may encode particular functional parts of the polypeptide.

Equally the fragments may have utility in probing for, or amplifying, the sequence provided or closely related ones. Suitable lengths of fragment, and conditions, for such processes are discussed in more detail below.

Also included are nucleic acids which have been extended at the 3' or 5' terminus.

Sequence variants which occur naturally may include alleles or other homologues (which may include polymorphisms or mutations at one or more bases).

Artificial variants (derivatives) may be prepared by those skilled in the art, for instance by site directed or random mutagenesis, or by direct synthesis. Preferably the variant nucleic acid is generated either directly or indirectly (e.g. via one or amplification or replication steps) from an original nucleic acid having all or part of the sequences of the first aspect. Preferably it encodes a β-amyrin synthase.

The term 'variant' nucleic acid as used herein encompasses all of these possibilities. When used in the context of polypeptides or proteins it indicates the encoded expression product of the variant nucleic acid.

Some of the aspects of the present invention relating to variants will now be discussed in more detail.

Homology (i.e. similarity or identity) may be as defined using sequence comparisons are made using FASTA and FASTP (see Pearson & Lipman, 1988. Methods in Enzymology 183: 63–98). Parameters are preferably set, using the default matrix, as follows:

Gapopen (penalty for the first residue in a gap): −12 for proteins/−16 for DNA

Gapext (penalty for additional residues in a gap): −2 for proteins/−4 for DNA

KTUP word length: 2 for proteins/6 for DNA.

Homology may be at the nucleotide sequence and/or encoded amino acid sequence level. Preferably, the nucleic acid and/or amino acid sequence shares at least about 60%, or 70%, or 80% homology, most preferably at least about 90%, 95%, 96%, 97%, 98% or 99% homology with oat β-amyrin synthase.

Thus a variant polypeptide in accordance with the present invention may include within the sequence shown in Annex V, a single amino acid or 2, 3, 4, 5, 6, 7, 8, or 9 changes, about 10, 15, 20, 30, 40 or 50 changes, or greater than about 50, 60, 70, 80, 90, 100, 200, 300 changes. In addition to one or more changes within the amino acid sequence shown, a variant polypeptide may include additional amino acids at the C-terminus and/or N-terminus.

Naturally, regarding nucleic acid variants, changes to the nucleic acid which make no difference to the encoded polypeptide (i.e. 'degeneratively equivalent') are included within the scope of the present invention.

Thus in a further aspect of the invention there is disclosed a method of producing a derivative nucleic acid comprising the step of modifying the coding sequence of a nucleic acid of Annex I.

Changes to a sequence, to produce a derivative, may be by one or more of addition, insertion, deletion or substitution of one or more nucleotides in the nucleic acid, leading to the addition, insertion, deletion or substitution of one or more amino acids in the encoded polypeptide.

Changes may be desirable for a number of reasons, including introducing or removing the following features: restriction endonuclease sequences; codon usage; other sites which are required for post translation modification; cleavage sites in the encoded polypeptide; motifs in the encoded polypeptide (e.g. binding sites). Leader or other targeting sequences (e.g. hydrophobic anchoring regions) may be added or removed from the expressed protein to determine its location following expression. All of these may assist in efficiently cloning and expressing an active polypeptide in recombinant form (as described below).

Other desirable mutation may be random or site directed mutagenesis in order to alter the activity (e.g. specificity) or stability of the encoded polypeptide.

Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Also included are variants having non-conservative substitutions. As is well known to those skilled in the art, substitutions to regions of a peptide which are not critical in determining its conformation may not greatly affect its activity because they do not greatly alter the peptide's three dimensional structure.

In regions which are critical in determining the peptides conformation or activity such changes may confer advantageous properties on the polypeptide. Indeed, changes such as those described above may confer slightly advantageous properties on the peptide e.g. altered stability or specificity.

In a further aspect of the present invention there is provided a method of identifying and/or cloning a nucleic acid variant from a plant which method employs a probe or primer of the present invention. Target plants include (but are not limited to) rice, maize, wheat, barley, alfalfa, chickpea, bean and pea.

An oligonucleotide for use in probing or amplification reactions comprise or consist of about 48, 36 or fewer nucleotides in length (e.g. 18, 21 or 24). Generally specific primers are upwards of 14 nucleotides in length. For optimum specificity and cost effectiveness, primers of 16–30 nucleotides in length may be preferred. Those skilled in the art are well versed in the design of primers for use processes such as PCR. If required, probing can be done with entire restriction fragments of the gene disclosed herein which may be 100's or even 2000 or more nucleotides in length.

Generally speaking, two classes of probe/primer form a part of the present invention.

For instance, one class of primer, typified by those shown in Table 1, is distinctive in the sense that it is based on any region present in the β-amyrin synthase sequence disclosed herein, but not in any region of the non-closely related sequences of the prior art (e.g. the soyabean or *ginseng* sequences discussed supra). 'Based on' in this sense can mean that the primer is found in or degeneratively equivalent to the β-amyrin synthase region, or its complement. Examples are shown in Table 1. Such primers will have utility not only in manipulating the oat β-amyrin synthase sequence, but also in those which are expected to be more closely related to it e.g. other monocot β-amyrin synthase genes, such as those from rice, maize, wheat, barley etc.

A second class of primer, typified by those shown in Table 2, is generic in the sense that it is based on regions of β-amyrin synthase genes (or related genes) which appear to be conserved between e.g. the soyabean/*ginseng* sequences and the oat sequence. Such primers, devised on the basis of the oat β-amyrin synthase gene, will have utility in manipulating amyrin synthase and related sequences in general. Such primers also include any which are based on the conserved DCTAE motif present in the predicted amino acid sequences of several triterpene biosynthetic enzymes from different species (see Annex VI).

A further class of primers is shown in Table 3, which were used in the Examples hereinafter to amplify regions of the genomic sequence of oat β-amyrin synthase gene. Other primers, shown in the Examples below, and used to identify the genomic sequence, were based on cDNA sequence (AMYstaF5 based on the initiation codon, and AMYendR5 based on the 3' UTR region).

Some other primers of the invention are designated ASEQ1-4 in the Examples below.

In one embodiment, nucleotide sequence information provided herein may be used in a data-base (e.g. of expressed sequence tags, or sequence tagged sites) search to find homologous sequences, such as those which may become available in due course, and expression products of which can be tested for activity as described below.

In a further embodiment, a variant in accordance with the present invention is also obtainable by means of a method which includes:
(a) providing a preparation of nucleic acid, e.g. from plant cells,
(b) providing a nucleic acid molecule which is a probe as described above,
(c) contacting nucleic acid in said preparation with said nucleic acid molecule under conditions for hybridisation of said nucleic acid molecule to any said gene or homologue in said preparation, and identifying said gene or homologue if present by its hybridisation with said nucleic acid molecule.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.), such as is described hereinafter. Probing may optionally be done by means of so-called 'nucleic acid chips' (see Marshall & Hodgson (1998) Nature Biotechnology 16: 27–31, for a review).

Preliminary experiments may be performed by hybridising under low stringency conditions. For probing, preferred conditions are those which are stringent enough for there to be a simple pattern with a small number of hybridisations identified as positive which can be investigated further.

For instance, screening may initially be carried out under conditions, which comprise a temperature of about 37° C. or less, a formamide concentration of less than about 50%, and a moderate to low salt (e.g. Standard Saline Citrate ('SSC')=0.15 M sodium chloride; 0.15 M sodium citrate; pH 7) concentration.

Alternatively, a temperature of about 50° C. or less and a high salt (e.g. 'SSPE'=0.180 mM sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid.

Suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M Na$_2$HPO$_4$, pH 7.2, 6.5% SDS, 10% dextran sulfate and a final wash at 60° C. in 0.1×SSC, 0.1% SDS.

It is well known in the art to increase stringency of hybridisation gradually until only a few positive clones remain. Suitable conditions would be achieved when a large number of hybridising fragments were obtained while the background hybridisation was low. Using these conditions nucleic acid libraries, e.g. cDNA libraries representative of expressed sequences, may be searched. Those skilled in the art are well able to employ suitable conditions of the desired stringency for selective hybridisation, taking into account factors such as oligonucleotide length and base composition, temperature and so on.

One common formula for calculating the stringency conditions required to achieve hybridization between nucleic acid molecules of a specified sequence homology is (Sambrook et al., 1989):

$$T_m = 81.5° C. + 16.6 \log [Na+] + 0.41(\% G+C) - 0.63(\% \text{formamide}) - 600/\#bp \text{ in duplex}$$

As an illustration of the above formula, using [Na+]=[0.368] and 50–% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (see below) or RN'ase cleavage. The identification of successful hybridisation is followed by isolation of the nucleic acid which has hybridised, which may involve one or more steps of PCR or amplification of a vector in a suitable host.

Thus one embodiment of this aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a product able to influence a resistance characteristic of a plant, particularly via modification of triterpenoid synthesis.

In a further embodiment, hybridisation of nucleic acid molecule to a variant may be determined or identified indirectly, e.g. using a nucleic acid amplification reaction, particularly the polymerase chain reaction (PCR). PCR requires the use of two primers to amplify target nucleic acid, so preferably two primers as described above are employed. Using RACE PCR, one 'random' may be used (see "PCR protocols; A Guide to Methods and Applications", Eds. Innis et al, Academic Press, New York, (1990)).

Thus a method involving use of PCR in obtaining nucleic acid according to the present invention may be carried out as described above, but using a pair of nucleic acid molecule primers useful in (i.e. suitable for) PCR, at least one of which is a primer of the present invention as described above.

In each case above, if need be, clones or fragments identified in the search can be extended. For instance if it is suspected that they are incomplete, the original DNA source (e.g. a clone library, mRNA preparation etc.) can be revisited to isolate missing portions e.g. using sequences, probes or primers based on that portion which has already been obtained to identify other clones containing overlapping sequence.

The methods described above may also be used to determine the presence of one of the nucleotide sequences of the present invention within the genetic context of an individual plant, optionally a transgenic plant, which may be produced as described in more detail below. This may be useful in plant breeding programmes e.g. to directly select plants containing alleles which are responsible for desirable traits in that plant species, either in parent plants or in progeny (e.g. hybrids, F1, F2 etc.). Thus use of particular novel markers defined in the Examples below, or markers which can be designed by those skilled in the art on the basis the nucleotide sequence information disclosed herein, forms one part of the present invention.

As used hereinafter, unless the context demands otherwise, the term "β-amyrin synthase nucleic acid" is intended to cover any of the nucleic acids of the invention described above, including functional variants.

In one aspect of the present invention, the β-amyrin synthase nucleic acid described above is in the form of a recombinant and preferably replicable vector.

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eucaryotic (e.g. higher plant, mammalian, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

Thus this aspect of the invention provides a gene construct, preferably a replicable vector, comprising a promoter operatively linked to a nucleotide sequence provided by the present invention, such as β-amyrin synthase or a variant thereof.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press (or later editions of this work).

Many known techniques and protocols for manipulation of nucleic acid, for example in preparation of nucleic acid constructs, mutagenesis (see above discussion in respect of variants), sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

In one embodiment of this aspect of the present invention, there is provided a gene construct, preferably a replicable vector, comprising an inducible promoter operatively linked to a nucleotide sequence provided by the present invention.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Particular of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121–148).

Suitable promoters which operate in plants include the Cauliflower Mosaic Virus 35S (CaMV 35S). Other examples are disclosed at pg 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177–180. It may be desirable to use a strong constitutive promoter such as the ubiquitin promoter, particularly in monocots.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising introduction of such a construct into a host cell, particularly a plant cell.

In a further aspect of the invention, there is disclosed a host cell containing a heterologous construct according to the present invention, especially a plant or a microbial cell.

The term "heterologous" is used broadly in this aspect to indicate that the gene/sequence of nucleotides in question (a β-amyrin synthase gene) have been introduced into said cells of the plant or an ancestor thereof, using genetic engineering, i.e. by human intervention. A heterologous gene may replace an endogenous equivalent gene, i.e. one which normally performs the same or a similar function, or the inserted sequence may be additional to the endogenous gene or other sequence.

Nucleic acid heterologous to a plant cell may be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homolog is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

The host cell (e.g. plant cell) is preferably transformed by the construct, which is to say that the construct becomes established within the cell, altering one or more of the cell's characteristics and hence phenotype e.g. with respect to triterpenoid synthesis and/or fungal pathogen resistance.

Nucleic acid can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture,* Academic Press), electroporation (EP 290395, WO 8706614 Gelvin Debeyser) other forms of direct DNA uptake (DE 4005152, WO 9012096, U.S. Pat. No. 4,684, 611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1–11.

Agrobacterium transformation is widely used by those skilled in the art to transform dicotyledonous species. Recently, there has also been substantial progress towards the routine production of stable, fertile transgenic plants in almost all economically relevant monocot plants (see e.g. Hiei et al. (1994) *The Plant Journal* 6, 271–282)). Microprojectile bombardment, electroporation and direct DNA uptake are preferred where Agrobacterium alone is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

It will be apparent to the skilled person that the particular choice of a transformation system to introduce nucleic acid into plant cells is not essential to or a limitation of the invention, nor is the choice of technique for plant regeneration.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention (e.g. comprising oat β-amyrin synthase sequence) especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Generally speaking, following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Plants which include a plant cell according to the invention are also provided.

In addition to the regenerated plant, the present invention embraces all of the following: a clone of such a plant, selfed or hybrid progeny and descendants (e.g. F1 and F2 descendants) and any part of any of these. The invention also provides parts of such plants e.g. any part which may be used in reproduction or propagation, sexual or asexual, including cuttings, seed and so on, or which may be a commodity per se e.g. grain.

A plant according to the present invention may be one which does not breed true in one or more properties. Plant varieties may be excluded, particularly registrable plant varieties according to Plant Breeders' Rights.

The invention further provides a method of influencing or affecting the nature or degree of the triterpenoid (e.g. β-amyrin) synthesis in a plant, and thereby optionally its resistance to a fungal pathogen, the method including the step of causing or allowing expression of a heterologous nucleic acid sequence as discussed above within the cells of the plant. This aspect preferably involves use of the sequence of Annex I (or the polypeptide of Annex II).

Analogous methods for altering taste, palatability etc. of a plant are also embraced.

The step may be preceded by the earlier step of introduction of the nucleic acid into a cell of the plant or an ancestor thereof.

The foregoing discussion has been generally concerned with uses of the nucleic acids of the present invention for production of functional β-amyrin synthase polypeptides in a plant, thereby increasing its pathogen resistance. However the information disclosed herein may also be used to reduce the activity or levels of such polypeptides in cells in which it is desired to do so. Reduction in triterpenoid synthesis and downstream secondary metabolites. Triterpenoids exhibit a wide variety of functions in biological systems and in principle their down-regulation may be desirable to modify these functions. For instance the palatability of a plants may be improved by reducing levels of these compounds.

The sequence information disclosed herein may be used for the down-regulation of expression of genes e.g. using anti-sense technology (see e.g. Bourque, (1995), *Plant Science* 105, 125–149); sense regulation [co-suppression] (see e.g. Zhang et al., (1992) *The Plant Cell* 4, 1575–1588). Further options for down regulation of gene expression include the use of ribozymes, e.g. hammerhead ribozymes, which can catalyse the site-specific cleavage of RNA, such as mRNA (see e.g. Jaeger (1997) "The new world of ribozymes" *Curr Opin Struct Biol* 7:324–335.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Flavell, (1994) *PNAS USA* 91, 3490–3496.

An alternative to anti-sense is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 279–289 and U.S. Pat. No. 5,231,020. Further refinements of the gene silencing or co-suppression technology may be found in WO 95/34668 (Biosource); Angell & Baulcombe (1997) *The EMBO Journal* 16,12:3675–3684; and Voinnet & Baulcombe (1997) *Nature* 389: pg 553.

Nucleic acids and associated methodologies for carrying out down-regulation (e.g. complementary sequences) form one part of the present invention.

The present invention also encompasses the expression product of any of the β-amyrin synthase (particularly functional β-amyrin synthase) nucleic acid sequences disclosed above, plus also methods of making the expression product by expression from encoding nucleic acid therefore under suitable conditions, which may be in suitable host cells.

A preferred polypeptide includes the amino acid sequence shown in Annex II. However a polypeptide according to the present invention may be a variant (allele, fragment, derivative, mutant or homologue etc.) of the polypeptide as shown in Annex II. The allele, variant, fragment, derivative, mutant or homologue may have substantially the β-amyrin synthase function of the amino acid sequence shown in Annex II.

Also encompassed by the present invention are polypeptides which although clearly related to a functional oat β-amyrin synthase polypeptide (e.g. they are immunologically cross reactive with the oat β-amyrin synthase polypeptide, or they have characteristic sequence motifs in common with the β-amyrin synthase polypeptide) no longer have β-amyrin synthase function.

Following expression, the recombinant product may, if required, be isolated from the expression system. Generally however the polypeptides of the present invention will be used in vivo (in particular in planta).

Purified oat β-amyrin synthase or variant protein, produced recombinantly by expression from encoding nucleic acid therefor, may be used to raise antibodies employing techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal. As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO 92/01047.

Antibodies raised to a polypeptide or peptide can be used in the identification and/or isolation of homologous polypeptides, and then the encoding genes. Thus, the present invention provides a method of identifying or isolating a polypeptide with β-amyrin synthase function (in accordance with embodiments disclosed herein), including screening candidate peptides or polypeptides with a polypeptide including the antigen-binding domain of an antibody (for example whole antibody or a fragment thereof) which is able to bind an oat β-amyrin synthase peptide, polypeptide or fragment, variant or variant thereof or preferably has binding specificity for such a peptide or polypeptide, such as having an amino acid sequence identified herein. Specific binding members such as antibodies and polypeptides including antigen binding domains of antibodies that bind and are preferably specific for a β-amyrin synthase peptide or polypeptide or mutant, variant or derivative thereof represent further aspects of the present invention, as do their use and methods which employ them.

Candidate peptides or polypeptides for screening may for instance be the products of an expression library created using nucleic acid derived from an plant of interest, or may be the product of a purification process from a natural source.

In addition to the coding parts of the oat β-amyrin synthase gene, and the expression products, also embraced within the present invention are untranscribed parts of the gene.

Thus a further aspect of the invention is an isolated nucleic acid molecule encoding the promoter of the oat β-amyrin synthase gene. This is shown in the sequence Annexes hereinafter.

Also included are homologous variants, or portions, of the promoter, which have "promoter activity" i.e. the ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene facilitates determination of promoter activity by reference to protein production. The reporter gene preferably encodes an enzyme which catalyses a reaction which produces a detectable signal, preferably a visually detectable signal, such as a coloured product. Many examples are known, including β-galactosidase and luciferase. The presence and/or amount of gene product resulting from expression from the reporter gene may be determined using a molecule able to bind the product, such as an antibody or fragment thereof. The binding molecule may be labelled directly or indirectly using any standard technique. Those skilled in the art are well aware of a multitude of possible reporter genes and assay techniques which may be used to determine promoter activity. Any suitable reporter/assay may be used and it should be appreciated that no particular choice is essential to or a limitation of the present invention.

Homologous variants can be prepared or identified in similar manner to those described above in relation to the coding sequence. To find minimal elements or motifs responsible for activity or regulation, restriction enzyme or nucleases may be used to digest a nucleic acid molecule, or mutagenesis may be employed, followed by an appropriate assay (for example using a reporter gene such as luciferase) to determine the sequence required. Nucleic acid comprising these elements or motifs forms one part of the present invention.

Certain regions of the promoter which are believed to bind transcription factors (based on computational analysis) are identified in the sequence Annexes below. Such fragments including one or more of these regions, and having promoter activity, may be particularly preferred.

In a further aspect of the invention there is provided a nucleic acid construct, preferably an expression vector, including the oat β-amyrin synthase gene promoter region or fragment, mutant, derivative or other homologue or variant thereof able to promote transcription, operably linked to a heterologous gene, e.g. a coding sequence, which is preferably not the coding sequence with which the promoter is operably linked in nature.

The invention will now be further described with reference to the following non-limiting Examples and Annexes. Other embodiments of the invention will occur to those skilled in the art in the light of these.

Annexes
(I)—OAT β-amyrin synthase cDNA (nucleotide sequence)
(II)—OAT β-amyrin synthase cDNA (amino acid sequence)
(III)—ort1s.pk001.c14 (putative oxidosqualene cyclase EST clone from *Avena strigosa*)
(IV)—CLUSTAL W (1.8) multiple sequence alignment of 6 clones encoding the 5' end of an oxidosqualene cyclase from *A. strigosa*
(V)—CLUSTAL W (1.8) multiple sequence alignment of 6 clones encoding the 3' end of an oxidosqualene cyclase from *A. strigosa*
(VI)—Alignment of the DCTAE motif in the predicted amino acid sequences of triterpene biosynthetic enzymes of different species
(VII)—Alignment of the β-amyrin synthase with cycloarternol synthase of *A. strigosa*
(VIII)—The complete genomic sequence (from the translational start codon (ATG) to the stop codon (TGA)) of the β-amyrin synthase from *Avena strigosa*. Uppercase letters represent the exons and lowercase letters represent the introns. The splice-junction sites were predicted according to the cDNA sequence and by using the "BCM gene finder" web page at the Baylor College of Medicine and the "Splice Site Prediction by Neural Network" web page at the University of California. The gene consists of 18 exons and 17 introns.

(IX)—The complete sequence of the 1941 bp of the β-amyrin synthase promoter. The initiation of translation start codon is given in uppercase letters. The initiation of transcription start site is underlined and was predicted using the "Promoter Prediction by Neural Network" web page at the University of California. The underlined tatataa sequence represents the putative TATA signal predicted with the HCtata (Hamming-Clustering Method for TATA Signal Prediction in Eukaryotic Genes) interactive program at the "WEBGENE" web page of the Institute of Advanced Biomedical Technologies (ITBA).

(X)—Computational analysis of the promoter region using the MatInspector program at the Genomatix web page in Germany. This revealed several putative transcription factor binding sites. Parameters used for the search were: Plant databank-section, Core similarity 0.75 and Matrix similarity 0.85. Above and below the putative binding site position is given the name, the sense (+) or antisense (−) direction, the consensus sequence and the matrix similarity of the corresponding transcription factor.

Tables

Table 1—Specific primers for amplifying *A. strigosa* β-amyrin synthase

Table 2—Primers for amplifying β-amyrin synthases

Table 3—Primers for amplifying β-amyrin synthases genomic sequence.

The nucleotide codes are as follows:

M=A OR C
R=A OR G
W=A OR T
S=C OR G
Y=C OR T
K=G OR T
V=A OR C OR G
H=A OR C OR T
D=A OR G OR T
B=C OR G OR T
N=A OR C OR G OR T

Blast Searches

BLAST Analysis using partial cDNA sequence (clone ort1s.pk001.c14)

Further Blastx searches using β-amyrin synthase sequence.

EXAMPLES

Example 1

Construction of Oat Root cDNA Libraries

Two cDNA libraries were constructed and sequenced using standard techniques. These cDNA libraries were all derived from *A. strigosa* accession number S75 (from the Institute of Grasslands and Environmental Research, Aberystwyth, Wales, UK). The libraries were as follows:

1. ort1s: A subtractive library derived from RNA from wild type (WT) oat root tip material(terminal 5 mm) subtracted against RNA from the remainder of the root.

2. ort1f: A full length cDNA library derived from RNA from root tips of the WT oat line (unsubtracted).

ort1s: WT (S75) root tip vs. remainder of the root subtractive cDNA library

*A. strigosa* (WT) seeds were surface sterilized with 5% sodium hypochlorite and washed several times with sterile deionized water. After a cold treatment for 48 h at 4° C., the seeds were placed on plates containing wet filter paper and allowed to germinate at 24° C. in the dark. Root tips (the terminal 5 mm) and the remainder of the root were collected from three-day old seedlings. Total RNA was extracted from both tissues using the RNeasy Plant Mini Kit from Qiagen. For the mRNA isolation we used the Dynabeads mRNA Purification Kit from Dynal. Synthesis of complementary DNA from both mRNA populations and library construction was performed with the SMART PCR cDNA Synthesis Kit and the PCR-Select cDNA Subtraction Kit from Clontech, according to the manufacture instruction. The root-tip-derived cDNA was used as "tester" and the rest-root-derived cDNA as "driver". The amplified cDNA fragments were purified and tailed (200 mM dATP) with Taq DNA polymerase for 30 min at 70° C. Four identical ligation reaction were performed using 1 ml (60 ng) of the tailed cDNA and 0.5 ml (25 ng) pGEM-T vector (Promega) for 16 h at 4° C. with 3 units of ligase (Promega). The reactions were pooled and the mix was purified using the PCR Purification Kit from Qiagen. 1 ml (2 ng) of the purified ligation mix was used to transform 10 ml of ELECTROMAX DH10B competent cells (Gibco BRL) by electroporation (Calvin NM, et al. J Bacteriol. 170(6), 2796–2801, 1988).

ort1f: WT (S75) root-tip specific 1-ZAP cDNA library.

Harvest of root-tip material, total RNA extraction and mRNA isolation was performed as previously described for the construction of the ort1s library. Complementary DNA was synthesized with the ZAP-cDNA Synthesis Kit from Stratagene and the library was cloned into the ZAP Express Vector according to the manufacturer's instructions. Plasmid clones were generated from each positive phage plaque by in vivo excision, using ExAssist helper phage and *E. coli* strain SOLR, according to the ZAP-cDNA Gigapack III Gold Cloning Kit manual (Stratagene).

Example 2

Isolation of a Partial cDNA Predicted to Encode β-amyrin Synthase from *Avena strigosa* Using a cDNA Probe Predicted to Encode an Oxidosqualene Cyclase Identified by DNA Sequence Analysis of the Ort1s cDNA Library DNA sequence analysis of the ort1s cDNA library identified a partial cDNA sequence (clone ort1s.pk001.c14) with homology to oxidosqualene cyclases (see Annex III).

This clone was used as a probe to screen the oat root full length cDNA library ort1f. Approximately 450,000 phage plaques were plated on 6 NZY plates (5 g/lt NaCl, 2 g/lt MgSO$_4$.7H$_2$O, 5 g/lt yeast extract, 10 g/lt casein hydrolysate and 15g/lt agar, pH7.5) according to standard procedures (Sambrook J et al. Molecular Cloning: A Laboratory Manual. Cold Spring Harbor Laboratory Press, Cold Spring Harbor, 1989) and plaque lifting was performed on Hybond-N+ membranes (Amersham) following the manufacturer's instructions. The ort1s.pk001.c14 clone was cut with KpnI/PstI and the 300 bp insert was purified with the QIAquick Gel Extraction Kit from Qiagen. 5 ml (100 ng) of the insert was labeled with $^{32}$P by "random priming" using the Oligolabelling Kit from Pharmacia and purified using a Pharmacia Sephadex G-50 NICK column. Hybridization was performed in Church buffer (500 mM phosphate buffer, 7% SDS, 1 mM EDTA and 1% BSA) for 16 h at 65° C. The filters were washed 3 times for 15 min with 40 mM phosphate buffer, 5% SDS and 1 mM EDTA at 65° C., followed by 3 washes for 15 min with 40 mM phosphate buffer, 2% SDS and 1 mM EDTA at 65° C. and three washes for 15 min at 60° C. with 40 mM phosphate buffer, 1% SDS and 1 mM EDTA. Over 300 positive phage clones were identified from the first screening. A second and third screen was carried out with 12 hybridizing clones (giving different strength of hybridization signals) following the same hybridization and wash conditions as outlined above. Out of these 12 clones, 8 were confirmed as positives following the second and third rounds of screening. Plasmid clones were generated from each positive phage plaque by in vivo excision, using ExAssist helper phage and *E. coli* strain SOLR, according to the ZAP-cDNA Gigapack III Gold Cloning Kit manual (Stratagene).

DNA sequence analysis of the corresponding inserts was performed with the ABI PRISM 377XL DNA Sequencer using the BigDye Terminator Kit (Perking Elmer) and T3 and T7 primers. DNA sequence analysis of the 5' and 3' ends of these clones indicated that 6 of the 8 positive phage clones contained the predicted full-length sequence of the putative oxidosqualene cyclase from *A. strigosa*, and that the clones shared identity at the 5' (388 bp) and 3' (328 bp) ends. These clones were named amy7As, amy10As, amy11As, amy15As, amy16As and amy23As (see Annexes IV and V).

In order to obtain the complete sequence of the full length oxidosqualene cyclase cDNA we used 4 forward primers from different regions of the cDNA.

ASEQ1: GCATTGGCCTGGTGATTA, (SEQ ID NO: 1)
ASEQ2: GCCCATGAGGTGGTCACA, (SEQ ID NO: 2)
ASEQ3: GGCGCGTGATTATTGTGC, (SEQ ID NO: 3)
ASEQ4: CATGAACTCGTGCGCCTT. (SEQ ID NO: 4)

The cDNA was also digested with different restriction enzymes. The following restriction fragments were ligated individually into the pBluescript SK+ vector (Stratagene): two EcoRI fragments of 1100 bp and 200 bp respectively; one EcoRI/XbaI fragment of 1300 bp; one HindIII/XbaI fragment of 2300 bp and one HindIII/BamHI fragment of 300 bp.

These five subclones were also used to determine the complete sequence of the putative oxidosqualene cyclase cDNA (Annex I) together with part of the untranslated 3' and 5' sequences. The initiation and termination of translation points are shadowed.

Primary structure analysis was carried out with the ProtParam Tool at the "Expert Protein Analysis System" (ExPASy) proteomics server of the Swiss Institute of Bioinformatics (SIB). The deduced amino acid sequence revealed a protein of 757 amino acids, a predicted molecular weight (MW) of 86860.8 dalton and a theoretical pI of 5.99 (Annex II).

Computational analysis (ScanProsite Tool, ExPASy) revealed the existence of 4 conserved QW motifs with the consensus structure [K/R][G/A]X2-3[F/Y/W][L/I/V] X3QX2-5GXW (Poralla et al. TIBS 19, 157–158, 1994), which is characteristic for oxidosqualene cyclases.

The characteristic consensus sequence DCTAE (underlined) of the putative active site of the enzyme is also present in a similar position to that of other plant triterpene cyclases in the databanks (Abe I and Prestwich GD, Lipids 30, no.3, 1995). The Annexes below give the complete deduced amino acid sequence of the *A. strigosa* oxidosqualene cyclase cDNA, the alignment of the DCTAE motif in the predicted amino acid sequences of triterpene biosynthetic enzymes of different species, and the alignment of the *A.* predicted oxidosqualene cyclase with artenol synthase of *A. strigosa*.

Example 3

Further Evidence that the cDNA Does Encode β-amyrin Synthase

1) Expression in Yeast

The oxidosqualene cyclase cDNA was demonstrated to encode β-amyrin synthase by expression in yeast (*Saccharomyces cerevisiae*). Two complete cDNA clones (amy10As and amy15As), containing different lengths of the 5' untranslated leader sequence were digested with BamHI/XbaI. The inserts were purified with the QIAquick Gel Extraction Kit from Qiagen and ligated into the BamHI/XbaI site of the pYES2 expression vector (Invitrogen) downstream of the Gal1 promoter. These clones were transformed into the GIL77 (Gollub EG et al. J Biol Chem 252, 2846–2854, 1977) yeast mutant strain by the lithium acetate method (Rose MD et al. Cold Spring Harbor Laboratory Press, New York, N.Y., 1990). The GIL77 mutant strain is an ergosterol auxotroph and lacks lanosterol synthase activity. Therefore it accumulates 2,3-oxidosqualene. Selection of the transformants was done on SC-U medium [1.7 g/lt Yeast Nitrogen Base (Difco), 5 g/lt $(NH_4)_2SO_4$ (SIGMA), 20 g/lt raffinose (BDH), 0.77 g/lt Uracil Drop Out Supplement (Clontech), 20 mg/ml ergosterol (SIGMA),13 mg/ml hemin (SIGMA) and 5 mg/ml Tween 80 (SIGMA)] at 30° C. Transformants were grown in 50 ml complete YPD liquid medium (Clontech) supplemented with ergosterol (20 mg/ml), hemin (13 mg/ml) and Tween 80 (5 mg/ml) at 30° C. for 60 h. The cells were centrifuged and resuspended in 50 ml SC-U liquid medium containing instead of raffinose, 2% galactose (BDH). The culture was grown for 24 h at 30° C. with shaking (200 rpm). Cells were collected by centrifugation and refluxed with 3 ml 20% KOH/50% ethanol for 10 min at 95° C. The solution was extracted twice with hexane and the supernatant was freeze-dried in a spin-vacuum. The pellet was resuspended in 120 ml of HPLC-grade methanol (BDH) and 20 ml were analyzed on a normal phase silica gel TLC plate (MERCK) which was developed with 1:1 hexane/ethylacetate (BDH). The TLC plate was visualized by anisaldehyde staining (96% acetic acid, 2% sulphuric acid and 2% p-anisaldehyde, SIGMA) after incubating the plate for 5 min at 160° C. (Saponins, K Hostettmann and A Marston (eds.), Cambridge University Press, 1995). In order to confirm the Rf value of the products, 10 mg of β-amyrin and cycloartenol (Apin Chemicals Ltd) standards were also loaded on the TLC. As a positive and negative control we used pYES2 constructs harboring the β-amyrin or cycloartenol synthase cDNAs from *Panax ginseng* respectively (Kushiro et al. Eur J Biochem 256, 238–244, 1998). Both putative oxidosqualene cyclase cDNAs (amy10As and amy15As) were successfully expressed in yeast and confirmed to encode *A. strigosa* β-amyrin synthase.

2) Expression in Sad Mutants

Total RNA was extracted from root tissue of 9 saponin-deficient *A. strigosa* mutants (numbers 610, 109, 1027, 791, 825, 616, 376, 1139 and 9; Proc Natl Acad Sci 96, 12923–12928, 1999) using the RNeasy Plant Mini Kit from Qiagen. The RNA was analyzed on a 1.2% formaldehyde agarose gel and transferred on Hybond-N+ membrane (Amersham) with 20×SSC (3M NaCl, 0.3M Sodium citrate, BDH) by standard procedures (Sambrook J et al. Molecular Cloning: A Laboratory Manual. Cold Spring Harbor Laboratory Press, Cold Spring Harbor, 1989). The amy10As clone was cut with BamHI/XbaI and the insert was purified with the QIAquick Gel Extraction Kit from Qiagen. 4 ml (100 ng) of the insert was labeled with 32P by "random priming" using the Oligolabelling Kit from Pharmacia and purified using a Pharmacia Sephadex G-50 NICK column. Hybridization was performed in Church buffer (500 mM phosphate buffer, 7% SDS, 1 mM EDTA and 1% BSA) for 16 h at 65° C. The filters were washed 3 times for 15 min with 40 mM phosphate buffer, 5% SDS and 1 mM EDTA at 65° C., followed by 3 washes for 15 min with 40 mM phosphate buffer, 2% SDS and 1 mM EDTA at 65° C. and one wash for 15 min at RT with 40 mM phosphate buffer, 1% SDS and 1 mM EDTA. Mutants 610 and 109 represent different mutant alleles at the Sad1 locus, and both lack detectable levels of β-amyrin synthase. The results of the northern blot analysis showed that the β-amyrin synthase mRNA levels are substantially reduced in sad1 mutants, but not in the other sad mutants (all of which have β-amyrin synthase activity).

Example 4

Isolation of the Genomic Aclone of the β-amyrin Synthase from *A. strigosa*.

In order to clone the full genomic sequence of the β-amyrin synthase from *Avena strigosa* a primer pair was designed, based on the cDNA sequence.

Primer AMYstaF5 (5'-CCATGTGGAGGCTAACAAT-AGGTGAGGG-3'; SEQ ID NO: 5) containing the initiation of translation start codon from the 5' end and, primer ANYendR5 (5'-TATTTCTCAAAGAAAATAACGCAT-GAATGCTC; SEQ ID NO:6) from the untranslated 3' end were used.

Approximately 400 ng of high molecular weight genomic DNA were used as template in a 50 µl reaction with 350 µM dNTPs, 300 nM of each primer and 2.5 units of Expand™ Long Template polymerase (Roche). Reaction conditions were 94° C. for 2min, 94° C. for 10 sec, 65° C. for 30 sec, 68° C. for 6 min for a total of 9 cycles, following by 94° C. for 10 sec 65° C. for 30 sec, 68° C. for 6 min+20 sec/cycle for a total of 19 cycles and a final cycle of 68° C. for 7 min. A single band of about 7.4 Kb was excised from the gel and purified with the Gel Extraction Kit from Qiagen. The purified band was tailed for 30 min at 70° C. in a 50 µl reaction using 200 µM of dATP and 5 units of Taq DNA polymerase (Gibco-BRL). For the ligation reaction 2 µl of the tailed band were mixed with 1 µl of pGEM-T vector (Promega) in a final volume of 10 µl. Ligation was performed with 3 units of T4 DNA ligase (Promega) O/N at 4° C. The ligation mix was purified with the PCR Purification Kit from Qiagen and 1 µl was used to transform 10 µl of DH10B cells (Gibco-BRL) according to the manufacture instructions. Two independent clones were subjected to automated sequencing using the ABI PRISM 377XL DNA Sequencer and the BigDye Terminator Kit (Perking Elmer). The primers shown in Table 3 were used in order to cover the complete genomic sequence at least two times.

Example 5

Isolation of the Promoter of β-amyrin Synthase from *A. Strigosa*

In order to isolate the sequence of the β-amyrin synthase regulating gene expression, we used a modified procedure of the "Extender PCR" (A J H Brown et al.) and the "GenomeWalker" (Clontech) protocol. Initially a forward primer:
ADPR-ApaF : 5'-TGCGAGTAAGGATCCTCACG-CAAGGAATTCCGACCAGACAGGCC-3' (SEQ ID NO: 7) and a reverse primer ADPR-ApaR : 3'-H2N -CTGTC-CGG-PO4-5' were designed in order to generate a synthetic adaptor.

Approximately 6 nmoles of each primer were mixed with 10 µl of 10X ligation buffer (Roche) in a 100 µl final reaction volume. The primers were annealed in a PTC-200 Thermal Cycler (MJ-Research) using the following conditions : 950° C. for 3 min, 93.50° C. for 1 min –1.5° C./cycle for a total of 48 cycles.

In order to generate the "libraries" for the PCR amplification, 5–6 µg of high molecular weight genomic DNA from *A. strigosa* were digested with the DraI, EcoRV, PvuII, ScaI and StuI restriction enzymes (Roche). The reactions were performed in a final volume of 100 µl with 80 units of each enzyme for 16 h at 37° C. After digestion the DNA from each "library" was purified using the PCR Purification Kit (Qiagen) and resuspended in a final volume of 28 µl of Tris-HCl pH8.5. 4 µl (600 ng) of DNA from each library was mixed with 0.8 µl (50 pmol) of the synthetic adaptor in a final volume of 8 µl. Ligation was performed overnight (16 h) at 16° C. with 5 units of T4 DNA ligase (Roche). The adaptor ligated DNA from each library was diluted with 72 µl of sterile dH$_2$O and stored at –20° C.

Amplification of target sequence from each "library" was carried out using 10 ng of adaptor-ligated template DNA, 20 pmol of adaptor primer:
PR11F (5'-TGCGAGTAAGGATCCTCACGCAAG-3'; SEQ ID NO: 8) combined with an β-amyrin-specific primer:
ANY8R (5'-TCAGCCACGGACCGCCGCCCTCAC-CTATT-3' SEQ ID NO: 9), 200 pM of dNTPs and 1 unit of Expand High Fidelity DNA polymerase (Roche). Reaction conditions were 940° C. for 3 min, 94° C. for 25s, 720° C. for 3 min for a total of 7 cycles following by 94° C. for 25s, 67° C. for 3 min for a total of 31 cycles and a final cycle of 67° C. for 7 min. A 1/50 dilution of each PCR reaction was used in order to perform a second round of amplification using the nested adaptor primer: PR22F (5'-CACGCAAG-GAATTCCGACCAGACA-3'; SEQ ID NO: 10), and a second β-amyrin-specific primer, AMY9R (5'-TTAGCCTCCA-CATGGTGCGCACCAACAACG-3'; SEQ ID NO: 11).

Reaction conditions were 94° C. for 3 min, 94° C. for 25s, 72° C. for 3 min for a total of 5 cycles following by 94° C. for 25s, 67° C. for 3 min for a total of 20 cycles and a final cycle of 67° C. for 7 min. All PCR products were subsequently size fractionated on a 1% agarose gel. Three single bands of 1.4 Kb, 1.0 Kb and 0.7 Kb were excised from the DraI, EcoRV and StuI "library" respectively and purified with the Gel Extraction Kit from Qiagen. The DNA fragments were tailed for 30 min at 70° C. in a 50_1 reaction using 200 µM of dATP and 5 units of Taq DNA polymerase (Gibco-BRL). For the ligation reaction 2 µl of the tailed band were mixed with 1_1 of pGEM-T vector (Promega) in a final volume of 10 µl. Ligation was performed with 3 units of T4 DNA ligase (Promega) for 2 h at RT. The ligation mix was purified with the PCR Purification Kit from Qiagen and 1 µl was used to transform 10 µl of DH10B cells (Gibco-BRL) according to the manufacture's instructions. Two independent clones from each band were subjected to automated sequencing using the ABI PRISM 377XL DNA Sequencer and the BigDye Terminator Kit (Perking Elmer). The 76 bp of sequence directly upstream of the β-amyrin-specific AMY9R primer site was identical to that predicted from the 5' end of the *A. strigosa* β-amyrin cDNA sequence in all three clones. This sequence was followed by approximately 1.25 kb of novel sequence in the DraI fragment, 0.85 kb in the EcoRV fragment and 0.55 kb in the StuI fragment. All fragments included a TATA box sequence 92 bp upstream of the initiation of translation start codon (ATG), indicating that this was likely to be the promoter region of the gene.

In order to isolate more novel sequences of the regulatory region of the β-amyrin synthase gene a second upstream walk was carried out using the same adaptor-ligated "libraries".

Two new β-amyrin-specific primers, AMYPRO10R (5'-GGACATCGAGGTGGTTGCATTTTAGTGGATC-3'; SEQ ID NO: 12) and AMYPR011R (5'-GGTGCTCTTGCT-TGTTCTATGGCCTCGTCTTT-3'; SEQ ID NO: 13) were designed based on the isolated 1.25 kb promoter sequence. For the first and second PCR amplification primer PR11F in combination with primer AMYPRO1OR and primer PR22F in combination with primer AMYPR011R were used respectively.

Reaction conditions were identical to that described earlier for the first upstream walk. This generated a single band product of approximately 950 bp in the EcoRV "library". The band was excised from the gel and purified with the Gel Extraction Kit from Qiagen. After the standard tailing reaction (described earlier) the fragment was ligated into the pGEM-T vector (Promega). The ligation mix was purified with the PCR Purification Kit from Qiagen and 1 μl was used to transform 10 μl of DH10B cells (Gibco-BRL) according to the manufacture's instructions. Two independent clones were subjected to automated sequencing using the ABI PRISM 377XL DNA Sequencer and the BigDye Terminator Kit (Perking Elmer). The 200 bp of sequence directly upstream of the β-amyrin-specific AMY11R primer site was identical to that from the 1.25 kb DraI fragment isolated in the first walk, followed by 720 bp of novel sequence. This extended the 5' end of the gene by an additional 0.7 kb to give a total of approximately 1.9 kb of sequence upstream of the transcriptional start site.

Computational analysis of the promoter region using the MatInspector program at the Genomatix web page in Germany revealed several putative transcription factor binding sites (see Annex). Parameters used for the search were: Plant databank-section, Core similarity 0.75 and Matrix similarity 0.85. The resulting statistics were:

| | | | |
|---|---|---|---|
| In 0 seq. | 0 | matches to P$AG_01 | (Agamous) |
| In 1 seq. | 5 | matches to P$ATHB1_01 | (Arabidopsis thaliana homeo box protein 1) |
| In 1 seq. | 19 | matches to P$DOF1_01 | (Dof1/MNB1a-single zinc finger transcription factor) |
| In 1 seq. | 8 | matches to P$GAMYB_01 | (GA-regulated myb gene from barley) |
| In 1 seq. | 2 | matches to P$GBP_Q6 | (G-box binding proteins) |
| In 1 seq. | 1 | matches to P$MYBPH3_01 | (Myb-like protein of Petunia hybrida) |
| In 0 seq. | 0 | matches to P$O2_01 | (Opaque-2) |
| In 1 seq. | 19 | matches to P$PBF_01 | (PBF (MPBF)) |
| In 1 seq. | 4 | matches to P$P_01 | (maize activator P of flavonoid biosynthetic genes) |
| In 1 seq. | 5 | matches to P$SBF1_01 | (SBF-1) |
| In 0 seq. | 0 | matches to P$bZIP910_01 | (bZIP transcription factor from Antirrhinum majus) |

REFERENCES

Brown A J H, Perry S J, Saunders S E and Burke J F (1999) Extender PCR: A method for the isolation of sequences regulating gene expression from genomic DNA. BioTechniques 26 (5), 804–806.

Quandt K, Frech K, Karas H, Wingender E and Werner T (1995) MatInd and MatInspector—New fast and versatile tools for detection of consensus matches in nucleotide sequence data. Nucleic Acids Research 23, 4878–4884.

```
                  Annexes—Sequences & BLAST results
     (I) OAT β-amyrin synthase cDNA (nucleotide sequence) SEQ ID NO: 14

1        10        20        30        40        50        60        70

ATTGCTTGTTTTCCTCGCATACACTGCCCGTTGTTGGTGCGCACCATGTGGAGGCTAACAATAGGTGAGGG

CGGCGGTCCGTGGCTGAAGTCGAACAATGGCTTCCTTGGCCGCCAAGTGTGGGAGTACGACGCCGATGCCG

GCACGCCGGAAGAGCGTGCCGAGGTTGAGAGGGTGCGTGCGGAATTCACAAAGAACAGGTTCCAGAGGAAG

GAGTCACAGGACCTTCTTCTACGCTTGCAGTACGCAAAAGACAACCCTCTTCCGGCGAATATTCCGACAGA

AGCCAAGCTTGAAAAGAGTACAGAGGTCACTCACGAGACTATCTACGAATCATTGATGCGAGCTTTACATC

AATATTCCTCTCTACAAGCAGACGATGGGCATTGGCCTGGTGATTACAGTGGGATTCTCTTCATTATGCCT

ATCATTATATTCTCTTTATATGTTACTAGATCACTTGACACCTTTTTATCTCCGGAACATCGTCATGAGAT

ATGTCGCTACATTTACAATCAACAGAATGAAGATGGTGGTTGGGGAAAAATGGTTCTTGGCCCAAGTACCA

TGTTTGGATCGTGTATGAATTATGCAACCTTAATGATTCTTGGCGAGAAGCGAAATGGTGATCATAAGGAT

GCATTGGAAAAAGGGCGTTCTTGGATTTTATCTCATGGAACTGCAACTGCAATACCACAGTGGGGAAAAAT

ATGGTTGTCGATAATTGGCGTTTACGAATGGTCAGGAAACAATCCTATTATACCTGAATTGTGGTTGGTTC

CACATTTTCTTCCGATTCACCCAGGTCGTTTTTGGTGTTTTACCCGGTTGATATACATGTCAATGGCATAT
```

-continued

Annexes—Sequences & BLAST results
(I) OAT β-amyrin synthase cDNA (nucleotide sequence) SEQ ID NO: 14

```
CTCTATGGTAAGAAATTTGTTGGGCCTATTAGTCCTACAATATTAGCTCTGCGACAAGACCTCTATAGTAT
ACCTTACTGCAACATTAATTGGGACAAGGCGCGTGATTATTGTGCAAAGGAGGACCTTCATTACCCACGCT
CACGGGCACAAGATCTTATATCTGGTTGCCTAACGAAAATTGTGGAGCCAATTTTGAATTGGTGGCCAGCA
AACAAGCTAAGAGATAGAGCTTTAACTAACCTCATGGAGCATATCCATTATGACGACGAATCAACCAAATA
TGTGGGCATTTGCCCTATTAACAAGGCATTGAACATGATTTGTTGTTGGGTAGAAAACCCAAATTCGCCTG
AATTCCAACAACATCTTCCACGATTCCATGACTATTTGTGGATGGCGGAGGATGGAATGAAGGCACAGGTA
TATGATGGATGTCATAGCTGGGAACTAGCGTTCATAATTCATGCCTATTGTTCCACGGATCTTAGTAGCGA
GTTTATCCCGACTCTAAAAAAGGCGCACGAGTTCATGAAGAACTCACAGGTTCTTTTCAACAACCCAAATC
ATGAAAGCTATTATCGCCACAGATCAAAAGGCTCATGGACCCTTTCAAGTGTAGATAATGGTTGGTCTGTA
TCTGATTGTACTGCGGAAGCTGTTAAGGCATTGCTACTATTATCAAAGATATCCGCTGACCTTGTTGGCGA
TCCAATAAAACAAGACAGGTTGTATGATGCCATTGATTGCATCCTATCTTTCATGAATACAGATGGAACAT
TTTCTACCTACGAATGCAAACGGACATTCGCTTGGTTAGAGGTTCTCAACCCTTCTGAGAGTTTTCGGAAC
ATTGTCGTGGACTATCCATCTGTTGAATGCACATCATCTGTGGTTGATGCTCTCATATTATTTAAAGAGAC
GAATCCACGATATCGAAGAGCAGAGATAGATAAATGCATTGAAGAAGCTGTTGTATTTATTGAGAACAGTC
AAAATAAGGATGGTTCATGGTATGGCTCATGGGGTATATGTTTCGCATATGGATGCATGTTTGCAGTAAGG
GCGTTGGTTGCTACAGGAAAAACCTACGACAATTGTGCTTCTATCAGGAAATCATGCAAATTTGTCTTATC
AAAGCAACAAACAACAGGTGGATGGGGTGAAGACTATCTTTCTAGTGACAATGGGGAATATATTGATAGCG
GTAGGCCTAATGCTGTGACCACCTCATGGGCAATGTTGGCTTTAATTTATGCTGGACAGGTTGAACGTGAC
CCAGTACCACTGTATAATGCTGCAAGACAGCTAATGAATATGCAGCTAGAAACAGGTGACTTCCCCCAACA
GGAACACATGGGTTGCTTCAACTCCTCCTTGAACTTCAACTACGCCAACTACCGCAATCTATCCCGATTAA
TGGCTCTTGGGGAACTTCGCCGTCGACTTCTTGCGATTAAGAGCTGATATGGAAACAAACATGGATGTCTA
GGCTGCGAGGAATAAGAACATTGCTCCCACGAGCATTCATGCGTTATTTTCTTTGAGAAATAAGTTCTCTT
CCTACCGATGTCATCATGTAACTTTTCGGAATATTTTATGTGT
```

(II)—OAT β-amyrin synthase cDNA (amino acid sequence) SEQ ID NO: 15

```
MWRLTIGEGGGPWLKSNNGFLGRQVWEYDADAGTPEERAEVERVRAEFTKNRFQRKESQDLLLRLQYAKDNPLPA
NIPTEAKLEKSTEVTHETIYESLMRALHQYSSLQADDGHWPGDYSGILFIMPINIFSLYVTRSLDTFLSPEHRHE
ICRYIYNQQNEDGGWGKMVLGPSTMFGSCMNYATLMILGEKRNGDHKDALEKGRSWILSHGTATAIPQWGKIWLS
IIGVYEWSGNNPIIPELWLVPHFLPIHPGRFWCFTRLIYMSMAYLYGKKFVGPISPTILALRQDLYSIPYCNINW
DKARDYCAKEDLHYPRSRAQSDLISGCLTKIVEPILNWWPANKLRDRALTNLMEHIHYDESTKVVGICPINKALN
MICCWVENPNSPEFQQHLPRFHDYLWMAEDGMKAQVYDGCHSWELAFIIHAYCSTDLTSEFIPTLKKAHEFMKNS
QVLFNHPNHESYYRHRSKGSWTLSSVDNGWSVSDCTAAEAVKALLLLSKISADLVGDPIKQDRLYDAIDCILSFMN
TDGTFSTYECKRTFAWLEVLNPSESFRNIVVDYPSVECTSSVVDALILFKETNPRYRRAEIDKCIEEAVVFIENS
QNKDGSWYGSWGICFAYGCMFAVRALVATGKTYDNCASIRKSCKFVLSKQQTTGGWGEDYLSSDNGEYIDSGRPN
AVTTSWAMLALIYAGQVERDPVPLYNAARQLMNMQLETGDFPQQEHMGCFNSSLNFNYANYRNLYPIMALGELRR
RLLAIKS
```

| (III)—ortls.pk001.c14 (putative oxiclosqualene cyclase EST clone from *Avena strigosa*) (SEQ ID NO: 16) |
|---|
| ACAGAGGTCACTCACGAGACTATCTACGAATCATTGATGCGAGCTTTACA |
| TCAATATTCCTCTCTACAAGCAGACGATGGGCATTGGCCTGGTGATTACA |
| GTGGGATTCTCTTCATTATGCCTATCATTATATTCTCTTTATATGTTACT |
| AGATCACTTGACACCTTTTTATCTCCGGAACATCGTCATGAGATATGTCG |
| CTACATTTACAACCAACAGAATGAAGATGGTGGTTGGGGAAAAATGGTTC |
| TTGGCCCAACGT |

(IV)—CLUSTAL W (1.8) multiple sequence alignment of 6 clones encoding the 5' end of the putative oxidosqualene cyclase from *A. strigosa* (amy16as: SEQ ID NO: 17; amy23as: SEQ ID NO: 18; amy7As: SEQ ID NO: 19; amy11As: SEQ ID NO: 20; amy10As: SEQ ID NO: 21; amy15As: SEQ ID NO: 22)

```
amy16As  ACCATGTGGAGGCTAACAATAGGTGAGGGCGGCGGTCCGTGGCTGAAGTCGAACAATGGC  60
amy23As  ACCATGTGGAGGCTAACAATAGGTGAGGGCGGCGGTCCGTGGCTGAAGTCGAACAATGGC  60
amy7As   ACCATGTGGAGGCTAACAATAGGTCAGGGCGGCGGTCCGTGGCTGAAGTCGAACAATGGC  60
amy11As  ACCATGTGGAGGCTAACAATAGGTGAGGGCGGCGGTCCGTGGCTGAAGTCGAACAATGGC  60
amy10As  ACCATGTGGAGGCTAACAATAGGTGAGGNCGGCGGTCCGTGGCTGAAGTCGAACAATGGC  60
amy15As  ACCATGTGGAGGCTAACAATAGGTGAGGGCGGCGGTCCGTGGCTGAAGTCGAACAATGGC  60
         **********************  ******************************** amy16As  TTCCTTGGCCGCCAAGTGTGGGAGTACGACGCCGATGCCGGCACGCCGGAAGAGCGTGCC  120
amy23As  TTCCTTGGCCGCCAAGTGTGGGAGTACGACGCCGATGCCGGCACGCCGGAAGAGCGTGCC  120
amy7As   TTCCTTGGCCGCCAAGTGTGGGAGTACGACGCCGATGCCGGCACGCCGGAAGAGCGTGCC  120
amy11As  TTCCTTGGCCGCCAAGTGTGGGAGTACGACGCCGATGCCGGCACGCCGGAAGAGCGTGCC  120
amy10As  TTCCTTGGCCGCCAAGTGTGGGAGTACGACGCCGATGCCGGCACGCCGGAAGAGCGTGCC  120
amy15As  TTCCTTGGCCGCCAAGTGTGGGAGTACGACGCCGATGCCGGCACGCCGGAAGAGCGTGCC  120
         **************************************** *************** amy16As  GAGGTTGAGAGGGTGCGTGCGGAATTCACAAAGAACAGGTTCCA-GAGGAAGGAGTCACA  179
axny23As GAGGTTGAGAGGGTGCGTGCGGAATTCACAAAGAACAGGTTCCA-GAGGAAGGAGTCACA  179
amy7As   GAGGTTGAGAGGGTGCGTGCGGAATTCACAAAGAACAGGTTCCA-GAGGNAGGAGTCACA  179
amy11As  GAGGTTGAGAGGGTGCGTGCGGAATTCACAAAGAAcAGCTTCCA-GAGGAAGGAGTCACA  179
amy10As  GAGGTTGAGAGGGTGCGTGCGGAATTCACAAAGAACAGGTTCCA-GAGGAAGGAGTCACA  179
amy15As  GAGGTTGAGAGGGTGCGTGCGGAATTCACAAAGAACAGGTTCCNAGAGGAAGGAGTCACA  180
         ****************************************   ******* amy16As  GGACCTTCTTCTACGCTTGCAGTACGCAAAAGACAACCCTCTTCCGGCGAATATTCCGAC  239
axny23As GGACCTTCTTCTACGCTTGCAGTACGCAAAAGACAACCCTCTTCCGGCGAATATTCCGAC  239
amy7As   GGACCTTCTTCTACGCTTGCAGTACGCAAAAGACAACCCTCTTCCGGCGAATATTCCGAC  239
amy11As  GGACCTTCTTCTACGCTTGCAGTACGCAAAAGACAACCCTCTTCCGGCGAATATTCCGAC  239
```

-continued (IV)—CLUSTAL W (1.8) multiple sequence alignment of 6
clones encoding the 5' end of the putative oxidosqualene
cyclase from A. strigosa (amy16as: SEQ ID NO: 17;
amy23as: SEQ ID NO: 18; amy7As: SEQ ID NO: 19; amy11As:
SEQ ID NO: 20; amy10As: SEQ ID NO: 21; amy15As: SEQ ID NO: 22)

```
amy10As  GGACCTTCTTCTACGCTTGCAGTACGCAAAAGACAACCCTCTTCCGGCGAATATTCCGAC  239 amy15As  GGACCTTCTTCTACGCTTGCAGTACGCAAAAGACAACCCTCTTCCGGCGAATATTCCGAC  240

********  *********************************************** amy16As  NGAAGCCAAGCTTGAAAAGAGTACAGAGGTCACTCACGAGACTATCTACGAATCATTGAT  299 amy23As  AGAAGCCAAGCTTGAAAAGAGTACAGAGGTCACTCACGAGACTATCTACGAATCATTGAT  299 amy7As   AGAAGCCAAGCTTGAAAAGAGTACAGAGGTCACTCACGAGACTATCTACGAATCATTGAT  299 amy11As  AGAAGCCAAGCTTGAAAAGAGTACAGAGGTCACTCACGAGACTATCTACGAATCATTGAT  299 amy10As  AGAAGCCAAGCTTGAAAAGAGTACAGAGGTCACTCACGAGACTATCTACGAATCATTGAT  299 amy15As  AGAAGCCAAGCTTGAAAAGAGTACAGAGGTCACTCACGAGACTATCTACGAATCATTGAT  300

*********************************************************** amy16As  GCGAGCTCTACATCAATATTCCTCTTTACAAGCAGACGATGGGCATTGGCCTGGTGATTA  359 amy23As  GCGAGCTCTACATCAATATTCCTCTTTACAAGCAGACGATNGGCATTGGCCTGGTGATTA  359 amy7As   GCGAGCTCTACATNAATATTCCTCTTTACAAGCAGACGATGGGCATTGGCCTGGTGATTA  359 amy11As  GCGAGCTCTACATCAATATTCCTCTTTACAAGCAGACGATGGGCATTGGCCTGGTGATTA  359 amy10As  GCGAGCTCTACANCAATATTCCTCTTTACAAGCAGACGATGGGCATTGGCCTGGTGATTA  359 amy15As  GCGAGCTCTACATCAATATTCCTCTTTACAAGCAGACGATGGGCATTGGCCTGGTGATTA  360

********** ************************* **************** amy16As  CAGTGGGATTCTCTTCATTATGCCTATCA  388 amy23As  CAGTGGGATTCTCTTCATTATGCCTATCA  388 amy7As   CAGTGGGATTCTCTTCATTATGCCTATCA  388 amy11As  CAGTGGGATTCTCTTCATTATGCCTATCA  388 amy10As  CAGTGGGATTCTCTTCATTATGCCTATCA  388 amy15As  CAGTGGGATTCTCTTCATTATGCCTATCA  389

*****************************
```

(V)—CLUSTAL W (1.8) multiple sequence alignment of 6 clones
encoding the 3' end of the putative oxidosqualene cyclase
from A. strigosa (amy16as: SEQ ID NO: 23; amy23as:
SEQ ID NO: 24; amy7As: SEQ ID NO: 25; amy11As: SEQ ID NO: 26; amy10As:
SEQ ID NO: 27; amy15As: SEQ ID NO: 28)

```
amy11As  CATAAAATATTCCGAAAAGTTACATGATGACATCGGTAGGAAGAGAACTTATTTCTCAAA  60 amy15As  CATAAAATATTCCGAAAAGTTACATGATGACATCGGTAGGAAGAGAACTTATTTCTCAAA  60 amy23As  CATAAAATATTCCGAAAAGTTACATGATGACATCGGTAGGAAGAGAACTTATTTCTCAAA  60 amy10As  CATAAAATATTCCGAAAAGTTACATGATGACATCGNTAGGAAGAGAACTTATTTCTCAAA  60 amy7As   CATAAAATATTCCGAAAAGTTACATGATGACATCGGTAGGAAGAGAACTTATTTCTCAAA  60 amy16As  CATAAAATATTCCGAAAAGTTACATGATGACATCGGTAGGAAGAGAACTTATTTCTCAAA  60

********************************* **********************
```

(V)—CLUSTAL W (1.8) multiple sequence alignment of 6 clones
encoding the 3' end of the putative oxidosqualene cyclase
from A. strigosa (amy16as: SEQ ID NO: 23; amy23as:
SEQ ID NO: 24; amy7As: SEQ ID NO: 25; amy11As: SEQ ID NO: 26; amy10As:
SEQ ID NO: 27; amy15As: SEQ ID NO: 28)

```
amy11As  GAAAATAACGCATGAATGCTCGTGGGAGCAATGTTCTTATTCCTCGCAGCCTAGACATCC  120 amy15As  GAAAATAACGCATGAATGCTCGTGGGAGCAATGTTCTTATTCCTCGCAGCCTAGACATCC  120 amy23As  GAAAATAACGCATGAATGCTCGTGGGAGCAATGTTCTTATTCCTCGCAGCCTAGACATCC  120 amy10As  GAAAATAACGCATGAATGCTCGTGGGAGCAATGTTCTTATTCCTCGCAGCCTAGACATCC  120 amy7As   GAAAATAACGCATGAATGCTCGTGGGAGCAATGTTCTTATTCCTCGCAGCCTAGACATCC  120 amy16As  GAAAATAACGCATGAATGCTCGTGGGAGCAATGTTCTTATTCCTCGCAGCCTAGACATCC  120
         **************************** *********** amy11As  ATGTTTGTTTCCATATCAGCTCTTAATCGCAAGAAGNCGACGGCGAAGTTCCCCAAGNGC  180 amy15As  ATGTTTGTTTCCATATCAGCTCTTAATCGCAAGAAGNCGACGGCGAAGTTCCCCAAGAGC  180 amy23As  ATGTTTGTTTCCATATCAGCTCTTAATCGCAAGAAGTCGACGGCGAAGTTCCCCAAGAGC  180 amy10As  ATGTTTGTTTCCATATCAGCTCTTAATCGCAAGAAGTCGACGGCGAAGTTCCCCAAGAGC  180 amy7As   ATGTTTGTTTCCATATCAGCTCTTAATCGCAAGAAGTCGACGGCGAAGTTCCNCAAGAGC  180 amy16As  ATGTTTGTTTCCATATCAGCTCTTAATCGCAAGAAGTCGACGGCGAAGTTCCCCAAGAGC  180
         ************************************** *********** amy11As  CATAA-TCGGTATAGATTGCGGTAGTTGGCGTAGTTGAAGTTCAAGGAGG-AGTTGAAG   238 amy15As  CATAA-TCGGTATAGATTGCGGTAGTTGGCGTAGTTGAAGTTCAAGGAGG-AGTTGAAG   238 amy23As  CATANATCGGTATAGATTGCGGTAGTTGGCGTAGTTGAAGTTCAAGGAGG-AGTTGAAG   239 amy10As  CATAA-TCGGTATAGATTGCGGTAGTTGGCGTAGTTGAAGTTCAAGGAGG-AGTTGAAG   238 amy7As   CATAA-TCGGTATAGATTGCGGTAGTTGGCGTAGTTGAAGTTCAAGGAGG-AGTTGAAG   238 amy16As  CATNA-TCGGTATAGATTGCGGTAGTTGGCGTAGTTGAAGTTCAAGGANGGAGTTGAAG   239 amy11As  CAACCCATGTGTTCC-TGTTGGGGGAAGTCACCTGTTTCTAGCTGCATATTCATTAGCTG  297 amy15As  CAACCCATGTGTTCC-TGTTGGGGGAAGTCACCTGTTTCTAGCTGCATATTCATTAGCTG  297 amy23As  CAACCCATGTGTTNCCTGTTGGGGGAAGTCACCTGTTTCTAGCTGCATATTCATTAGCTG  299 amy10As  CAACCCATGTNTTCC-TGTTGGGGGAAGTCACCTGTTTCTAGCTGCATATTCATTAGCTG  297 amy7As   CAACCCATGTGTTCC-TGTTGGGGGAAGTCACCTGTTTCTAGCTGCATATTCATTAGCTG  297 amy16As  CAACCCATGTGTTCC-TGTTGGGGGAAGTCACCTGTTTCTAGCTCCATATTCATTAGCTG  298 amy11As  TCTTGCAGCATTATACAGGGGTACTGGGTCA  328 amy15As  TCTTGCAGCATTATACAGGGGTACTGGGTCA  328 amy23As  TCTTGCAGCATTATACAGGGGTACTGGGTCA  330 amy10As  TCTTGCAGCATTATACAGGGGTACTGGGTCA  328 amy7As   TCTTGCAGCATTATACAGGGGTACTGGGTCA  328 amy16As  TCTTGCAGCATTATACAGGGGTACTGGGTCA  329
```

(VI)—Alignment of the DCTAE motif in the predicted amino acid sequences of triterpene biosynthetic enzymes of different species
(RAT OSC: SEQ ID NO: 29; YEAST OSC: SEQ ID NO: 30; ARAB OSC: SEQ ID NO: 31; OAT CYC: SEQ ID NO 31; PANAX CYC: SEQ ID NO: 32; OAT AMY: SEQ ID NO: 33; PANAX AMY: SEQ ID NO: 34.

```
RAT    OSC        HKGGFPFSTLDGGWIVADDTAEALKAVLLL

YEAST  OSC   439  RKGAWGFSTKTQGYTVADCTAEAIKAIIMV

ARAB   OSC   466  SKGAWPFSTADHGWPISDCTAEGLKAALLL

OAT    CYC   467  SKGAWPFSTADHGWPISDCTAEGLKAALLL

PANAX  CYG   466  SKGAWPFSTADHGWPISDCTAEGFKAVLQL

OAT    AMY   467  SKGSWTLSSVDNGWSVSDCTAEAVKALLLL

PANAX  AMY   469  SKGSWTFSDQDHGWQVSDCTAEGLKCGLIF
```

(VII)—Alignment of the predicted oxidosqualene cyclase with cycloartenol synthase of *A. strigosa*
SEQ ID NOS: 15 and 35.

```
b-amyrin MWRLTIGEGGG-PWLKSNNGFLGRQVWEYDADAGTPEERAEVERVRAEFTKNRFQRKESQ  59
cycloart MWRLKIAEGGGDPWLRTKNAHVGRQVWEFDPEAGDPEALAAVEAARRDFAAGRHRLKHSS  60 b-amyrin DLLLRLQYAKDNPLPANIPTEAKLEKSTEVTHETIYESLMRALHQYSSLQADDGHWPGDY 119
cycloart DRLMRIQFEKENPLKLDLP-AIKLEENEDVTEEAVSTSLKRAISRFSTLQAHDGHWPGDY 119 b-amyrin SGILFIMPINIFSLYVTRSLDTFLSPEHRHEICRYIYNQQNEDGGWGKMVLGPSTMFGSC 179
cycloart GGPMFLMPGLLITLYVTGSLNTVLSPEHQKEIRRYLYNHQNEDGGWGLHIEGPSTMFGSA 179 b-amyrin MNYATLMILGEKRNGDHKDALEKGRSWILSHGTATAIPQWGKIWLSIIGVYEWSGNNPII 239
cycloart LTYVSLRLLGEGPES-GDGAMEKGRNWILDHGGATYITSWGKFWLAVLGVFDWSGNNPLP 238 b-amyrin PELWLVPHFLPIHPGRFWCFTRLIYMSMAYLYGKKFVGPISPTILALRQDLYSIPYCNIN 299
cycloart PEIWMLPYRLPIHPGRMWCHCRMVYLPMCYVYGKRFVGKITPLILELRNELYKTPYSKID 298 b-amyrin WDKARDYCAKEDLHYPRSRAQDLISGCLTKIVEPILNWWPANKLRDRALTNLMEHIHYDD 359
cycloart WDSARNLCAKEDLYYPHPLIQDILWATLHKFVEPVMMHWPGNKLREKALNHVMQHVHYED 358 b-amyrin ESTKYVGICPINKALNMICCWVENPNSPEFQQHLPRFHDYLWMAEDGMKAQVYDGCHSWE 419
cycloart ENTRYICIGPVNKVLNMLTCWIEDPNSEAFKLHIPRVHDYLWVAEDGMKMQGYNGSQLWD 418 b-amyrin LAFIIHAYCSTDLTSEFIPTLKKAHEFMKNSQVLFNHP-NHESYYRHRSKGSWTLSSVDN 478
cycloart TAFAVQAITATGLIDEFAPTLKLAHNFIKNSQVLDDCPGDLSYWYRHISKGAWPFSTADH 478 b-amyrin GWSVSDCTAEAVKALLLLSKISADLVGDPIKQDRLYDAIDCILSFMNTDGTFSTYECKRT 538
cycloart GWPISDCTAEGLKAALLLSKISPEIVGEPVEVNRLYDAVNCLMSWMNNNGGFATYELTRS 538 b-amyrin FAWLEVLNPSESFRNIVVDYPSVECTSSVVDALILFKETNPRYRRAEIDKCIEEAVVFIE 598
cycloart YAWLELINPAETFGDIVIDYPYVECTSAAIQALTSFKKLYPGHRRKDVDNCINKAANFIE 598 b-amyrin NSQNKDGSWYGSWGICFAYGCMFAVRALVATGKTYDNCASIRKSCKFVLSKQQTTGGWGE 658
cycloart SIQRSDGSWYGSWAVCFTYGTWEGVKALVAAGRTFKSSPAIRKACEFLMSKELPFGGWCK 658 b-amyrin DYLSSDNGEYIDSG--RPNAVTTSWAMLALIYAGQVERDPVPLYNAARQLMNMQLETGDF 716
cycloart SYLSCQDQVYTNLEGKHAHAVNTGWAMLTLIDAGQAERDPTPLHRAAKVLINLQSEDGEF 718 b-amyrin PQQEHMGCFNSSLNFNYANYRNLYPIMALGELRRRLLAIKS 757
cycloart PQQEIMGVFNKNCMISYSQYRDIFPVWALGEYRCRVLAAGK 759
```

| (VIII)—Genomic sequence of β-amyrin synthase from *Avena strigosa* (SEQ ID NO: 36) |
|---|
| ATGTGGAGGCTAACAATAGGTGAGGGCGGCGGTCCGTGGCTGAAGTCGAACAATGGCTTCCTTGGCCGCCAA |
| GTGTGGGAGTACGACGCCGATGCCGGCACGCCGGAAGAGCGTGCCGAGGTTGAGAGGGTGCGTGCGGAATTC |
| ACAAAGAACAGGTTCCAGAGGAAGGAGTCACAGGACCTTCTTCTACGCTTGCAGgtacatgcgtcttctttc |
| ccctacttccatatacacccagtaqtatatgttgccactgccgttagctctagctttaggactgagaaaagg |
| gctctcagataatccatatctctcttttagatggagggtttgcttttatttattattacatattgttcaatcc |
| ttgctgtgtatatcatcaactgcagTACGCAAAAGACAACCCTCTTCCGGCGAATATTCCGACAGAAGCCAA |
| GCTTGAAAAGAGTACAGAGGTCACTCACGAGACTATCTACGAATCATTGATGCGAGCTTTACATCAATATTC |
| CTCTCTACAAGCAGACGATGGGCATTGGCCTGGTGATTACAGTGGGATTCTCTTCATTATGCcTATcATTgt |
| aagtattttactattattttatgatacagcaatttggcaattaatatatgcatacgaggtttcttatttcgt |
| aaatactcaagacaatatagcatgtggaatcttataatttctataatgaatatgtaccgtcttgtgtgcgca |
| atacgtatactatattattccgctatgcatatagtattacataccaatattgatagatgttcaaaccaatta |
| tgaagagtttaactacaagatttaatatagtagtttctgttattctagcagcaagttacctccattaggttc |
| cqgaagttctactcttaccacctatatatatgtattattgcttatactaccttcgtctcaaagtttaagact |
| ttttttaaagtcaatttatggaaagtttgaactaactttttataaaactatcaagaactatgatattatatt |
| tgccatgtgaaaatatgttttattatgtatcaaagggtatggatttcgtaccgtaaatataatattgttgtc |
| taaaatcttggttgaactttacttagtttgacttttggaaagtatataagcc ttaaactttaaaatagacgt |
| agtaattcagatgcacttcactgatatcccgacaaaagtacaaaatacatttatggaatgtcaaatttattt |
| gaaaacaacacatttggtttagcttcaatatttcggaaaagaaaatatgaggagtgatttaaataagttctt |
| aaggttttcatgaaaaacaaatctgttatggggactttatgcaaaqagaacaagattggctcttagaaattt |
| ctttagatatgattaaattaaaatacagtgtttgcactaaaaccacatttggtttgatttgaatatttgaaa |
| gagatagaaaatcttgaacatttattttagggaatataggctttattactaccatcctatgtatcatcgat |
| ggtggctcatcacattgatcacaactctgaaaactaagaagtctccaacatttagacaatgatattggtttt |
| tcaaatttcagtaacacttacaagaattccgttgattttattctccatccgagaactcatttctcctctcct |
| aataatgatgcacatatatgatgggatcttttctttatgttgcagATATTCTCTTTATATGTTACTAGATCA |
| CTTGACACCTTTTTATCTCCGGAACATCGTCATGAGATATGTCGCTACATTTACAATCAACAGgcatgggat |
| taaacctaacacatatttccatatttgttttctatatgtttgtgattttgtgaccaaaataaaaacagtact |
| taatgcaacatatattgagcaqAATGAAGATGGTGGTTGGGGAAAAATGGTTCTTGGCCCAAGTACCATGTT |
| TGGATCGTGTATGAATTATGCAACCTTAATGATTCTTGGCGAGAAGCGAAATGGTGATCATAAGGATGcATT |
| GGAAAAAGGGCGTTCTTGGATTTTATCTCATGGAACTGCAACTGCAATACCACAGTGGGGAAAAATATGGTT |
| GTCGgtatgttaaataacacaagatatcaatgctcatatatgttctcttctgaactaacgttaaatcaacct |
| actatttgataacatcatagATAATTGGCGTTTACGAATGGTCAGGAAACAATCCTATTATACCTGAATTGT |
| GGTTGGTTCCACATTTTCTTCCGATTGACCCAGgtatttctatctagcttgcatatataacaaaattgttgt |
| agaacgcatgcttagaccatcattctgtggaattattctgtgcaatttgttgcttgtggaagcaatttaacc |
| atatatcaaacaaggaatattgaggcatggtacctgaaatagttttttgaaaaatacatgccgaaaaggaaa |
| tcaatgtttcaattaggcatgtttgcacgtagattccacaagattctcttgtatatgttttgatcttggaga |
| tacatgtatatatttatgtatctttcatattatctcaaaaaaataacatgttactaccccctctatccataa |
| taagtgtcggtcacttagtacaaactttatactagcttagtacaaaatggacgactcttattatggattgca |
| gggagtactaaatattatgaagttgaaccttatcattcacaagtaatttattggaaaataatccttcatatg |

-continued (VIII)—Genomic sequence of β-amyrin synthase from *Avena strigosa*
(SEQ ID NO: 36)

tagGTCGTTTTTGGTGTTTTACCCGGTTGATATACATGTCAATGGCATATCTCTATGGTAAGAAATTTGTTG

GGCCTATTAGTGCTACAATATTAGCTCTGCGACAAGACCTCTATAGTATACCTTACTGCAACATTAATTGGG

ACAAGGCGCGTGATTATTGTGCAAAGgttagttagttaatcaatcactatatatatgtattcagtttgttag aatatattaatttagcccatgtcactacataatattttcatggattcaagattaagaacatcacgtagaata atgaagtacatcatttcagtacttggtatctcagaaaaaatatagactaagaaagctagtgttcttcaaaaa ttttatgttgtttcagGAGGACCTTCATTACCCACGCTCACGGGCACAAGATCTTATATCTGGTTGCCTAAC

GAAAATTGTGGAGCCAATTTTGAATTGGTGGCCAGCAAACAAGCTAAGAGATAGAGCTTTAACTAACCTCAT

GGAGCATATCCATTATGACGACGAATCAACCAAATATGTGGGCATTTGCCCTATTAACAAGgtgaaattatt ttcaaattgatttgcacctttttactttaataatgacggatgttattccattctaatgttttaacatgtttat tgtaattagGCATTGAACATGATTTGTTGTTGGGTAGAAAACCCAAATTCGCCTGAATTCCAACAACATCTT CCACGATTCCATGACTATTTGTGGATGGCGGAGGATGGAATGAAGGCACAGgttggtatagagctcttgtca gatattttgccaatttaactacgtgccaattcttcacaaccattaaccttttcatgaatatatatttcctc aaacaaaatgtgagaatcttttgggttacaaggatttttatttttcatctatatctaggttgcattcaataa gcatgtttgtgcatgtccgagttctcctgaaccaaactaaaatgcatattctctttagctgcacatagtgta tatgaaataaaattatggtaataatattttttactttagttaattctaatgacgaaatagttgatatgcctat atcgtttcgaatatataaatcagaggtagttagaaaaattattggacttacatcaaatgcaaactgtgaatg tataagtaatatgtatacaatcgcagGTATATGATGCATGTCATAGCTGGGAACTAGCGTTCATAATTCATG

CCTATTGTTCCACGGATCTTAGTAGCGAGTTTATCCCGACTCTAAAAAAGGCGCACGAGTTCATGAAGAACT

CACAGgtttgttgttctccatattatattattgctcaaattctgaaaagatctaacattaattgtctaccct tgaagGTTCTTTTCAACCACCCAAATCATGAAAGCTATTATCGCCACAGATCAAAAGGCTCATGGACCCTTT CAAGTGTAGATAATGGTTGGTCTGTATCTGATTGTACTGCGGAAGCTGTTAAGgttaacataagaaccatgt cttccaattgtacatatataagtacatatgtgaatacatgacgggttaccctgtataagttgaaatgaacta ttcatgaatatattgaatotacattaatattcattatttttttcagGCATTGCTACTATTATCAAAGATATCc

GCTGACCTTGTTGGCGATCCAATAAAACAAGACAGGTTGTATGATGCCATTGATTGCATCCTATCTTTCATG gtatgagaatctaaattggatcaattaacaaacgtacattactaaacaagggaaactatgcagacccattac taaagaaatgtgagcccacctagctagataattttatctaaaagtattaaattatattttgcacaacataca aaagttaaatttgttgtacaatgcatattattttctaaaaaaaatgcaaaaataattggagaaattttata aggtagtccacggtaatttaatccatttctataatgcaaatagagtctcactaatagcaggtctcctttttct cgttttgaagAATACAGATGGAACATTTTCTACCTACGAATGCAAACGGACATTCGCTTGGTTAGAGgttag tgatattcctttaaagtttataacatggtacaattaagatgaaatatcattttgtattgtatgacttgtc catgagaacaaggtattgggattgaataagaagtcaaaagaaaaccaaatacaacaatgatatattaattgt aattcttatggtcattttgcatttctctttcatacccaagaaattttttctcctgaacaataagtttggata acoctatcccctttaacaaaatatctcttctacgagctagGTTCTCAAcCCTTCTGAGAGTTTTCGGAACAT TGTCGTGGACTATcCgtaagacaaaaaacacctacttcataaattatctttacttctatattcaaatattca ttttcgcgaactgacttgatatacataataatggtcagATCTGTTGAATGCACATCATCTGTGGTTGATGCT

CTCATATTATTTAAAGAGACGAATCCACGATATCGAAGAGCAGAGATAGATAAATGCATTGAAGAAGCTGTT

GTATTTATTGAGAACAGTCAAAATAAGGATGGTTCATGgtaagtgacatgatataaaattatgcgttacaata acttttacttttgattaaatttgaaaatttattacttcttgtatctcatagGTATGGCTCATGGGGTATATG -continued (VIII)—Genomic sequence of β-amyrin synthase from *Avena strigosa*
(SEQ ID NO: 36)

TTTCGCATATGGATGCATGTTTGCAGTAAGGGCGTTGGTTGCTACAGGAAAAACCTACGACAATTGTGCTTC
TATCAGGAAATCATGCAAATTTGTCTTATCAAAGCAACAAACAACAGGTGGATGGGGTGAAGACTATCTTTC
TAGTGACAATGGGgtaatataacaaactactttaccccctataacattttactaatggtaaatcaaatccatc
atgattattcatagatttaagtcatacatgatatagtaaacatagaaattgatactagttgagagttttgtt
gttctataaatatactagttgagagttcagtagttctataagccatgcatggaattacgaaacattataaac
tcaacgcaagatgatatagttgacaaattttaaaaatatcatatgtcttgttaaaaaaaagatcctagttat
attttgagcatgaatatcttcaaatattgtgtatatgtgagaaaggtgatgtttaattgcacaaggtacact
aaataaaatggttaatttgtgtatgcccaaaaaagagagatatagaaagagctaaagtaaacttttaattga
cacatcttgttcttaacatttatttttatgaaagtctcagtacattcacgatacctagcaatatgaaaatt
cattgattagacagaagataaaattgccattccacaattattaaatcatatatgttaattttttgccttttg
cttattttgtcatgataatggatgcataacaccatgttttccaatggtctcatctactaatctcagatatc
ttaatacagcttggtctacaactgttacaccccagttttgatgaccgtgtccacaaatacattataaactac
tactaatgaoctaacacaaaaaaatgacgacaaagacaaatatccaatagaaggatcttttgtactgaacaa
atgaagaaaattgtacatatatattgtgtaatatttaatttgttttcctttagtgtactccatccatgaaaa
tgatattaaatcaatatttgcaatcatgcggtcaaatctgttcttctagatgcgtaagctaaagtcattata
tgtatatatatattttcaagaacacataggcatgttgtgttttctaatcacgttttgtacagGAATATATTG
ATAGCGGTAGGCCTAATGCTGTGACCACCTCATGGGCAATGTTGGCTTTAATTTATGCTGGACAGgtttgtc
aaatattttccttgtttgtctagaatatgaattttttattaaaaaggaaaagttctcactattcttgaata
gtcgagttatctaacagaataatttatattttgtttttttaataagGTTGAACGTGACCCAGTACCACTGTA
TAATGCTGCAAGACAGCTAATGAATATGCAGCTAGAAACAGGTGACTTCCCCCAACAGgtaatatgtttccg
tcctacatgttttcaaacaaaaatgcaaagtaatcttaagtttaattgaaactgatcttttgttaatgaaac
tcaatgtagaccttaagggaacaaccagtagaaataaaatacttgtgaattgataactctggaaagtgtatg
cattaatgttggtgtgaatgtggtaaatgttggcattgcgtcataatttttgcatcggtacttacaaagttt
aattaacactaatctcttgtcagattcaatgatcattaaaaattaagatataacctccatctagcttcttac
ttacagtttcaccttggtaataGACACATGGGTTGCTTCAACTCCTCCTTGAACTTCAACTACGCCAACT
ACCGCAATCTATACCCGATTATGGCTCTTGGGGAACTTCGCCGTCGACTTCTTGCGATTAAGAGCTGA (IX)—β-amyrin synthase promoter
(SEQ ID NO: 37)

ttcaaataaaaattacctgatctgacatgatcactggctacgccgagatt
ctacaaatatttctataagtagtttgtggattccaatatatataoggatt
ccgtaaagctctcttaccgatggtatgactttagtagtaaoaaaatcata
ggcttcgagtgaagattggctaocaactgtaatgtaagattgttgtccaa
gataagatactcaagttacagatgcactactctaatactaagagttattg
atctatattacggctcccgtaccgtagagatattgattctacgttcacct
tcttaaaaggagattcttgtacaatcaaaacaaatgggtctagctaccctt
ggtcaatatgtatttctatcggtatttagttataaaggagaggaatacag (IX)—β-amyrin synthase promoter
(SEQ ID NO: 37)

aataatttttttaactccatagtacctctattgctttcagtataaagagt
ttgatgcacggttctctgtactaataaatgttctattgttgattgattct
taaccgcatcctatgcaatttttaacctcaaaaaagtttcacggtacaocg
acttgccttactagccctactgttttcttgagaaggatgttcaaactttg
ggcttttgcatctaaaataagacacacatcattttttggtttattattcaa
caatgtgtgggaaaagcatacaacaatcaactcgatataccaccttcgcg
gagggcctctctttaaatgtctgggagtactacacatatgtaaagatga

(IX)—β-amyrin synthase promoter
(SEQ ID NO: 37)

tgcccacttacaaagaacgaggacaccacttaaaccgggtgtacaaagta ctacacatatgtaaagacgaggccatagaacaagcaagagcaccaagata tttagatccactaaaatgcaaccacctcgatgtccataaaaaatgatggt gacgcacaacactcaacaaatatcgataaaaatgatagtgtcctagttgc acatcttctaacatgttggtgtctattatgcacaagtgggcatggaagca agtaaatattgtgtactatagctactggtgactcgagtgtatctccaaga ctcgatagcaaacccgaagcctcttcagcttgtccacatatcattgtgga atgttcactacgactcgccacgccaagcataacctggataagccacgtgg gatatgagatttcccgcagcttccctctgagtgaggaggcagaactatac gcctcaacacgacgagccaccccctaaggctagtcatagtgggagtaact tgggtagtaacatattcctacatatattgcgaactaagcatttagatgac atgacatgcaattaaatgatgagagagagtcttatgataactagctatgt taccataacatcacacatttctaaaaaaataaatctatattataataaat

(IX)—β-amyrin synthase promoter
(SEQ ID NO: 37)

aaggttttgcatgataccacatctatgttattttgcactatgaagatagt aacttagactagtaacatatacatgttactactctaagttactccccaca atgaccagcctaacaccttttgtactgttttgcacatttgcagtttactt tttcttaggtgaagagaaaacacaagacataattttaatattttcaacttc attacgtgctggtgcaaataattttttacggtgcaattttcgacatgattt attgtatatttacagaaatttatgctccaaatttgtttggtaccttcagt attagtttctggacattgtacatattatgttgccgtataagctgagctag aaggatcattagtgtaattccatatatatctaaatgtacctgtggaatca catttgaggaagttccaatgatgccctttttgccctgcacacgca<u>tatat</u>

<u>aag</u>aaccctttgcccgcagcatagagctagtactagctagtatcccattg cttgttttcctcgacatacactgcccgttgttggtgcgcaccATG

(X) Putative transcription factor binding sites of the promoter region of SEQ ID NO: 37

```
    1 TTCAAATAAAAATTACCTGATCTGACATGATCACTGGCTACGCCGAGATT
   51 CTACAAATATTTCTATAAGTAGTTTGTGGATTCCAATATATATACGGATT
(101)    +ANNWAAAGNNN(P$DOF1_01(0.959))
(101)    +NWNWAAAGNGN(PSPBF_01(0.915))
  101 CCGTAAAGCTCTCTTACCGATGGTATGACTTTAGTAGTAACAAAATCATA
(126)                      -NCNCTTTWNWN(P$PBF_01(0.939))
(126)                      -NNNCTTTWNNT(p$DOF1_01(0.966))

(168)               +ACCWACCNN(P$P_01(0.856))
(174)                  +YAACSGMC(P$GAMYB_01(0.893))
  151 GGCTTCGAGTGAAGATTGGCTACCAACTGTAATGTAAGATTGTTGTCCAA
(188)                        -GKCSGTTR(P$GAMYB_01(0.905))

201 GATAAGATACTCAAGTTACAGATGCACTACTCTAATACTAAGAGTTATTG
  251 ATCTATATTACGGCTCCCGTACCGTAGAGATATTGATTCTACGTTCACCT
(302) +NWNWAAAGNGN(P$PBF_01(0.932))
(302) +ANNWAAAGNNN(P$DOF1_01(0.919))
(342)                                    +ACCWACCNN(P$P_01(0.906))
  301 TCTTAAAAGGAGATTCTTGTACAATCAAAACAAATGGGTCTAGCTACCTT (380)                         +NWNWAAGNGN(P$PBF_01(0.915))
(380)                         +ANNWAAAGNNN(P$DOF1_01(0.931))
(397)                                    +NCAATTATTNNN(P$ATHB1-01(0.864))
  351 GGTCAATATGTATTTCTATCGGTATTTAGTTATAAAGGAGAGGAATATACAG
(398)                                    -NNAATAATTGNNN(P$ATHB1_01
                                         (0.948))

(440)                            +NWNWAAAGNGN(P$PBF_01(0.936))
(440)                            +ANNWAAAGNN(P$DOF1_01(0.941))
```

-continued (X) Putative transcription factor binding sites of the promoter region of SEQ ID NO: 37

```
 401 AATAATTTTTTTAACTCCATAGTACCTCTATTGCTTTCAGTATAAAGAGT
(407)       -NWWWTTAACNAYWM(P$SBF1_01(0.899))
(431)                      -NNNCTTTWNNT(P$DOF1_01(0.910))
(431)                      -NCNCTTTWNWN(P$PBF_01(0.906))

451 TTGATGCACGGTTCTCTGTACTAATAAATGTTCTATTGTTGATTGATTCT
(496)                                 -NWWWTTAACNAYWM(P$SBF1_01(0.882))
(500)                                  -NTAACSGTTTTNN(P$MYBPH3_01
     (0.882))

(501) +YAACSGMC(P$GAMYB_01(0.899))
(528)                            +ANNWAAAGNNN(P$DOF1_01(0.931))
(528)                            +NWNWAAAGNGN(P$PBF_01(0.929))

501 TAACCGCATCCTATGCAATTTTAACCTCAAAAAAGTTTCACGGTACACCG
(517)            -NWWWTTAACNAYWN(P$SBF1_01(0.961))

551 ACTTGCCTTACTAGCCCTACTGTTTTCTTGAGAAGGATGTTCAAACTTTG
(593)                                -NNCTTTWNNT(P$DOF1_01(0.879))
(593)                                -NCNCTTTWNWN(P$PBF_01(0.860))
(600)                                   -NCNCTTTWNWN(P$PBF_01(0.938))
(600)                                   -NNNCTTTWNNT(P$DOF1_01(0.943))

(637)                             +NNNCAATTATTNNN(P$ATHB1_01(0.869))
 601 GGCTTTTGCATCTAAAATAAGACACACATCATTTTTGGTTTATTATTCAA (659)         +ANNWAAAGNNN(P$DOF1_01(0.925))
(659)         +NWNWAAAGNGN(P$PBF_01(0.922))
(671)                    +YAACSGMC(P$GAMYB_01(0.905))
 651 CAATGTGTGGGAAAAGCATACAACAATCAACTCGATATACCACCTTCGCG (739)                              +NWNWAAAGNGN(P$PBF_01(0.924))
 739)                              +ANNAAAGNNN(P$DOF1_01(0.965))
 701 GAGGGCCTCCTCTTTAAATGTCTGGGAGTACTACACATATGTAAAGATGA
(709)        -NCNCTTTWNWN(P$PBF_01(0.957))
(709)        -NNNCTTTWNNT(P$DOF1_01 (0.971))

(758)       +NWNWAAAGNGN(P$PBF_01(0.901))
(758)       +ANNWAAAGNNN(P$DOF1_01(0.877))
(791)                              +ANNWAAAGNNN(P$DOF1_01(0.871))
(791)                              +NWNWAAAGNGN(P$PBF_01(0.896))
 751 TGCCCACTTACAAAGAACGAGGACACCACTTAAACCGGGTGTACAAAGTA (809)      +NWNWAAAGNGN(P$PBF_01(0.932))
(809)      +ANNWAAAGNNN(P$DOF1_01(0.965))
 801 CTACACATATGTAAAGACGAGGCCATAGAACAAGCAAGAGCACCAAGATA (867)              +ACCWACCNN(P$P_01(0.852))
(869)                +YAACSGMC(P$GAMYB_01(0.947))
 851 TTTAGATCCACTAAAATGCAACCACCTCGATGTCCATAAAAAATGATGGT (907)       +YAACSGMC(P$GMYB_01(0.897))
 901 GACGCACAACACTCAACAAATATCGATAAAAATGATAGTGTCCTAGTTGC
 951 ACATCTTCTAACATGTTGGTGTCTATTATGCACAAGTGGGCATGGAAGCA
1001 AGTAAATATTGTGTACTATAGCTACTGGTGACTCGAGTGTATCTCCAAGA
1051 CTCGATAGCAAACCCGAAGCCTCTTCAGCTTGTCCACATATCATTGTGGA (1141)                         +NNNSACGTGNCM(P$GBP_Q6(0.949))
1101 ATGTTCACTACGACTCGCCACGCCAAGCATAACCTGGATAAGCCACGTGG
(1141)                          -KGNCACGTSNNN(P$GBP_Q6(0.944))

1151 GATATGAGATTTCCCGCAGCTTCCCTCTGAGTGAGGAGGCAGAACTATAC
1201 GCCTCAACACGACGAGCCACCCCCTAAGGCTAGTCATAGTGGGAGTAACT
1251 TGGGTAGTAACATATTCCTACATATATTGCGAACTAAGCATTTAGATGAC
(1251) -NNGGTWGGT(P$P_01(0.855))

(1338)                         +YAACSGMC(P$GPAMYB_01(0.857))
1301 ATGACATGCAATTAAATGATGAGAGAGTCTTATGATAACTAGCTATGT
1351 TACCATAACATCACACATTTCTAAAAAAATAAATCTATATTATAATAAAT
1401 AAGGTTTTGCATGATACCACATCTATGTTATTTTGCACTATGAAGATAGT
1451 AACTTAGACTAGTAACATATACATGTTACTACTCTAAGTTACTCCCCACA
1501 ATGACCAGCCTAACACCTTTTGTACTGTTTTGCACATTTGCAGTTTACTT
(1514)             -NCNCTTTWNWN(P$PBF_01(0.927))
(1514)             -NNNCTTTWNNT(P$DOF1_01(0.933))
(1545)                            -NCNCTTTWNWN(P$PBF_01(0.945))
1545)                             -NNNCTTTWNNT(P$DOF1_01(0.940))
```

| (X) Putative transcription factor binding sites of the promoter region of SEQ ID NO: 37 |
| --- |

```
(1579)                              +KWRTNGTTAAWWWN(P$SBF1_01(0.854))
 1551 TTTCTTAGGTGAAGAGAAAAACACAAGACATAATTTTAATATTTCAACTTC
(1581)                              -NWWWTTAACNAYWM(P$SBF1_01(0.878))

(1613)           +NNNCAATTATTNNN(P$ATHB1_01(0.860))
 1601 ATTACGTGCTGGTGCAAATAATTTTTACGGTGCAATTTTCGACATGATTT
(1614)           -NNNAATAATTGNNN(P$ATHB1-01(0.945))

1651 ATTGTATATTTACAGAAATTTATGCTCCAAATTTGTTTGGTACCTTCAGT
 1701 ATTAGTTTCTGGACATTGTACATATTATGTTGCCGTATAAGCTGAGCTAG
 1751 AAGGATCATTAGTGTAATTCCATATATATCTAAATGTACCTGTGGAATCA
 1801 CATTTGAGGAAGTTCCAATGATGCCCTTTTTGCCCTGCACACGCATATAT
(1823)                     -NNNCTTTWNNT(P$DOF1_01(0.913))
(1823)                     -NCNCTTTWNWN(PSPBF_01(0.943))

1851 AAGAACCCTTTGCCCGCAGCATAGAGCTAGTACTAGCTAGTATCCCATTG
(1655)     -NCNCTTTWNWN(P$PBF_01(0.880))
(1855)     -NNNCTTTWNNT(P$DOF1_01(0.859))
 1901 CTTGTTTTCCTCGCATACACTGCCCGTTGTTGGTGCGCACCATG
(1922)                   -GKCSGTTR(PSGAMYB_01(0.961))
```

TABLE 1

Specific primers for amplifying A. strigosa β-amyrin synthase

| No. | Amino acid sequence | Forward primers | Reverse primers |
| --- | --- | --- | --- |
| I. | KSNNGFL | AAGTCGAACAATGGCTTCCTT | AAGGAAGCCATTGTTCGACTT |
| II. | VWEYDADAGT | GTGGGAGTACGACGCCGATGCCGGCACG | CGTGCCGGCATCGGCGTCGTACTCCCAC |
| III. | RVRAEFTK | AGGGTGCGTGCGGAATTCACAAAG | CTTTGTGAATTCCGCACGCACCCT |
| IV. | PANIPTEA | CCGGCGAATATTCCGACAGAAGCC | GGCTTCTGTCGGAATATTCGCCGG |
| V. | KSTEVTHETIYES | AAGAGTACACAGGTCACTCACGAGACTATCTACGAATCA | TGATTCGTAGATAGTCTCGTGAGTGACCTCTGTACTCTT |
| VI. | IMPINIFS | ATTATGCCTATCAATATATTCTCT | AGAGAATATATTGATAGGCATAAT |
| VII. | RSLDTFLS | AGAGAATATATTGATAGGCATAAT | ATTATGCCTATCAATATATTCTCT |
| VIII. | NQQNEDGGWGKMVLGP | AATCAACAGAATGAAGATGGTGGTTGGGGAAAAATGGTTCTTGGCCCA | TGGGCCAAGAACCATTTTTCCCCAACCACCATCTTCATTCTGTTGATT |
| IX. | GSCMNYATLM | GGATCGTGTATGAATTATGCAACCTTAATG | CATTAAGGTTGCATAATTCATACACGATCC |
| X. | KRNGDHKDALEK | AAGCGAAATGGTGATCATAAGGATGCATTGGAAAAA | TTTTTCCAATGCATCCTTATGATCACCATTTCGCTT |
| XI. | SHGTATAIPQ | TCTCATGGAACTGCAACTGCAATACCACAG | CTGTGGTATTGCAGTTGCAGTTCCATGAGA |
| XII. | IIPELWLVPH | ATTATACCTGAATTGTGGTTGGTTCCACAT | ATGTGGAACCAACCACAATTCAGGTATAAT |
| XIII. | RFWCFTRLIYMSMA | CGTTTTTGGTGTTTTACCCGGTTGATATACATGTCAATGGCA | TGCCATTGACATGTATATCAACCGGGTAAAACACCAAAAACG |
| XIV. | ALRQDLYSIPYCN | GGTCTGCGACAAGACCTCTATAGTATACCTTACTGCAAC | GTTGCAGTAAGGTATACTATAGAGGTCTTGTCGCAGAGC |

TABLE 1-continued

Specific primers for amplifying *A. strigosa* β-amyrin synthase

| No. | Amino acid sequence | Forward primers | Reverse primers |
|---|---|---|---|
| XV. | WDKARDYC | TGGGACAAGGCGCGTGATTATTGT | ACAATAATCACGCGCCTTGTCCCA |
| XVI. | RSRAQDLISGCLTK | CGCTCACGGGCACAAGATCTTATATCTGGTTGCCTAACGAAA | TTTCGTTAGGCAACCAGATATAAGATCTTGTGCCCGTGAGCG |
| XVII. | ILNWWPANKLR | ATTTTGAATTGGTGGCCAGCAAACAAGCTAAGA | TCTTAGCTTGTTTGCTGGCCACCAATTCAAAAT |
| XVIII. | DRALTNLMEH | GATAGAGCTTTAACTAACCTCATGGAGCAT | ATGCTCCATGAGGTTAGTTAAAGCTCTATC |
| XIX. | STKYVGICPI | TCAACCAAATATGTGGGCATTTGCCCTAT | AATAGGGCAAATGCCCACATATTTGGTTGA |
| XX. | ICCWVENPNSPE | ATTTGTTGTTGGGTAGAAAACCCAAATTCGCCTGAA | TTCAGGCGAATTTGGGTTTTCTACCCAACAACAAAT |
| XXI. | AQVYDGCHS | GCACAGGTATATGATGGATGTCATAGC | GCTATGACATCCATCATATACCTGTGC |
| XXII. | ELAFIIHAYC | GAACTAGCGTTCATAATTCATGCCTATTGT | ACAATAGGCATGAATTATGAACGCTAGTTC |
| XXIII. | STDLTSEFI | TCCACGGATCTTACTAGCGAGTTTATC | GATAAACTCGCTAGTAAGATCCGTGGA |
| XXIV. | LFNHPNHESY | CTTTTCAACCACCCAAATCATGAAAGCTAT | ATAGCTTTCATGATTTGGGTGGTTGAAAAG |
| XXV. | LSSVDNGWS | CTTTCAAGTGTAGATAATGGTTGGTCT | AGACCAACCATTATCTACACTTGAAAG |
| XXVI. | KISADLVGDPIKQD | AAGATATCCGCTGACCTTGTTGGCGATCCAATAAAACAAGAC | GTCTTGTTTTATTGGATCGCCAACAAGGTCAGCGGATATCTT |
| XXVII. | IDCILSFMNTD | ATTGATTGCATCCTATCTTTCATGAATACAGAT | ATCTGTATTCATGAAAGATAGGATGCAATCAAT |
| XXVIII. | TFSTYECKRTFA | ACATTTTCTACCTACGAATGCAAACGGACATTCGCT | AGCGAATGTCCGTTTGCATTCGTAGGTAGAAAATGT |
| XXIX. | NPSESFRN | AACCCTTCTGAGAGTTTTCGGAAC | GTTCCGAAAACTCTCAGAAGGGTT |
| XXX. | VVDALIL | GTGGTTGATGCTCTCATATTA | TAATATGAGAGCATCAACCAC |
| XXXI. | ETNPRYRRA | GAGACGAATCCACGATATCGAAGAGCA | TGCTCTTCGATATCGTGGATTCGTCTC |
| XXXII. | DKCIEEAVVF | GATAAATGCATTGAAGAAGCTGTTGTATTT | AAATACAACAGCTTCTTCAATGCATTTATC |
| XXXIII. | CMFAVRALVAT | TGCATGTTTGCAGTAAGGGCGTTGGTTGCTACA | TGTAGCAACCAACGCCCTTACTGCAAACATGCA |
| XXXIV. | DNCASIRKSCK | GACAATTGTGCTTCTATCAGGAAATCATGCAAA | TTTGCATGATTTCCTGATAGAAGCACAATTGTC |
| XXXV. | VLSKQQTT | GTCTTATCAAAGCAACAAACAACA | TGTTGTTTGTTGCTTTGATAAGAC |
| XXXVI. | DYLSSDNGEYIDS | GACTATCTTTCTAGTGACAATGGGGAATATATTGATAGC | GCTATCAATATATTCCCCATTGTCACTAGAAAGATAGTC |
| XXXVII. | GRPNAVTTS | GGTAGGCCTAATGCTGTGACCACCTCA | TGAGGTGGTCACAGCATTAGGCCTACC |
| XXXVIII. | YAGQVERDPV | TATGCTGGACAGGTTGAACGTGACCCAGTA | TACTGGGTCACGTTCAACCTGTCCAGCATA |
| XXXIX. | YNAARQLMNMQLET | TATAATGCTGCAAGACAGCTAATGAATATGCAGCTAGAAACA | TGTTTCTAGCTGCATATTCATTAGCTGTCTTGCAGCATTATA |

TABLE 1-continued

Specific primers for amplifying *A. strigosa* β-amyrin synthase

| No. | Amino acid sequence | Forward primers | Reverse primers |
|---|---|---|---|
| XL. | CFNSSLNFNYANY | TGCTTCAACTCCTCCTTGAACTTCAACTA CGCCAACTAC | GTAGTTGGCGTAGTTGAAGTT CAAGGAGGAGTTGAAGCA |
| XLI. | IMALGELRRRLLA IKS | ATTATGGCTCTTGGGGAACTTCGCCGTCG ACTTCTTGCGATTAAGAGCTGA | TCAGCTCTTAATCGCAAGAAG TCGACGGCGAAGTTCCCCAAG AGCCATAAT |

In Table I, Amino acid sequences I–XLI correspond to SEQ ID NOS: 50–90; Forward primers I–XLI correspond to SEQ ID NOS: 91–131; Reverse primers I–XLI correspond to SEQ ID NOS: 132–172.

TABLE 2

In Table 2 - Forward primers 1–11 and reverse primers 1–11 correspond to SEQ ID NOS: 173–183 and 184–194 respectively.

| Number | Forward primers | Reverse primers |
|---|---|---|
| 1 | ASWSKAMMAATRRYTTYVTW | WABRAARYYATTKKTMSWST |
| 2 | WSRRAKAACMGGTWYCAG | CTGRWACCKGTTMTYYSW |
| 3 | KYTMTTYWTYMTKCCDMYC | GRKHGGMAKRAWRAAKARM |
| 4 | KWCGCTACATWTACWRTC | GAYWGTAWATGTAGCGWM |
| 5 | TGGTGRTSWWAASRATGCMT | AKGCATYSTTWWSAYCACCA |
| 6 | KGATCTHAYTVRYGARWTTVKH | DMBAAWYTCRYBARTDAGATCM |
| 7 | AAARSYATNYATCGYCACA | TGTGRCGATRNATRSYTTT |
| 8 | GARTGCACWTCATCDGYR | YRCHGATGAWGTGCAYTC |
| 9 | GGAAARACMTACDACAAYT | ARTTGTHGTAKGTYTTTCC |
| 10 | YTTYCCCCAACAGGAAMWM | KWKTTCCTGTTGGGGRAAR |
| 11 | TACCGSAATMTATACCCRWT | AWYGGGTATAKATTSCGGTA |

TABLE 3 primers used in order to cover the complete genomic sequence

| | | |
|---|---|---|
| XLII. | AMYstaF5: | 5'-CCATGTGGAGGCTAACAATAGGTGAGGG-3' |
| XLIII. | AMYstaF6: | 5'-TTTCCTCGCATACACTGCCCGTTGTT-3' |
| XLIV. | AMY01F: | 5'-TATTCCGACAGAAGCCAA-3' |
| XLV. | AMY01R: | 5'-TCTTTGTGAATTCCGCAC-3' |
| XLVI. | AMY02F: | 5'-GTTGGGGAAAAATGGTTC-3' |
| XLVII. | AMY03F: | 5'-TTTTCTTCCGATTCACCC-3' |
| XLVIII. | AMY04F: | 5'-ATTGTGGAGCCAATTTTG-3' |
| XLIX. | AMY05F: | 5'-TGGATGTCATAGCTGGGA-3' |
| L. | AMY06F: | 5'-TATCCGCTGACCTTGTTG-3' |
| LI. | AMY07F: | 5'-CGAATCCACGATATCGAA-3' |
| LII. | AMY08F: | 5'-GTGGATGGGGTGAAGACT-3' |

TABLE 3-continued primers used in order to cover the complete genomic sequence

| | | |
|---|---|---|
| LIII. | AMY09F: | 5'-TATGGCTCTTGGGGAACT-3' |
| LIV. | AMY10F: | 5'-GTATGGATTTCGTACCGTAAAT-3' |
| LV. | AMY11F: | 5'-CCTGCGACAAGACCTCTATA-3' |
| LVI. | AMY12F: | 5'-CTCAACCCTTCTGAGAGTTTT-3' |
| LVII. | AMY13F: | 5'-CAGCTTGGTCTACAACTGTTAC-3' |
| LVIII. | AMY014F: | 5'-CAGAGGTAGTTAGAAAAATTATTGGACT-3' |
| LIX. | AMY015F: | 5'-GGCGGAGGATGGAATGAAGGCA-3' |
| LX. | AMY016F: | 5'-CAGTGGGATTCTCTTCATTATGC-3' |
| LXI. | AMY017R: | 5'-AGCCTTTTGATCTGTGGCGATA-3' |
| LXII. | AMY018F: | 5'-GTGGCTCATCACATTGATCACA-3' |
| LXIII. | AMY019F: | 5'-TGGGCAATGTTGGCTTTAATTT-3' |
| LXIV. | AMYendR3: | 5'-GCCTAGACATCCATGTTTGTTTCCATATCA-3' |
| LXV. | AMYendR5: | 5'-TATTTCTCAAAGAAAATAACGCATGAATGCTC-3' |

In Table 3, primer XLII corresponds to SEQ ID NO: 5; primers LXIII–LXIV correspond to SEQ ID NOS: 195–216 and primer LXV corresponds to SEQ ID NO: 6

Blast Analysis

Partial cDNA Sequence (clone ort1s.pk001.c14)

Blastx search at the National Center for Biotechnology Information (NCBI) revealed homology with:

The cycloartenol synthase (AB025968) from *Glycyrrhiza glabra*. Score=109 (bits), E-Value=5e-24, Identities=45/86 (52%).

The cycloartenol synthase (AB033334) from *Luffa cylindrica*. Score=109 (bits), E-Value=4e-24, Identities=44/86 (51%).

The cycloartenol synthase (AF169966) from *Oryza sativa*. Score=107 (bits), E-Value=2e-23, Identities=48/83 (57%).

The oxidosqualene cyclase (AB025353) from *Allium macrostemon*. Score=104 (bits), E-Value=1e-22, Identities=47/83 (56%).

The cycloartenol synthase (AC005171) from *Arabidopsis thaliana*. Score=104 (bits), E-Value=2e-22, Identities=44/86 (51%).

The cycloartenol synthase (AB009029) from *Panax ginseng*. Score=104 (bits), E-Value=1e-22, Identities=43/86 (50%).

The cycloartenol synthase (D89619) from *Pisum sativum*. Score=102 (bits), E-Value=6e-22, Identities=43/86 (50%).

The beta-amyrin synthase (AB014057) from *Panax ginseng*. Score=98.7 (bits), E-Value=9e-21, Identities=43/84 (51%).

For the search the non-redundant GenBank CDS translations, PDB, SwissProt, SPupdate and PIR databases were used with a BLOSUM62 Matrix and the Existence11, Extension1 Gap Penalties.

Below are shown the results of further Blastx searches at the National Center for Biotechnology Information (NCBI), using the non-redundant GenBank CDS translations, PDB, SwissProt, SPupdate and PIR databases with a BLOSUM62 Matrix, showed homology to the beta-amyrin synthase cDNA from *Panax ginseng* and to cycloartenol synthase genes from other plant species.

1. Cycloartenol synthase (D89619) from *Pisum sativum*. Score=(131), E-Value=4e-30, Identities=58/127 (45%).

2. Cycloartenol synthase (AC005171) from *Arabidopsis thaliana*. Score=(131), E-Value=4e-30, Identities=57/127 (44%).

3. Cycloartenol synthase (AF169966) from *Oryza sativa*. Score=(130), E-Value=5e-30, Identities=63/125 (50%).

4. Cycloartenol synthase(AB025968) from *Glycyrrhiza glabra*. Score=(128), E-Value=2e-29, Identities=57/127 (44%).

5. Oxidosqualene cyclase (AB025353) from *Allium macrostemon*. Score=(126), E-Value=9e-29, Identities=57/127 (44%).

6. Cycloartenol synthase (AB009029) from *Panax ginseng*. Score=(125), E-Value=1e-28, Identities=54/127 (42%).

7. Beta-amyrin synthase (AB014057) from *Panax ginseng*. Score=(118), E-Value=3e-26, Identities=57/127 (44%).

The invention claimed is:

1. An isolated nucleic acid which comprises a nucleotide sequence selected from the group consisting of:
   a) a nucleotide sequence encoding the polypeptide of SEQ ID NO: 15;
   b) the nucleotide sequence of SEQ ID NO: 14;
   c) the nucleotide sequence of SEQ ID NO: 36; and
   d) a nucleotide sequence encoding a functional β amyrin synthase having at least 95% homology to SEQ ID NO: 15.

2. The isolated nucleic acid as claimed in claim 1, wherein the nucleotide sequence comprises SEQ ID NO: 14 or SEQ ID NO: 36.

3. The isolated nucleic acid as claimed in claim 1, wherein the nucleotide sequence encodes the polypeptide of SEQ ID NO: 15.

4. An isolated nucleic acid which comprises the complement of the nucleotide sequence of SEQ ID NO: 14 or 36.

5. A recombinant vector which comprises the nucleic acid of claim 1.

6. The recombinant vector as claimed in claim 5, wherein the nucleic acid is operably linked to a promoter.

7. The recombinant vector as claimed in claim 5 which is a plant transformation vector.

8. A method of producing a transformed host cell comprising introducing the vector of claim 5 into a host cell.

9. A host cell transformed with the nucleic acid of claim 1.

10. The host cell as claimed in claim 9, which is *Saccharomyces cerevisiae*.

11. The host cell as claimed in claim 9, which is a plant cell.

12. A method for producing a transgenic plant, which method comprises the steps of:
   a) introducing the vector of claim 5 into a plant cell to produce a transformed plant cell; and,
   b) regenerating a plant from the transformed plant cell.

13. A transgenic plant which is produced by the method of claim 12.

14. The transgenic plant as claimed in claim 13, which is selected from the group consisting of barley, phaseolus, pea, sugar beet, maize, oat, solanum, allium, cucurbitaceae, yam, rice, rye, sorghum, soyabean, spruce, strawberry, sugarcane, sunflower, tomato, and wheat.

15. A transgenic seed or progeny from the transgenic plant as claimed in claim 14.

16. A method of making a polypeptide having β-amyrin synthase activity, which method comprises the step of causing or allowing expression of the polypeptide from the nucleic acid of claim 1 in a suitable host cell; and isolating the polypeptide from the host cell.

17. A method for altering triterpenoid synthesis in a plant, which method comprises introducing the nucleic acid as claimed in claim 1 into the plant.

18. A method for altering resistance to a fungal pathogen in a plant, which method comprises introducing the nucleic acid as claimed in claim 1 into the plant.

19. The method as claimed in claim 18, wherein the fungal pathogen is selected from the group consisting of *Gaeumannomyces* var *avenae, Gaeumannomyces* var *tritici, Fusarium culmorum, Fusarium avanaceum, Stagonospora nodorum,* and *Stagonospora avena.*

20. A method as claimed in claim 17 wherein the triterpenoid is an oleanane-type triterpene saponin, and the method further comprises of isolating said triterpenoid from the plant.

21. A method for reducing the level of at least on triterpenoid in a plant, which method comprises introducing the nucleic acid of claim 4 into the plant.

22. A recombinant vector which comprises the nucleic acid of claim 4.

23. A host cell transformed with the nucleic acid of claim 4.

* * * * *